US008661562B2

(12) United States Patent
Calilung et al.

(10) Patent No.: US 8,661,562 B2
(45) Date of Patent: Mar. 4, 2014

(54) EYEWEAR WITH RIGID LENS SUPPORT

(75) Inventors: Ryan Calilung, Irvine, CA (US); Jason Janavicius, Laguna Niguel, CA (US)

(73) Assignee: Oakley, Inc., Foothill Ranch, CA (US)

( * ) Notice: Subject to any disclaimer, the term of this patent is extended or adjusted under 35 U.S.C. 154(b) by 37 days.

(21) Appl. No.: 13/465,272

(22) Filed: May 7, 2012

(65) Prior Publication Data
US 2012/0218507 A1   Aug. 30, 2012

Related U.S. Application Data

(63) Continuation of application No. 13/051,889, filed on Mar. 18, 2011.

(60) Provisional application No. 61/315,752, filed on Mar. 19, 2010, provisional application No. 61/426,222, filed on Dec. 22, 2010.

(51) Int. Cl.
*A61F 9/00* (2006.01)

(52) U.S. Cl.
USPC .................................................. 2/12; 351/86

(58) Field of Classification Search
USPC ............. 2/426–427, 429, 431, 438, 439, 441, 2/442, 443, 445, 446, 454, 12; 351/44, 351/103–109, 83, 86, 121, 140, 141, 153; 16/228
See application file for complete search history.

(56) References Cited

U.S. PATENT DOCUMENTS

| 245,268 | A | 8/1881 | Andross |
|---|---|---|---|
| 1,308,477 | A | 7/1919 | Blanchard |
| 1,839,386 | A | 1/1932 | Fischer |
| 2,443,422 | A | 6/1948 | Hansen |
| 2,652,746 | A | 12/1950 | Shanks |
| 2,556,847 | A | 6/1951 | MacLean |
| 2,610,323 | A | 9/1952 | Johnson |
| 3,214,767 | A | 11/1965 | Weber |
| 3,229,303 | A | 1/1966 | Jonassen |
| 3,383,707 | A | 5/1968 | McNeill |
| 3,395,964 | A | 8/1968 | Chartrice |

(Continued)

FOREIGN PATENT DOCUMENTS

| EP | 0121 018 | 10/1984 |
|---|---|---|
| EP | 0496 292 | 1/1991 |

(Continued)

OTHER PUBLICATIONS

U.S. Appl. No. 29/383,478, filed Jan. 18, 2011, Moritz.

(Continued)

*Primary Examiner* — Clinton T Ostrup
*Assistant Examiner* — Andrew W Sutton
(74) *Attorney, Agent, or Firm* — Knobbe Martens Olson & Bear, LLP

(57) ABSTRACT

Eyewear is provided having a frame that can releasably engage a lens. The frame can have an engagement mechanism that includes an active restraint member and a passive restraint member. The active restraint member can have a first component and a second component that are operatively coupled together such that the first and second components rotate together between open and closed positions. The second component can also be configured to slide relative to the first component to engage a portion the frame when the first and second components are in the closed position to maintain the lens fitted against the frame.

13 Claims, 46 Drawing Sheets

(56) References Cited

U.S. PATENT DOCUMENTS

| | | | |
|---|---|---|---|
| 3,552,840 A | 1/1971 | Braget | |
| 3,691,565 A | 9/1972 | Galonek | |
| 3,826,564 A | 7/1974 | Werling, Sr. | |
| 3,829,201 A | 8/1974 | Whiting | |
| 3,901,589 A | 8/1975 | Bienenfeld | |
| 3,931,646 A * | 1/1976 | Loughner | 2/452 |
| 4,023,214 A | 5/1977 | Waldherr | |
| 4,056,853 A | 11/1977 | Bottazzini et al. | |
| 4,176,921 A | 12/1979 | Matthias | |
| 4,264,987 A | 5/1981 | Runckel | |
| 4,304,469 A | 12/1981 | Solomon | |
| 4,314,814 A | 2/1982 | Deroode | |
| 4,340,282 A | 7/1982 | Murakami | |
| 4,357,080 A | 11/1982 | Solomon | |
| 4,471,496 A | 9/1984 | Gardner, Jr. et al. | |
| 4,515,448 A | 5/1985 | Tackles | |
| 4,527,291 A | 7/1985 | Nussbickl | |
| 4,616,367 A | 10/1986 | Jean et al. | |
| 4,662,966 A | 5/1987 | Sumi et al. | |
| 4,670,084 A | 6/1987 | Durand | |
| 4,686,712 A | 8/1987 | Spiva | |
| 4,715,702 A | 12/1987 | Dillon | |
| 4,759,622 A | 7/1988 | Schmidthaler | |
| 4,813,775 A | 3/1989 | Kaksonen | |
| 4,822,158 A | 4/1989 | Porsche | |
| 4,843,655 A | 7/1989 | Hegendorfer | |
| 4,859,048 A | 8/1989 | Jannard | |
| 4,867,550 A | 9/1989 | Jannard | |
| 4,901,374 A | 2/1990 | Van der Woude | |
| 4,951,322 A | 8/1990 | Lin | |
| 4,983,030 A | 1/1991 | Chandler | |
| 5,016,293 A | 5/1991 | Lickle | |
| 5,048,944 A | 9/1991 | Porsche | |
| 5,056,163 A | 10/1991 | Chou | |
| 5,069,541 A | 12/1991 | Holmes et al. | |
| 5,144,344 A | 9/1992 | Takahashi et al. | |
| 5,182,586 A | 1/1993 | Bennato | |
| 5,182,587 A | 1/1993 | Hyoi | |
| 5,208,614 A | 5/1993 | Jannard | |
| 5,257,050 A | 10/1993 | Wiedner | |
| 5,270,743 A | 12/1993 | Hofmair et al. | |
| 5,308,426 A | 5/1994 | Claveau | |
| 5,357,292 A | 10/1994 | Wiedner | |
| 5,373,331 A | 12/1994 | Vallalla et al. | |
| 5,390,369 A | 2/1995 | Tubin | |
| 5,400,089 A | 3/1995 | Danloup et al. | |
| 5,410,763 A | 5/1995 | Bolle | |
| 5,418,580 A | 5/1995 | Sondrol | |
| 5,455,639 A | 10/1995 | Magdelaine et al. | |
| 5,467,148 A | 11/1995 | Conway | |
| 5,536,828 A | 7/1996 | Deluca et al. | |
| 5,541,674 A | 7/1996 | Jannard | |
| 5,576,775 A | 11/1996 | Bolle | |
| 5,583,583 A | 12/1996 | Wilson | |
| 5,587,747 A | 12/1996 | Bernheiser | |
| 5,602,603 A | 2/1997 | Bondet | |
| 5,610,668 A | 3/1997 | Mage | |
| 5,617,588 A | 4/1997 | Canavan et al. | |
| 5,638,145 A | 6/1997 | Jannard et al. | |
| 5,641,372 A | 6/1997 | Okuno | |
| 5,648,832 A | 7/1997 | Houston et al. | |
| 5,652,954 A | 8/1997 | Paiement et al. | |
| 5,689,323 A | 11/1997 | Houston et al. | |
| 5,708,489 A | 1/1998 | Jannard | |
| 5,727,251 A | 3/1998 | Sherlock et al. | |
| 5,752,280 A | 5/1998 | Hill | |
| 5,760,866 A | 6/1998 | Wedeck et al. | |
| 5,768,716 A | 6/1998 | Porsche | |
| 5,790,230 A | 8/1998 | Sved | |
| 5,798,017 A | 8/1998 | Claveau | |
| 5,802,622 A | 9/1998 | Baharad et al. | |
| 5,805,261 A | 9/1998 | Houston et al. | |
| 5,815,235 A | 9/1998 | Runckel | |
| 5,862,529 A | 1/1999 | Moodie et al. | |
| 5,898,469 A * | 4/1999 | Wang | 351/86 |
| 5,914,767 A | 6/1999 | Wedeck et al. | |
| 5,929,963 A | 7/1999 | McNeal | |
| 5,963,293 A | 10/1999 | Jannard | |
| 5,969,789 A | 10/1999 | Houston et al. | |
| 5,971,536 A | 10/1999 | Chiu | |
| 6,009,564 A | 1/2000 | Tackles et al. | |
| 6,010,217 A | 1/2000 | Houston et al. | |
| 6,010,218 A | 1/2000 | Houston et al. | |
| 6,047,410 A | 4/2000 | Dondero | |
| 6,062,688 A | 5/2000 | Vinas | |
| 6,086,199 A | 7/2000 | Holland et al. | |
| 6,094,751 A | 8/2000 | Parks | |
| 6,098,204 A | 8/2000 | Arnette | |
| 6,105,177 A | 8/2000 | Paulson et al. | |
| 6,106,116 A | 8/2000 | Houston et al. | |
| 6,119,279 A | 9/2000 | Haslbeck | |
| 6,131,246 A | 10/2000 | Paulson et al. | |
| 6,168,271 B1 | 1/2001 | Houston et al. | |
| 6,193,367 B1 | 2/2001 | Lee | |
| 6,224,209 B1 | 5/2001 | Chen | |
| 6,250,756 B1 | 6/2001 | Jannard | |
| 6,273,564 B1 | 8/2001 | Wedeck et al. | |
| 6,276,794 B1 | 8/2001 | Chiang | |
| 6,282,727 B1 | 9/2001 | Lindahl | |
| 6,296,357 B1 | 10/2001 | Bof | |
| 6,349,422 B1 | 2/2002 | Schleger et al. | |
| 6,357,873 B1 | 3/2002 | Spindelbalker | |
| 6,428,165 B1 | 8/2002 | Rivera | |
| 6,464,353 B1 | 10/2002 | Spindelbalker | |
| 6,477,717 B1 | 11/2002 | Winefordner et al. | |
| 6,533,412 B1 | 3/2003 | Wang et al. | |
| 6,550,912 B2 | 4/2003 | Vitaloni | |
| 6,561,647 B1 | 5/2003 | Chen | |
| 6,564,804 B2 | 5/2003 | Salatka et al. | |
| 6,637,877 B1 | 10/2003 | Hartley et al. | |
| 6,641,263 B2 | 11/2003 | Olney | |
| 6,712,465 B1 | 3/2004 | Teng | |
| 6,715,157 B2 | 4/2004 | Mage | |
| 6,732,383 B2 | 5/2004 | Cleary et al. | |
| 6,742,890 B1 | 6/2004 | Teng | |
| 6,742,891 B2 | 6/2004 | Chen | |
| 6,786,592 B2 | 9/2004 | Rivera | |
| 6,804,835 B2 | 10/2004 | Chou | |
| 6,834,951 B2 | 12/2004 | Xie | |
| 6,863,395 B1 * | 3/2005 | Teng | 351/103 |
| 6,923,537 B2 | 8/2005 | Hartley et al. | |
| 6,926,404 B2 | 8/2005 | Bassahon et al. | |
| 6,929,364 B1 | 8/2005 | Jannard | |
| 6,938,277 B2 | 9/2005 | Lindahl | |
| 6,948,813 B2 | 9/2005 | Parks | |
| 6,953,247 B1 | 10/2005 | Duffy et al. | |
| 6,959,988 B1 | 11/2005 | Sheldon | |
| 6,964,067 B1 | 11/2005 | Hartman | |
| 6,964,477 B1 | 11/2005 | Teng | |
| 7,000,263 B2 | 2/2006 | McNeal | |
| 7,003,802 B2 * | 2/2006 | Broersma | 2/9 |
| 7,058,991 B2 | 6/2006 | Hartman | |
| 7,083,276 B2 | 8/2006 | Olney | |
| 7,090,346 B2 | 8/2006 | Tsai | |
| 7,100,215 B2 | 9/2006 | Shiue | |
| 7,137,426 B2 | 11/2006 | Neri et al. | |
| 7,137,700 B2 | 11/2006 | DiChiara et al. | |
| 7,150,525 B1 | 12/2006 | Yang | |
| 7,163,289 B2 | 1/2007 | Wedeck et al. | |
| 7,200,875 B2 | 4/2007 | Dondero | |
| 7,204,589 B2 | 4/2007 | Pieterman | |
| 7,219,992 B1 | 5/2007 | Wu | |
| 7,219,993 B1 | 5/2007 | Chiou | |
| 7,222,958 B1 | 5/2007 | Chiou | |
| 7,222,959 B2 | 5/2007 | Jannard | |
| 7,234,808 B2 | 6/2007 | Bruck | |
| 7,241,007 B2 | 7/2007 | Cody | |
| 7,267,737 B2 | 9/2007 | Neri et al. | |
| 7,278,733 B2 | 10/2007 | Olney | |
| 7,296,887 B1 | 11/2007 | Hsiung | |
| 7,328,999 B2 | 2/2008 | Zelman | |
| 7,343,631 B2 | 3/2008 | Lin | |
| 7,390,086 B2 | 6/2008 | Lee | |
| 7,396,124 B1 | 7/2008 | Wang | |

(56) References Cited

U.S. PATENT DOCUMENTS

| | | |
|---|---|---|
| 7,425,065 B2 | 9/2008 | Wang |
| 7,452,069 B2 | 11/2008 | Lipawsky |
| 7,481,529 B1 | 1/2009 | Chen |
| 7,497,569 B2 * | 3/2009 | Webb .......................... 351/106 |
| 7,520,217 B2 | 4/2009 | Roberts et al. |
| 7,520,605 B1 | 4/2009 | Chen |
| 7,526,813 B2 | 5/2009 | Tominaga et al. |
| 7,553,013 B2 | 6/2009 | Tsai |
| 7,563,341 B2 | 7/2009 | Ferguson et al. |
| 7,585,072 B1 | 9/2009 | Wang-Lee |
| 7,594,280 B2 | 9/2009 | Lindahl |
| 7,648,233 B2 | 1/2010 | Blanshay et al. |
| 7,681,257 B1 * | 3/2010 | Broersma ......................... 2/425 |
| 7,686,449 B2 | 3/2010 | Jannard et al. |
| D616,485 S | 5/2010 | Thixton |
| 7,712,894 B2 | 5/2010 | Tsai |
| 7,712,896 B1 | 5/2010 | Lee |
| 7,725,959 B2 | 6/2010 | Wang-Lee |
| D622,303 S | 8/2010 | Thixton |
| 7,771,043 B2 | 8/2010 | Welchel et al. |
| 7,810,174 B2 | 10/2010 | Matera |
| D629,035 S | 12/2010 | Moritz |
| 7,850,301 B2 | 12/2010 | DiChiara |
| 7,856,673 B2 | 12/2010 | Reed |
| 7,887,181 B1 | 2/2011 | Chen |
| 7,954,942 B2 | 6/2011 | Calilung et al. |
| D659,180 S | 5/2012 | Moritz |
| 8,192,015 B2 | 6/2012 | Taylor et al. |
| 8,316,470 B2 | 11/2012 | McNeal et al. |
| 8,408,695 B2 | 4/2013 | Calilung et al. |
| 8,414,119 B2 | 4/2013 | Yeh |
| 2002/0039928 A1 | 4/2002 | Spurgeon et al. |
| 2004/0141147 A1 | 7/2004 | Cyr |
| 2005/0070434 A1 | 3/2005 | Drake |
| 2005/0132478 A1 | 6/2005 | Canavan |
| 2005/0270477 A1 | 12/2005 | Curci et al. |
| 2006/0048289 A1 | 3/2006 | Shiue |
| 2006/0119790 A1 | 6/2006 | Tsai |
| 2006/0179554 A1 | 8/2006 | Barton |
| 2006/0191062 A1 | 8/2006 | Matera |
| 2006/0250571 A1 | 11/2006 | Li |
| 2006/0256281 A1 | 11/2006 | Li |
| 2006/0283555 A1 | 12/2006 | Green |
| 2007/0024806 A1 | 2/2007 | Blanshay et al. |
| 2007/0033718 A1 | 2/2007 | Lin |
| 2007/0109490 A1 | 5/2007 | Collier et al. |
| 2007/0121059 A1 | 5/2007 | Chiou |
| 2007/0153230 A1 | 7/2007 | Musal et al. |
| 2007/0200997 A1 | 8/2007 | Jannard et al. |
| 2007/0240812 A1 | 10/2007 | Bortolato |
| 2007/0261782 A1 | 11/2007 | Frye et al. |
| 2008/0036961 A1 | 2/2008 | Zhou |
| 2008/0072365 A1 | 3/2008 | Alberto |
| 2008/0137028 A1 | 6/2008 | Webb |
| 2008/0155736 A1 | 7/2008 | Paulson et al. |
| 2008/0198323 A1 | 8/2008 | Siu |
| 2008/0266515 A1 | 10/2008 | Hou |
| 2008/0301858 A1 | 12/2008 | Wang-Lee |
| 2008/0304005 A1 | 12/2008 | DiChiara |
| 2009/0019620 A1 | 1/2009 | Reed |
| 2009/0038057 A1 | 2/2009 | Tews |
| 2009/0038059 A1 | 2/2009 | McNeal et al. |
| 2009/0217444 A1 | 9/2009 | Pan |
| 2009/0300830 A1 | 12/2009 | Mage |
| 2009/0313746 A1 | 12/2009 | Wang |
| 2010/0085533 A1 | 4/2010 | Calilung et al. |
| 2010/0186153 A1 | 7/2010 | Reyes et al. |
| 2010/0231850 A1 | 9/2010 | Hones |
| 2011/0007262 A1 | 1/2011 | Taylor et al. |
| 2011/0194065 A1 | 8/2011 | Belbey et al. |
| 2011/0225709 A1 | 9/2011 | Saylor et al. |
| 2011/0225710 A1 | 9/2011 | Reyes et al. |
| 2011/0225711 A1 | 9/2011 | Reyes et al. |
| 2011/0258758 A1 | 10/2011 | Renaud-Goud et al. |
| 2011/0299026 A1 | 12/2011 | Calilung et al. |
| 2012/0038879 A1 | 2/2012 | Reyes et al. |
| 2012/0218504 A1 | 8/2012 | Taylor et al. |
| 2012/0218507 A1 | 8/2012 | Calilung et al. |
| 2012/0255104 A1 | 10/2012 | Didier |
| 2013/0083285 A1 | 4/2013 | McNeal et al. |
| 2013/0104300 A1 | 5/2013 | Park |

FOREIGN PATENT DOCUMENTS

| | | |
|---|---|---|
| EP | 1830221 | 9/2007 |
| FR | 1126329 | 11/1956 |
| FR | 2088866 | 1/1972 |
| FR | 2626683 | 8/1989 |
| FR | 2688322 | 12/1992 |
| FR | 2684292 | 6/1993 |
| FR | 2 800 173 | 4/2001 |
| GB | 512419 | 9/1939 |
| GB | 2199155 | 6/1988 |
| GB | 2278459 | 11/1994 |
| JP | 219021 | 2/1990 |
| WO | WO 98/30930 | 7/1998 |
| WO | WO 2007/049070 | 5/2007 |

OTHER PUBLICATIONS

U.S. Appl. No. 29/383,475, filed Jan. 18, 2011, Taylor.
U.S. Appl. No. 29/383,464, filed Jan. 18, 2011, Taylor.
U.S. Appl. No. 13/051,896, filed Mar. 18, 2011, Reyes, et al.
U.S. Appl. No. 13/051,889, filed Mar. 18, 2011, Reyes, et al.
Invitation to Pay Additional Fees and, Where Applicable, Protest Fee received in corresponding International Application No. PCT/US2011/029080, mailed May 30, 3011 in 7 pages.
International Search Report and Written Opinion in corresponding International Application No. PCT/US2011/029080, mailed Aug. 18, 2011 in 17 pages.
U.S. Appl. No. 12/497,632, filed Jul. 3, 2009, Oakly.
U.S. Appl. No. 13/154,209, filed Jun. 6, 2011, Oakly.
U.S. Appl. No. 12/648,232, filed Dec. 28, 2009, Oakly.
U.S. Appl. No. 13/020,747, filed Feb. 3, 2011, Oakly.
U.S. Appl. No. 13/051,896, filed Mar. 18, 2011, Oakly.
U.S. Appl. No. 13/051,889, filed Mar. 18, 2011, Oakly.
U.S. Appl. No. 13/209,039, filed Aug. 12, 2011, Oakly.
U.S. Appl. No. 29/370,551, filed Aug. 3, 2010, Oakly.
U.S. Appl. No. 13/051,913, filed Mar. 18, 2011, Oakly.
International Preliminary Search Report and Written Opinion in corresponding International Application No. PCT/US2011/029080, issued Sep. 25, 2012 in 10 pages.

* cited by examiner

EYEWEAR WITH RIGID LENS SUPPORT

CROSS-REFERENCE TO RELATED APPLICATIONS

This application is a continuation of U.S. application Ser. No. 13/051,889, filed on Mar. 18, 2011, which claims the benefit of U.S. Provisional Application No. 61/315,752, filed Mar. 19, 2010 and U.S. Provisional Application No. 61/426,222, filed Dec. 22, 2010, the entirety of each of which is incorporated herein by reference.

BACKGROUND

1. Field of the Inventions

The present inventions relate generally to eyewear and more specifically to eyeglass and goggle frames, having improved comfort and fit.

2. Description of the Related Art

A wide variety of improvements have been made in recent years in the eyewear field, particularly with respect to eyewear intended for use in active sports, including goggles and sunglasses. These improvements have been incorporated into eyewear and goggles having both dual and unitary lens designs. As a result, modern active sport eyewear is functionally superior to its predecessor eyewear in numerous ways, such as by maximizing interception of peripheral light, reducing optical distortion, and increasing the wearer's comfort level.

For example, lens designs for both dual and unitary eyewear and goggle designs can provide full side-to-side range of vision and good lateral eye protection while providing superior optical performance. More particularly, in a unitary lens system, the angle of incidence from the wearer's eye to the posterior lens surface changes as the wearer's line of sight turns in either the vertical or the horizontal planes. This results in disparate refraction between light entering closer to the front of the lens and peripheral light entering at the side portions. To address this source of prismatic distortion, U.S. Pat. No. 4,859,048 discloses tapering the thickness of the lens from the central portion toward the side edge, the entirety of the disclosure of which is incorporated by reference herein.

Further, various improvements have also been made in goggle lens frame technology that allow mounted lenses to retain their superior optical characteristics provided by their as-molded geometry. For example, the "SPLICE" snow goggle manufactured by Oakley, Inc., incorporates a frame design that mitigates bending stresses along the bridge of the goggle in order to allow the lens to retain its as-molded geometry and maximize the comfort for the wearer. Such systems are disclosed in U.S. patent application Ser. No. 12/359,175, titled Controlled Deflection Goggle, filed Jan. 23, 2009, the entire disclosure of which is incorporated herein by reference.

Finally, numerous modifications have been made to eyeglass and goggle products in an effort to make these products more comfortable for the wearer. For example, different materials have been used in the manufacture of frames and lenses in order to decrease the weight and improve the comfort of these products. These technological improvements can be incorporated into any variety of dual or unitary lens designs, whether for eyeglass or goggle products, in order to provide a wearer with a comfortable, optically superior eyewear product.

Further features and advantages of the present invention will become apparent to those of skill in the art in view of the detailed description of preferred embodiments which follows, when considered together with the attached drawings and claims.

SUMMARY

A goggle is a semi-customizable eyewear product that can be adjusted to fit a wearer's head by adjusting a strap of the goggle. Further, an eyeglass can also be customized to the wearer through adjusting the fit and/or components of the eyeglass for achieving a desired function. Goggle and eyeglass applications include skiing, snowboarding, motocross, aquatics, and a variety of industrial safety applications, among others. Typically, goggles offer sealed protection to the eyes and adjacent areas of the wearer's face against particulate matter or water. Generally, the goggle and/or lens conforms closely to the wearer's face and intercepts light, wind, dust, etc. from directly in front of the wearer and peripherally along the sides. A wearer can adjust the elastic strap of the goggle to conform closely to the face of the wearer during use. Various features and structures of eyewear are disclosed herein. Some of these features and structures are disclosed in the context of goggles. For sake of brevity, the embodiments and discussion will not generally be repeated with respect to eyeglasses. However, the discussion of a given feature of a goggle herein is contemplated as being applicable to eyeglasses as well.

A goggle usually comprises an arcuate unitary lens which extends across both of the wearer's right and left eye fields of view. The lens can be supported by a frame, which typically surrounds the lens. The lens and the frame are both configured with a downwardly concave indent or nosepiece opening for receiving the nose. The rear surface of the frame, normally covered with a foam component or other compressible material, is adapted to contact the wearer's face. Further, the elastic strap is connected to the opposing sides or ends of the frame so that the wearer can fit and wear the goggle on their head.

When worn, the surface of the foam component or other compressible material disposed at the rear of the goggle makes contact with the wearer's face. This wearer-contacting surface has a radius of curvature in the horizontal plane that is adapted to conform from side to side of the wearer's face. However, some embodiments reflect the realization that when the goggle is placed on a wearer with a "narrow" head, the tension from the straps extending around the back of the wearer's head can cause the sides of the goggle to bend inwardly toward a center thereof, thereby wrapping the goggle into a tighter radius of curvature to fit the wearer and distorting the optics of the goggle. Further, the central portion of the goggle can become substantially compressed against the wearer's forehead while a gap is formed between the sides of the goggle and the wearer's temples. Other poor fit or discomfort problems can occur when a goggle is placed on a wearer with a "wide" head or when the goggle is worn over a helmet.

Thus, some embodiments reflect the realization that the lens of a goggle can sometimes experience undesirable distortion when the goggle is fitted to a wearer's unique head profile. This distortion can sometimes cause discomfort for the wearer as well as inferior optical performance of the eyewear product. Various embodiments enable the eyewear product to exhibit enhanced structural properties in order to prevent discomfort and to maintain preferred optical characteristics of the eyewear product.

Further, some embodiments reflect the realization that a customizable goggle system can be far more effective and useful to a wearer than prior art goggles because a wearer's needs and preferences may change from time to time. Thus, in some embodiments, the goggle can comprise an interchangeable goggle and goggle system in which a lens support or anterior module can be interchangeably coupled with a faceplate or posterior module. In some embodiments, the goggle and goggle system can also comprise at least one connector that couples the anterior module to the posterior module. The components of such a goggle and system can be interchanged in order to create a goggle having desired optical and physical characteristics. For example, the wearer can interchange one or more components of the goggle in order vary the rake, internal air volume, articulation, lens configuration, fit, comfort, and other such optical and physical characteristics of the goggle.

Further, some of the embodiments reflect the realization that prior art goggles tend to create uneven pressure distribution across a variety of wearers' heads. Thus, in some embodiments, the goggle can be configured such that the posterior module of the goggle can articulate relative to the anterior module in order to self-adjust over a variety of unique facial contours and head sizes in order to provide a customized fit to the wearer. In some embodiments, the goggle can comprise an isostatic mechanism or suspension mechanism in which one or more connectors allow the posterior module to articulate with respect to the anterior module. For example, the posterior module can be coupled to the anterior module using any of a variety of connectors, such as wishbone connectors, straight links, expandable cells, pivotable couplings, rigid couplings, and the like.

Additionally, some of the embodiments reflect the realization that prior art goggles generally caused deflection of the lens when the goggle is fitted onto the head of the wearer. Accordingly, in some embodiments, the goggle can be configured such that the anterior module comprises a generally rigid component or portion such that bending stresses exerted on the anterior module are withstood when the goggle is being worn. Thus, the lens of the goggle can be maintained in its as-molded configuration when in use, thereby preserving the optical quality of the lens. In some embodiments, prismatic shift or other optical distortions are minimized when in use.

Furthermore, some of the embodiments reflect the realization that prior art goggles do not facilitate interchangeability of lenses absent a significant stress or force to remove or replace the lens. Thus, in some embodiments, the goggle can comprise an interchangeable lens mechanism that allows a lens to be interchanged with and retained by the goggle. For example, the anterior module of the goggle can comprise one or more pockets or clips that can operate to retain one or more of the edges or sides of the lens. The lens can be retained by the interchangeable lens mechanism such that the lens "floats" or is secured to the anterior module without being bended from its as-molded configuration. Thus, the optical qualities of the lens can be preserved.

One or more of the features discussed herein can be incorporated into embodiments of the goggles. As such, any variety of combinations of these features can be provided as will be apparent to one of skill in the art.

Moreover, in some embodiments, a goggle is provided that can comprise a lens support or anterior module and a faceplate or posterior module. The lens support can be adapted to support at least one lens in a wearer's field of view. The faceplate can be flexible and adapted to conform to the contours of a wearer's face. In some embodiments, the lens support or anterior module can be interchangeably connectable with the faceplate or posterior module to modify at least one physical characteristic of the goggle.

In some embodiments, the faceplate can be coupled to the lens support such that when the goggle is worn by the wearer, opposing ends of the flexible faceplate move in a direction opposite to a direction in which a central portion of the faceplate moves when a force is exerted on one of the opposing portions and the central portion of the faceplate. Further, in some embodiments, in response to a force, the opposing ends of the flexible faceplate can move away from the opposing ends of the lens support while a central portion of the faceplate moves toward a central portion of the lens support. Further, the side portions of the faceplate can move generally independently of each other.

Some embodiments can comprise a suspension assembly that can comprise one or more suspension members or connectors that interconnect the flexible faceplate with the lens support at respective suspension points. In some embodiments, the at least one connector can be interchangeable with the lens support and the faceplate.

For example, the suspension members can enable pivotable movement of the faceplate relative to the lens support at the respective suspension points to modify a contour of the faceplate relative to the contour of the wearer's face. The suspension members can be substantially incompressible. The suspension members can comprise one of a wishbone connector, a curved or straight link connector, an expandable cell connector, and other such components. One or more suspension members may also be positioned in a manner that allows rolling or a "seesaw" effect as it responds to pressure on the frame. The goggle can optionally comprise at least one elongate link member coupled to the faceplate adjacent to each of the respective suspension points. The link members can be coupled to the respective suspension members and to the faceplate for imparting rotation at a first part of the goggle to a second part of the goggle for moving the opposing ends of the faceplate in an opposite direction of the central portion thereof.

Further, the goggle can be optionally configured such that the suspension members comprise a pair of upper suspension members interconnecting an upper portion of the flexible faceplate with an upper portion of the lens support. The suspension members can also comprise a pair of lower suspension members interconnecting a lower portion of the flexible faceplate with a lower portion of the lens support. In such embodiments, the upper suspension members can be coupled to the faceplate and the lens support at locations generally symmetrically spaced from a center point or center line of the faceplate, such as adjacent to side portions thereof. Further, the lower suspension members can be coupled to the faceplate and the lens support at locations generally symmetrically spaced from a center point or center line of the faceplate, such as adjacent to side portions thereof.

Further in some embodiments, the goggle can optionally comprise at least one elongate link member coupled to the faceplate adjacent to each of the respective suspension points. The link members can be coupled to the respective suspension members and to the faceplate for imparting rotation at a first part of the goggle to a second part of the goggle for moving opposing ends of the faceplate in an opposite direction of the central portion thereof.

In embodiments comprising the suspension assembly, the goggle can optionally be configured with the suspension assembly coupling the flexible faceplate to the lens support such that movement of the central portion of the flexible faceplate toward the central portion of the lens support causes separation of the opposing portions of the faceplate from opposing portions of the lens support when the goggle is worn by the wearer. In such embodiments, the suspension assembly can comprise one or more suspension members.

Moreover, some embodiments of the goggle can be configured to comprise a generally rigid lens support or anterior module. The generally rigid lens support or anterior module can support a lens in the wearer's field of view while preventing substantial bending or optical distortion of the lens.

Additionally, the goggle can optionally comprise an interchangeable lens mechanism that facilitates removal and retention of a lens relative to the lens support or anterior module of the goggle. The interchangeable lens mechanism can comprise one or more pockets and/or clips that can engage with a portion of the lens for retaining the lens relative to the goggle.

In some embodiments, the goggle can comprise a pair of outriggers that each outrigger comprises a pair of fastening portions configured to interconnect the anterior module with the posterior module. The fastening portions can be attachable to the anterior and posterior modules at coupling regions thereof. The anterior and posterior modules of the goggle can be coupled together by the outriggers and without the use of specialized tools, single-use fasteners or permanent fasteners. In some embodiments, the outriggers can function as the primary mode of coupling or attachment means between the anterior and posterior modules, such as between a lens support and a faceplate. However, a secondary mode of coupling or attachment means can be employed, such as snap-fit members, hook and loop members, and/or other types of interference fit or frictional engagement members. These secondary connectors can be used in combination with the outriggers to couple the anterior and posterior modules together. In particular, these secondary connectors can be used as an initial coupling mechanism to hold the anterior and posterior modules together as an assembly while the outriggers are attached or detached from the assembly. Thus, the overall assembly, including the outriggers and other components discussed herein, can enable a wearer to quickly manipulate an interchange any given component of the assembly.

Further, the outriggers can each further comprise a pin member extending from a body thereof. In such an embodiment, the anterior module can comprise a pair of apertures that are configured to receive the pin members of the respective outriggers when the outriggers are coupled to the anterior and posterior modules. The combined interconnections of the pin members and the fastening portions of the outriggers can thus provide a fixed rotational position of each outrigger relative to the anterior module. Additionally, the posterior module can comprise apertures configured to receive the pin member when the outriggers are coupled to the anterior and posterior modules. In some embodiments, the coupling regions of the anterior module comprise a recess. For example, the recess can be configured to receive the fastening portions of the outriggers.

Some embodiments of the goggle can comprise a latch member that is coupled to the anterior module. The latch member can be rotatable between an open position in which a lens can be inserted or removed from the lens support and a closed position in which the lens is secured to the lens support. The goggle can also further comprise a biasing member coupled to the latch member. The biasing member can provide a biasing force tending to urge the latch member toward the closed position. The biasing member can be rotatably coupled to the latch member, and in some embodiments, the biasing member can also be rotatably coupled to the anterior module. Thus, in some embodiments, an outrigger can comprises a pin member extending through corresponding apertures in the biasing member and the latch member, and the pin member can provide an axis of rotation for the biasing member and the latch member.

In accordance with some embodiments, the goggle can comprise at least one port disposed along the periphery of the lens support. The port can provide an airflow passage for introducing air over an interconnecting portion of the goggle for improving ventilation and reducing fogging of the goggle. For example, the port can exhibit Venturi airflow characteristics. In some embodiments, the goggle can comprise a pair of ports disposed at the central portion of the lens support above the lens of the goggle.

BRIEF DESCRIPTION OF THE DRAWINGS

The above-mentioned and other features of the inventions disclosed herein are described below with reference to the drawings of the preferred embodiments. The illustrated embodiments are intended to illustrate, but not to limit the inventions. The drawings contain the following figures.

DETAILED DESCRIPTION

While the present description sets forth specific details of various embodiments, it will be appreciated that the description is illustrative only and should not be construed in any way as limiting. Additionally, although particular embodiments of the present inventions may be disclosed or shown in the context of unitary or dual lens eyewear systems, such embodiments can be used in both unitary and dual lens eyewear systems. Further, various applications of such embodiments and modifications thereto, which may occur to those who are skilled in the art, are also encompassed by the general concepts described herein. Furthermore, although various embodiments are shown in use with goggles, embodiments can also be used with eyeglasses and other forms of eyewear.

Some goggle embodiments are provided that overcome many of the disadvantages of the prior art, such as preferential bending, poor comfort, and optical distortion of the lens. Various embodiments are provided that can improve the overall comfort and fit of the goggle on a wide range of head geometries. Some embodiments are configured such that the goggle can actively self-adjust to the head geometry of a given wearer using an isostatic suspension mechanism. Some embodiments are configured with a rigid lens support such that the goggle can prevent bending of the lens and thereby prevent optical distortion. Further, some embodiments can comprise a lens retention mechanism that enables a lens to be quickly removed and replaced with another given lens. Various mechanisms and features for providing one or more of these advantages can be incorporated into various embodiments of the goggle.

Prior Art Goggle Design and Use

Figure 1:
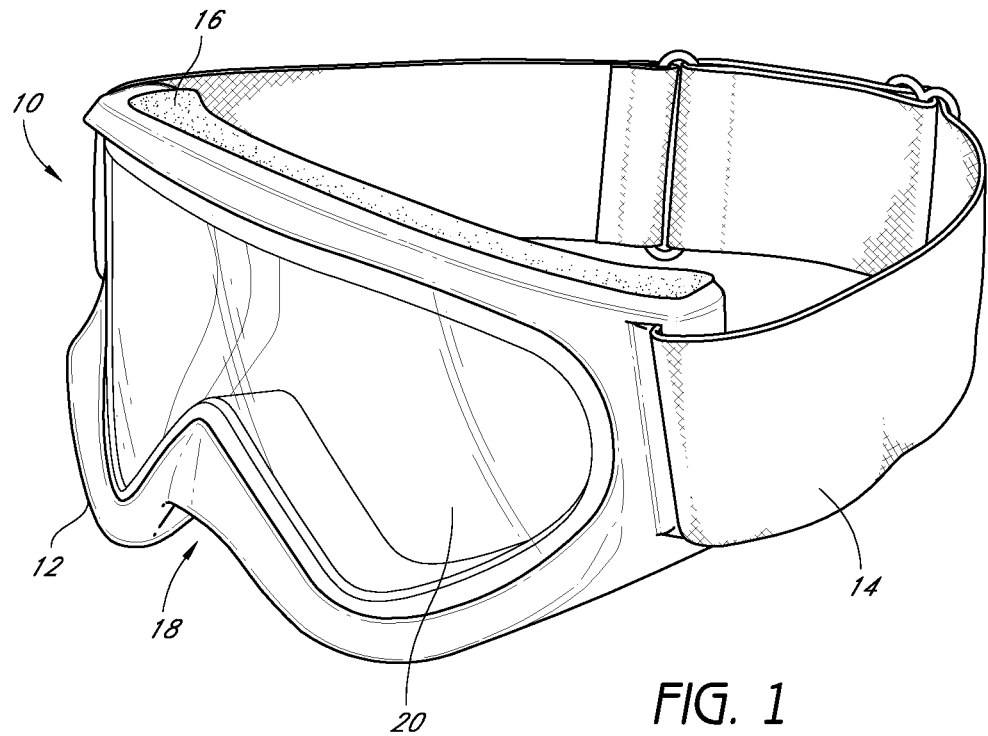
FIG. 1 is a perspective view of a prior art goggle.
Figure 3:
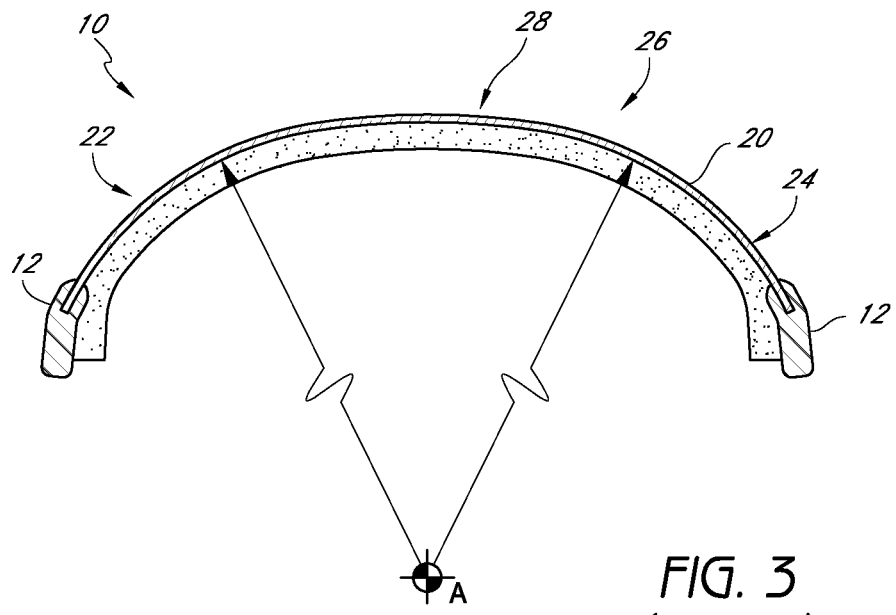
FIG. 3 is a horizontal cross-sectional view taken along the lines 3-3 of FIG. 2.
Figure 4:
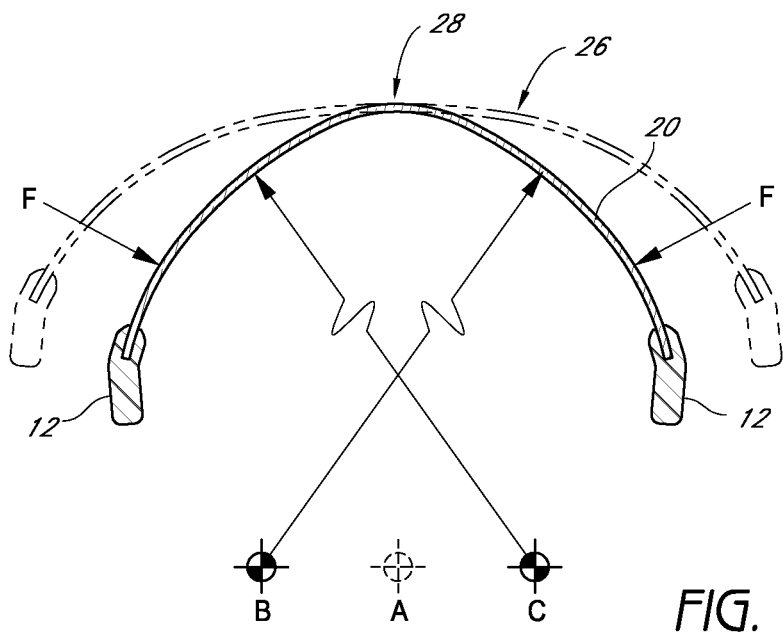
FIG. 4 is a top view of the goggle of FIG. 1 wherein bending forces F, F are exerted on the goggle.
Figure 5:
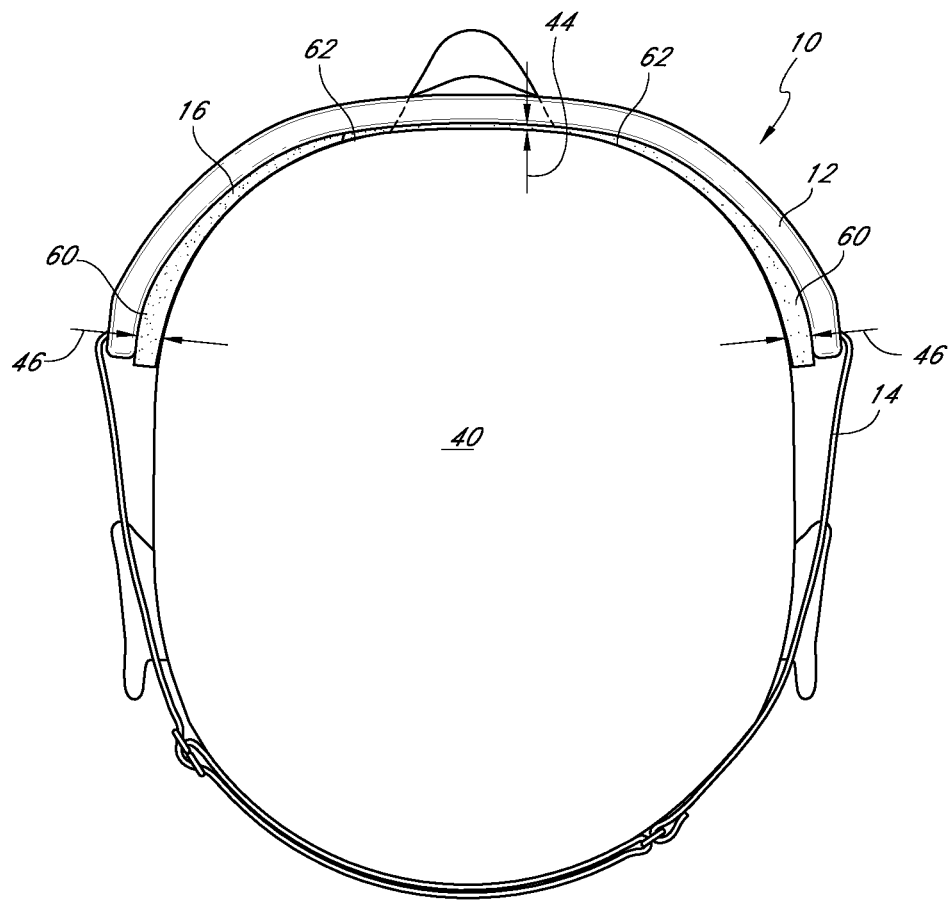
FIG. 5 is a top view of the goggle of FIG. 1 being worn on a narrow head.

FIGS. 1-5 illustrate a common prior art goggle design and its use. FIG. 1 illustrates a goggle 10 that comprises a goggle frame 12, an elastic strap 14, and a foam component 16 attached to a posterior portion of the goggle frame 12. The goggle frame 12 also comprises an indent or nosepiece 18. In use, the wearer can position the goggle frame 12 onto her face and adjust the elastic strap 14 around the back of her head in order to firmly, but comfortably secure the goggle frame in place. FIG. 5 illustrate a top view of a wearer's head 40 onto which the goggle 10 has been placed.

The foam component 16 is intended to contact the wearer's face and allow the goggle 10 to conform to the surface of the wearer's face. However, gaps frequently form between the foam component 16 and the surface of the wearer's face due to the preferential bending of the goggle 10. Furthermore, certain portions of the foam component 16 can often be highly compressed while other portions are not compressed at all. In this regard, the foam component 16 will fail to properly distribute stresses along the surface of the wearer's face resulting in stress concentrations along the front or side of the wearer's head, such as along the forehead, temples, and cheekbones. Some embodiments reflect the realization that such stress concentrations are created due to the preferential bending of the goggle frame 12 and the poor adaptability of the goggle frame 12 to various head sizes.

FIG. 3 illustrates a cross sectional top view of the goggle 10. As shown, a lens 20 of the goggle 10 is mounted in the goggle frame 12. FIG. 3 illustrates the goggle frame 12 and the lens 20 in an unloaded position. In some embodiments, the goggle frame 12 and the lens 20 are not bent from their as-molded configuration. As such, at least side portions 22, 24 of the lens 20 can be configured to define a common center of curvature A in this example. In the as-molded configuration, a central section 26 of the lens 20 defines a preferred geometry that can provide desirable optical characteristics for the goggle 10. However, these desirable optical characteristics are not maintained when the goggle 10 is worn by the user in a loaded position.

FIG. 4 shows the lens 20 of the goggle 10 in the loaded position. The loaded position is generally assumed when the goggle 10 is positioned on the head of the wearer. As illustrated in FIG. 4, bending forces F, F can be exerted on the sides of the frame 12 and cause bending of the frame 12 and the lens 20. These forces F, F can be caused by the elastic strap 14 during use of the goggle 10 by the wearer.

Figure 2:
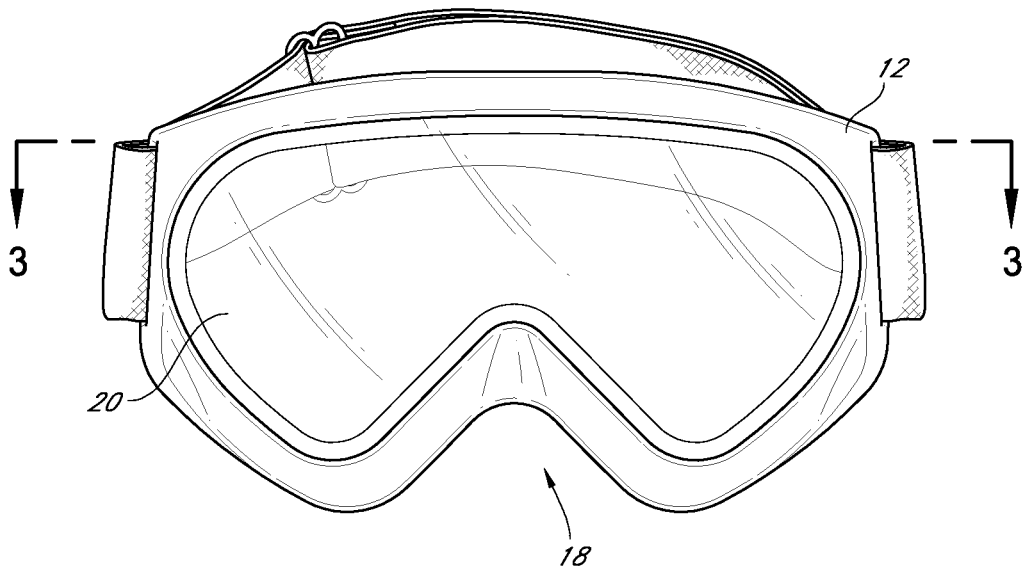
FIG. 2 is a front view of the goggle shown in FIG. 1.

When the goggle frame 12 and the lens 20 are bended to the loaded position, the goggles 10 generally exhibit preferential bending at a midpoint 28 of the lens 20. Some embodiments reflect the realization that a disadvantage of such preferential bending at the midpoint 28 of the lens 20 creates bending of the frame 12 at the nosepiece 18. As shown in FIG. 2, the nosepiece 18 has an unloaded geometry that defines a given width. Generally, the nosepiece 18 allows the wearer to comfortably position the goggle 10 on the bridge of the wearer's nose. However, preferential bending of the frame 12 will generally cause the width of the nosepiece 18 to decrease. As a result, the wearer's nose may be pinched and create discomfort for the wearer.

Additionally, the preferential bending also causes the centers of curvature of the side portions 22, 24 of the lens 20 to be significantly displaced from the common center of curvature A to the displaced centers of curvature B, C. The central section 26 of the lens 20 is also significantly deformed from its unloaded position. This deformation of the lens 20 substantially worsens the original or as-molded optical characteristics of the lens 20.

For example, the lens 20 can exhibit substantial prismatic shift and other optical distortions that tend to tire the eyes of the wearer and reduce the wearer's ability to accurately perceive the position of objects. These disadvantages may not only make use of the goggle 10 uncomfortable, but can potentially affect the wearer's performance of a given activity. In fast-paced activities, such as skiing, snowboarding, skydiving, motocross and the like, where goggles are commonly used, the disadvantages caused by preferential bending of the lens 20 and the frame 12 can be exacerbated.

Figure 6:
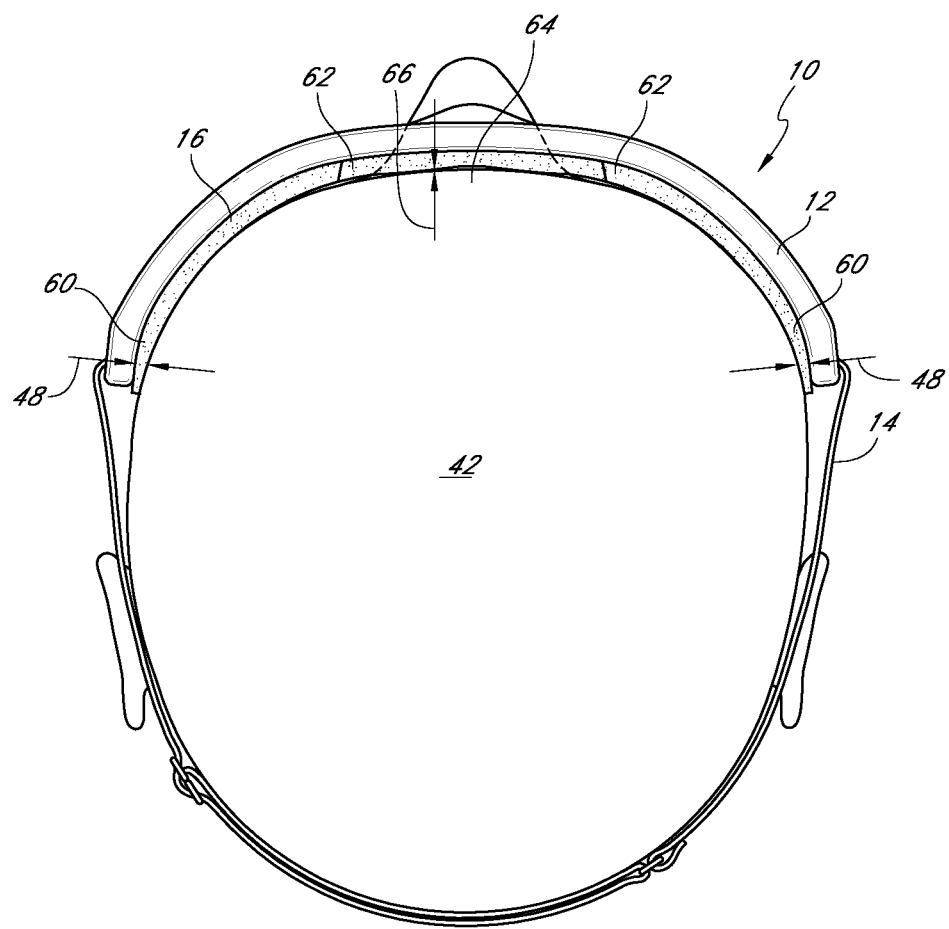
FIG. 6 is a top view of the goggle of FIG. 1 being worn on a wide head.

FIGS. 5-6 illustrate yet other disadvantages of such a prior art goggle 10. The top view of FIG. 5 shows a goggle 10 fitted onto a narrow head 40, and FIG. 6 shows the goggle 10 fitted onto a wide head 42. When fitted on a narrow head 40, the goggle 10 can bend about a central section thereof, thus resulting in deformation of the lens and various significant disadvantages, such as those noted above with regard to FIG. 3. Further, centralized portions 62 of the foam component 16 can experience greater compression 44 than side portions 60, which may be generally uncompressed as indicated at 46. Because the wearer has a narrow head, a gap may be created between the sides of the wearer's head and side portions 60 of the goggle 10 as the goggle 10 is fitted against the wearer's head. This uneven fit can reduce the air volume within the goggle in the central section, which may reduce the anti-fogging effectiveness of the goggle 10. The uneven fit may also cause uneven pressure and discomfort against the head 40 of the wearer.

With regard to FIG. 6, when fitted on a wide head 42, the goggle may again experience bending of the lens 20 (albeit toward a larger radius of curvature, which still results in optical distortion). Further, due to the preferential bending of the goggle 10, the foam component 16 can often experience excessive compression 48 along side portions 60 of the foam component 16. Additionally, centralized portions 62 of the foam component 16 may actually be separated from the wearer's forehead 64 by a gap 66. Although the gap 66 may be minor, such gapping can be problematic in inclement weather or water-related applications, as may be present in skiing and scuba diving. In such applications, gapping can cause impaired vision. Further, the uneven compression of the foam component 16 can create uneven pressure and discomfort against the head 42 of the wearer. As a result, the wearer can generally experience greater discomfort and fatigue.

Interchangeable Component Goggle Embodiments

Some embodiments reflect the realization that in many situations, the goggle 10 may bend as it is fitted onto a wearer's head, thus resulting in deformation of the lens 20, a poor fit that creates uneven pressure and discomfort across the wearer's head, and/or reduced anti-fogging capabilities. Additionally, some embodiments reflect the realization that the orientation of the goggle 10 with respect to the wearer's line of sight may be difficult to precisely adjust. Thus, the wearer may be at a disadvantage in performing activities in which vision could be enhanced by precisely adjusting the orientation of the lens (such as the "rake" of the lens).

Accordingly, some embodiments provide a manner for improving the comfort, fit, optical quality, anti-fogging, and/or customization and interchangeability of components of a goggle. Some embodiments can provide a goggle that includes an anterior module or lens support that can be interchanged with a posterior module. For example, one or more anterior modules (or lens supports) can be interchangeable with one or more posterior modules (or faceplates, which can be fitted against the face of a wearer).

Some embodiments can provide a goggle that includes an isostatic faceplate configured to provide uniform pressure distribution of the face-contacting portion of the goggle against the face of the wearer across a range of head sizes. Such embodiments can mitigate uneven pressure distribution by allowing differential adjustability of a posterior module relative to an anterior module of the goggle.

Some embodiments can also provide a goggle in which the anterior module or lens support is operative to support the lens of the goggle in an undeflected or optically preferred orientation to optimize the optical qualities of the lens. For example, at least a portion of the anterior module or lens support can be substantially rigid to prevent bending of the lens. Further, some embodiments can provide a goggle at having a quick release lens mechanism.

These and other features can be incorporated into a single goggle or used independently of each other to provide for a plurality of distinct goggle embodiments.

Some embodiments of the goggle can comprise separable components that can be interchangeably used in order to customize the goggle to the wearer's preferences. In some embodiments, the goggle can comprise separable components that can be interchangeably used to modify a mechanical and/or cosmetic feature of the goggle.

For example, separable components can be interchangeably used to modify at least one of the "rake" of the lens, the enclosed air volume capacity within the goggle, structural relationship between the anterior module and the posterior module, the articulation between the anterior module and the posterior module, the biasing of the posterior module, the fit of the goggle, and other mechanical and/or cosmetic features.

FIGS. 7-12 show an embodiment of a goggle 100. The goggle 100 can comprise a lens support or anterior module 102, a posterior module 104, and at least one connector 106 extending between the anterior module 102 and the posterior module. The anterior module 102 can support a lens in the wearer's field of view. In some embodiments, the anterior module 102 can be flexible. However, in some embodiments, the anterior module 102 can comprise at least one substantially rigid component and/or frame that supports or maintains the lens in a manner that prevents distortion of the lens under normal use conditions.

Figure 7:
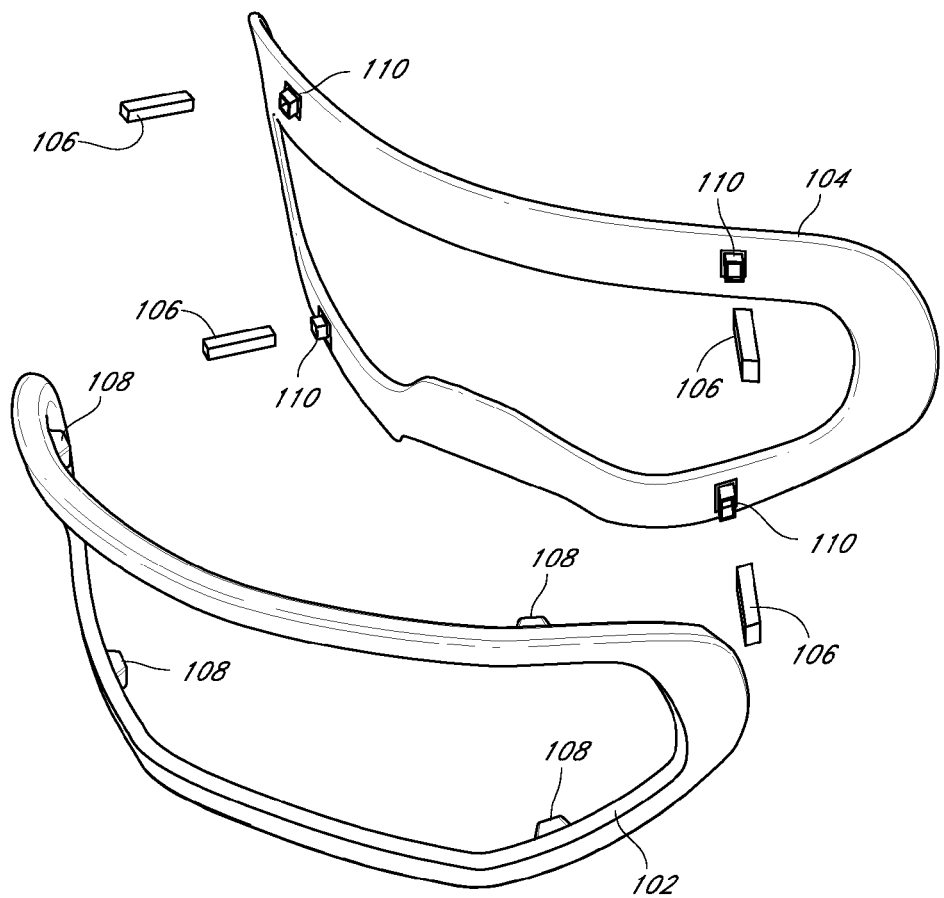
FIG. 7 is an exploded perspective view of a goggle having interchangeable anterior and posterior components, according to an embodiment.
Figure 8:
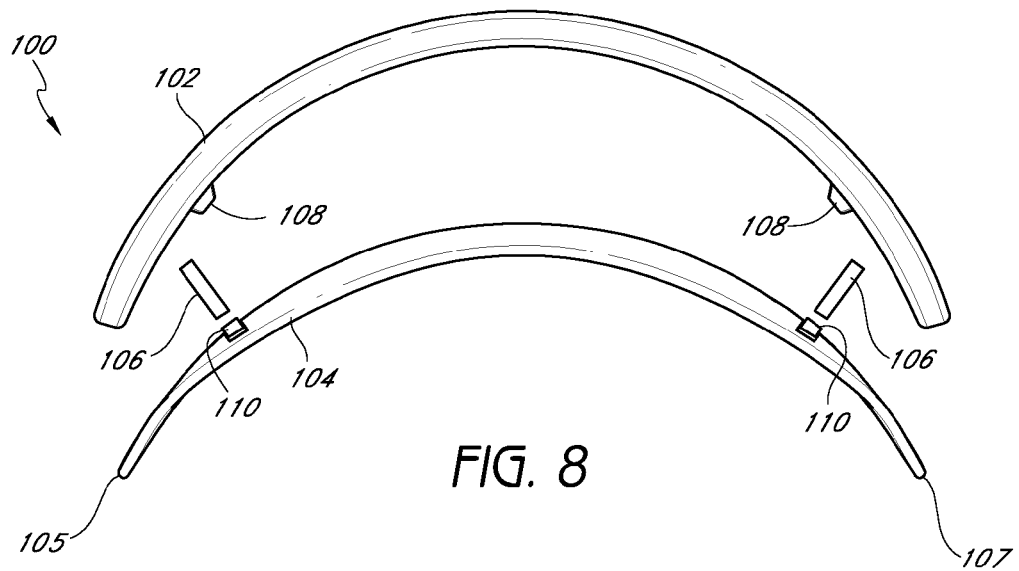
FIG. 8 is a top view of the goggle shown in FIG. 7.
Figure 9:
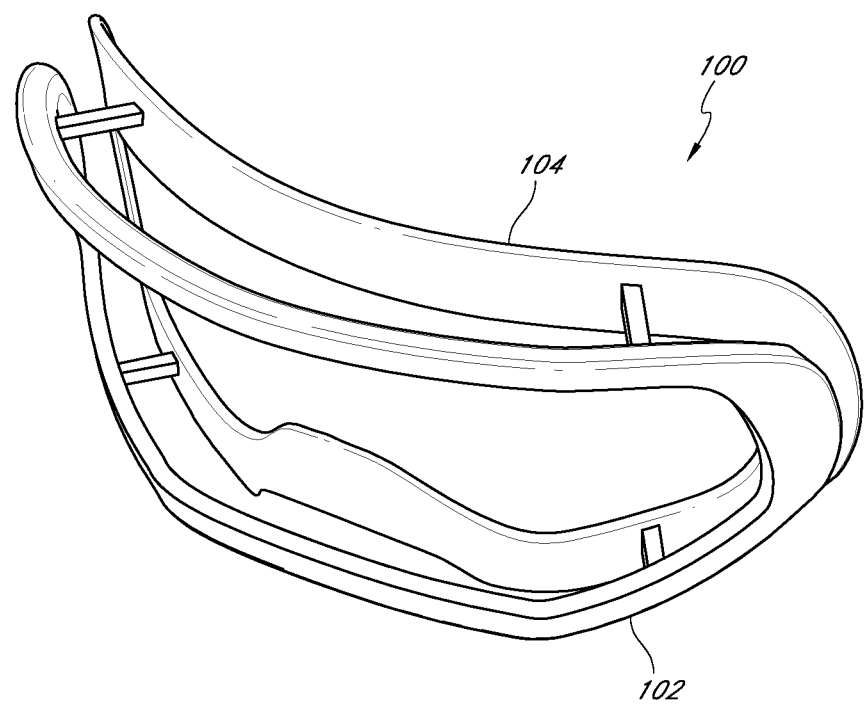
FIG. 9 is a perspective view of a goggle having interchangeable anterior and posterior components shown in an assembled state, according to an embodiment.
Figure 10:
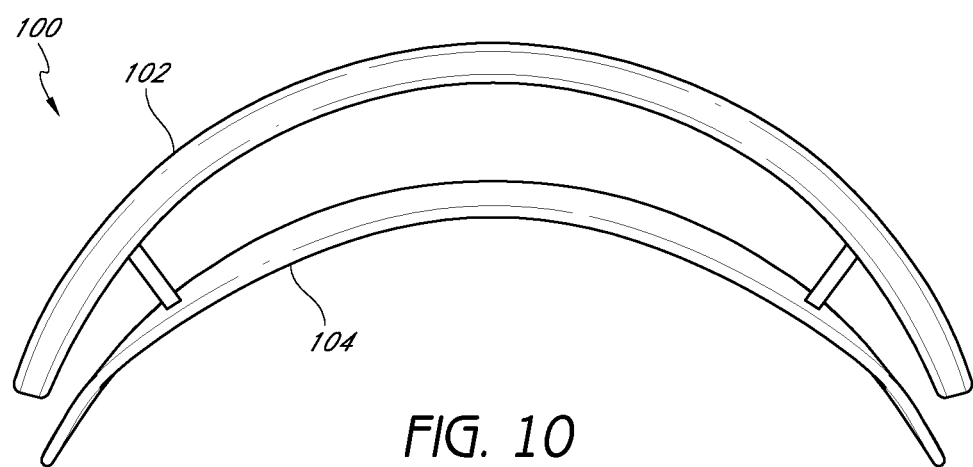
FIG. 10 is a top view of the goggle shown in FIG. 9.
Figure 11:
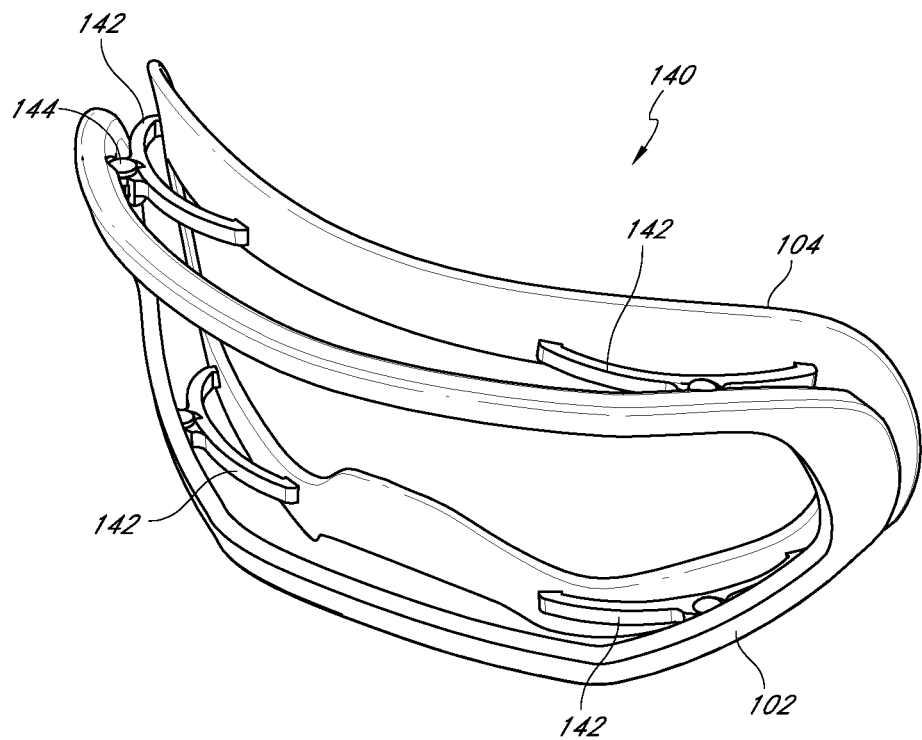
FIG. 11 is a perspective view of another goggle having interchangeable anterior and posterior components shown in an assembled state, according to another embodiment.
Figure 12:
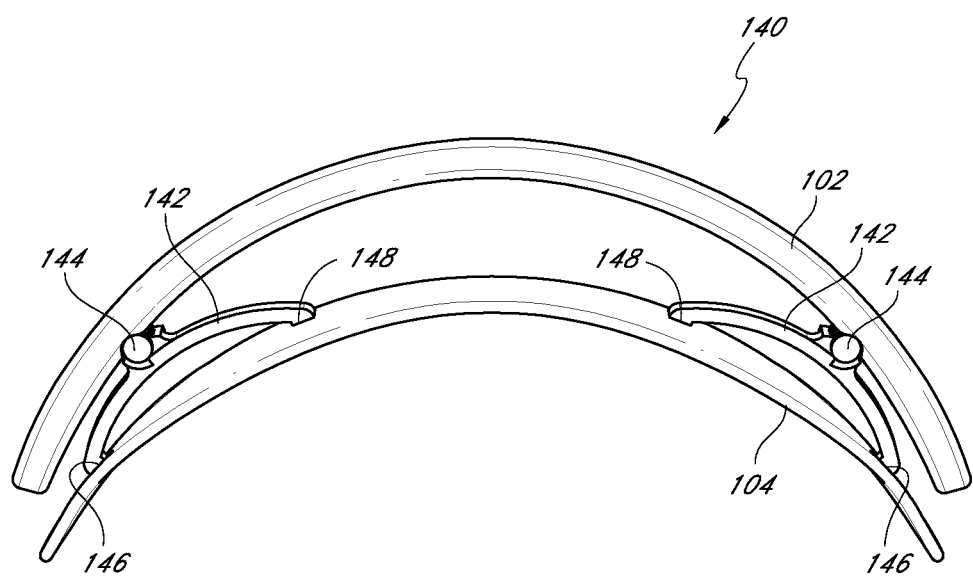
FIG. 12 is a top view of the goggle shown in FIG. 11.
Figure 13:
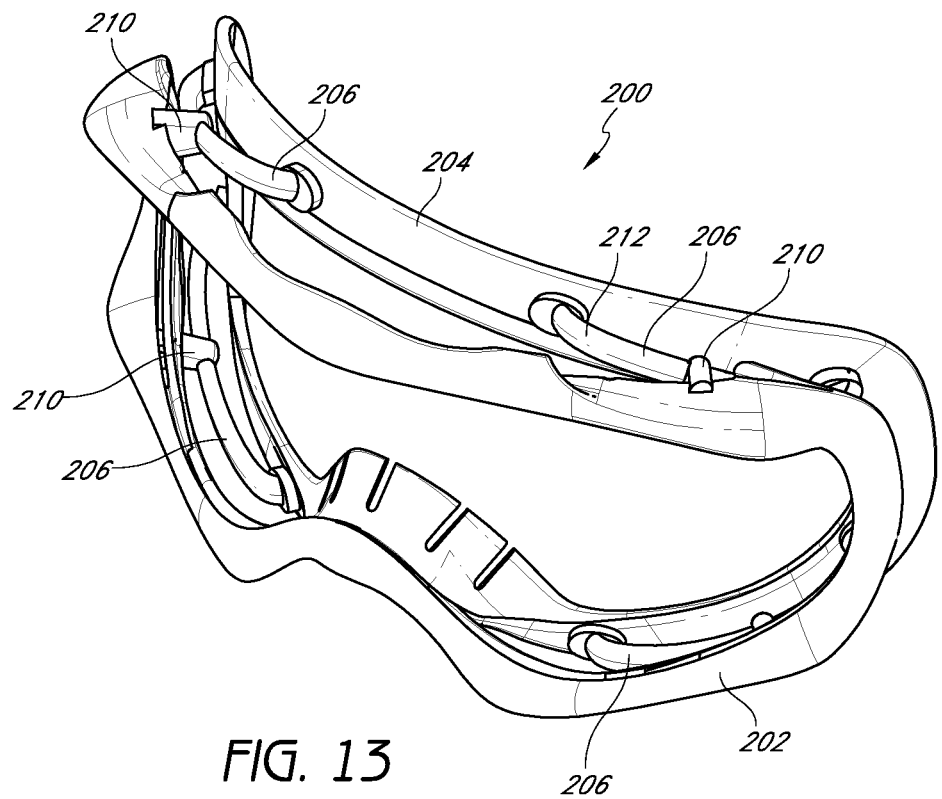
FIG. 13 is a top perspective view of a goggle having an isostatic faceplate with flexible connectors, according to an embodiment.
Figure 14:
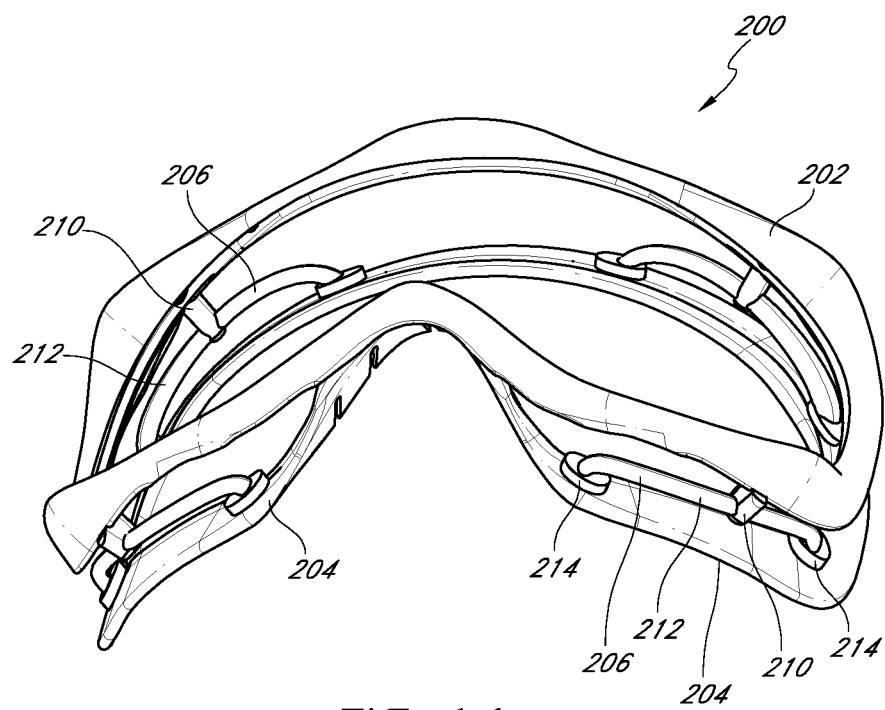
FIG. 14 is a bottom perspective view of the goggle shown in FIG. 13.

FIGS. 7 and 8 illustrate the goggle 100 in a disassembled state, and FIGS. 9-10 illustrate the goggle 100 in an assembled state wherein the connector(s) 106 is coupled with the anterior module 102 and the posterior module 104. FIGS. 11-12 illustrate another embodiment of a goggle in an assembled state wherein a different embodiment of the connector(s) 106 is coupled with an anterior module 102 and a posterior module 104.

The components of the goggle can be interchangeable or replaceable with other components. The posterior module 104 can be configured to be interchangeable and removably attachable to the anterior module 102. One or more anterior modules 102 can be interchanged with a plurality of posterior modules 104 in order to provide a variable and customizable configuration depending on user preferences. Further, a common anterior module 102 can be interchangeable with one of a variety of posterior modules 104. For example, the goggle 100 can be configured such that the wearer can interchange components of the goggle 100 in order to adjust the goggle 100 to modify a fit between the anterior module 102 and the posterior module 104, a configuration of the anterior module 102 and/or the posterior module 104, and/or an interconnection between the anterior module 102 and the posterior module 104.

As noted above, the goggle 100 can comprise the connector(s) 106. The connector(s) 106 can releasably or permanently couple the anterior module 102 with the posterior module 104. The connector(s) 106 can comprise either a movable or fixed component that interconnects the anterior module 102 with the posterior module 104. The connector(s) 106 can extend partially or completely around a perimeter of the anterior module 102 and/or the posterior module 104.

The configuration of the connector(s) 106 can be modified or interchanged to directly influence the fit between the anterior and posterior modules and/or the manner in which the posterior module and/or the anterior module functions in the goggle. The configuration of the connector(s) 106 may be varied while the configuration of the posterior and/or anterior module remains constant. In some embodiments, both the configuration of the connector(s) 106 and the configuration of the posterior and/or anterior module can be varied. The connector(s) 106 can also be configured in a variety of different connection modes and purposes. Thus, in this and other embodiments disclosed and discussed further herein, the movement of the posterior module can be performed substantially independently of movement of the anterior module. Thus, in embodiments, the posterior module may flex and be shaped to the face of the wearer to maximize comfort and fit while the anterior module is maintained in a substantially undeflected state, thus avoiding optical distortion of a lens (whether dual or unitary) supported by the anterior module.

For example, the connector(s) 106 can be configured to provide a rigid, stationary, or fixed relationship between the connector(s) 106 and the anterior and/or posterior modules 102, 104. In such embodiments, the connector(s) 106 can establish a spacing, position, or orientation of the posterior module 104 relative to the anterior module 102. Further, the connector(s) 106 can be interchanged to modify the spacing, position, or orientational relationship between the anterior and posterior modules 102, 104.

Further, in some embodiments, the connector(s) 106 can also be configured to provide a flexible, movable, rotatable, translatable, or pivotable relationship between the connector(s) 106 and the anterior and/or posterior modules 102, 104. For example, the connector(s) 106 can be coupled to the anterior module 102 and to the posterior module 104 in a manner that allows the connector(s) 106 to move or rotate relative to at least one of the anterior module 102 and the posterior module 104. In this manner, the connector(s) 106 can enable the posterior module 104 to flex, move, rotate, translate, or pivot relative to at least one of the anterior module 102. In this manner, the goggle 100 can provide an independent suspension or isostatic mechanism that can equalize or evenly distribute the pressure of the goggle along and against the areas at which the goggle contacts the face of the wearer. The independent suspension or isostatic mechanism can provide differential adjustability of the posterior module relative to the anterior module in order to equalize pressure distribution exerted by the posterior module against the head of the wearer.

Further, in some embodiments, the connector(s) 106 can be interchangeable with the goggle 100 in order to provide a different connection mode and/or a customizable configuration depending on wearer preferences. For example, different embodiments of the at least one connector(s) 106 can be interchanged with the goggle (such as shown in the embodiments shown in FIGS. 9-12).

The connector(s) 106 can be formed separately from the anterior and posterior modules 102, 104. The connector(s) 106 can be removable from the goggle and interchangeable in order to allow the wearer to adjust a given characteristic of the goggle. Further, the connector(s) 106 can be coupled to one of the posterior module 104 and anterior module 102 in a manner that allows relative movement between the connector(s) 106 and at least one of the posterior module 104 and the anterior module 102. In some embodiments, the ends of the connector(s) 106 can be attached to the anterior and/or posterior modules 102, 104 by means of thermal bonding, adhesive bonding, mechanical engagement, and/or other coupling methods known in the art. Various embodiments are shown in FIGS. 11-23E, which will be discussed further below.

However, in some embodiments, the connector(s) 106 can also be monolithically formed with either of the anterior or posterior modules 102, 104.

The connector(s) 106 can also comprise one or more sub-components, for example, that can articulate with respect to each other to provide an articulating connector(s) 106. Further, the connector(s) 106 can be formed from various types of materials, for example, to provide rigidity, flexibility, compressibility, or other desirable mechanical or material characteristics. Thus, the connector(s) 106 can comprise pivotable links, rigid links, flexible bodies, leaf springs, coil springs, rigid bodies, compressible bodies, rod-shaped bodies, wishbone-shaped bodies, diamond-shaped bodies, gaskets, and/or expandable cells.

In some embodiments, the goggle 100 can comprise a single connector 106. For example, a single connector 106 can be in the form of a gasket, pad, or other unitary structure that extends about the periphery of the anterior and posterior modules 102, 104 and interconnects the anterior and posterior modules 102, 104. Further, in some embodiments, the goggle can comprise multiple connectors 106.

As shown in FIGS. 7-10, in some embodiments, the connector(s) 106 can interconnect with respective anterior and posterior connection points 108, 110 located on the respective ones of the anterior and posterior modules 102, 104. The anterior and posterior connection points 108, 110 can provide a rigid, stationary, or fixed relationship between the connector(s) 106 and the anterior and/or posterior modules 102, 104 and/or a movable, rotatable, translatable, or pivotable relationship between the connector(s) 106 and the anterior and/or posterior modules 102, 104.

The anterior and posterior connection points 108, 110 can be formed in a variety of configurations. For example, in the illustrated embodiment of FIGS. 7-10, the anterior and posterior connection points 108, 110 can comprise a complementary surface structure such as a recess or socket that is configured to engage a corresponding surface structure on the connector(s) 106. Further, in some embodiments, the anterior and posterior connection points 108, 110 can comprise protrusions that extend rearwardly and anteriorly, respectively, which can be configured to engage with the connector(s) 106. Nevertheless, any of the anterior connection points and/or the posterior connection points can comprise a protrusion, recess, or socket for coupling with the connector(s).

In some embodiments, the configuration of the anterior and posterior connection points 108, 110 can be modified to directly influence the manner in which the connector(s), the posterior module, and/or the anterior module function in the goggle. In some embodiments, the configuration of the anterior and posterior connection points 108, 110 may be the only variable while the configuration of the posterior and/or anterior module remains constant. In some embodiments, both the configuration of the posterior and/or anterior connectors and the configuration of the posterior and/or anterior module can be varied.

Referring to FIG. 8, the faceplate or posterior module 104 of the goggle 100 can extend between a first lateral edge 105 and a second lateral edge 107. The direct line distance, in the nature of a secant to the curvature of the faceplate, will, in a properly fitting goggle, correspond to the width of the wearer's face at the point of contact between lateral edges 105 and 107, and the wearer's head. That secant length in an unstressed goggle will typically be within the range of between at least about 4 inches and/or less than or equal to about 7 inches. Often, the range can be between at least about 5½ and/or less than or equal to at least about 6½ inches. In accordance with some embodiments, the secant distance between lateral edges 105 and 107 may be varied by at least about 0.5 inches, and generally between at least about 1 inch and/or less than or equal to about 2 inches, without changing the curvature of the lens.

As discussed below, embodiments of a goggle system can be provided in which at least one of the anterior module 102, the posterior module 104, and/or the connector(s) 106 can be selectively interchangeable by the wearer to customize at least one of the characteristics of the goggle.

In some embodiments, the goggle system can comprise a plurality of components, connectors, anterior modules, and/or posterior modules having different geometric characteristics that can induce a desired "rake" in the goggle. For example, the goggle system can comprise a plurality of posterior modules 104 having different geometric characteristics that induce a desired "rake" in the goggle. The "rake" of the goggle generally refers to the orientation of the lens relative to a vertical line. An adjustment in the rake of the goggle can allow the wearer to adjust an optical centerline of the lens such that the optical centerline is displaced away from a normal straight-ahead line of sight toward an activity-specific line of sight of the wearer.

For example, some embodiments can allow the rake of the goggle to be customized for activities in which the wearer frequently gazes downwardly relative to the straight-ahead line of sight (to view the path immediately in front of the wearer) or upwardly relative to the wearer's straight-ahead line of sight. By adjusting the optical centerline to correspond more closely to the activity-specific line of sight, the wearer can minimize image shift or prismatic distortion that occurs when the wearer's gaze (i.e. the activity-specific line of sight) passes across the lens. This can be advantageous for sports that require quick reaction times and frequent monitoring of the terrain in front of the wearer, such as downhill skiing, snowboarding, motocross, and the like.

The rake of the goggle can be adjusted such that the optical centerline of the lens is approximately parallel with the activity-specific line of sight. Further, the rake of the goggle can be adjusted such that the optical centerline of the lens is approximately coaxial with the activity-specific line of sight.

Accordingly, in some embodiments, a posterior module can attach with an anterior module and position the lens from the wearer's head at a different vortex distance than that of another posterior module. In particular, different posterior modules can be interchanged to allow the wearer to induce a different rake in the goggle depending on which posterior module is used. Further, different connectors or anterior modules can also be interchanged to allow the wearer to induce a different rake or to otherwise affect the geometry or spacing of the goggle relative to the wearer's face. The difference in spacing or position can be created due to geometric properties of at least one of the posterior module, the anterior module, and/or connectors between the posterior module and the anterior module.

Some embodiments of the goggle system can comprise a plurality of components, connectors, anterior modules, and/or posterior modules that each result in different air volumes within the goggle in order to adjust the anti-fogging capabilities of the goggle. As will be appreciated, the larger the volume of air within the goggle, the lower the likelihood of fogging of the lens of the goggle under a given set of conditions.

For example, depending on the activity, a wearer may remove and replace a given posterior module with another posterior module that increases or decreases the volume of air trapped within the goggle between the lens and the wearer's face. In some embodiments, the connectors, anterior modules, and/or posterior modules can be configured to adjust the space between the anterior module and the wearer's face, such as by varying thickness of padding, thickness of the body of the posterior module, and/or varying the length and/or size of connector(s) used between the posterior module and the anterior module.

Further, the goggle system can comprise a plurality of different components, connectors, anterior modules, and/or posterior modules that can allow a wearer to select between various types of materials, material or mechanical properties, design features, and sizes. In some embodiments, the connectors or components can be formed to provide a minimal or low-profile goggle appearance. The connectors or components can be configured to provide a minimal overall goggle thickness.

For example, posterior modules can be provided in small, medium, large, and extra large sizes in order to allow a wearer to obtain a tailored to fit for their goggle. Each has dynamic conformability through a range of head sizes or geometries. In some embodiments, the posterior modules can be configured to provide biasing toward a desired default position, such as being biased inwardly (for narrow head sizes), outwardly (for wide head sizes), toward a center thereof, frustoconically, cylindrically, spherically, or toward a standard position (for average head sizes). Thus, a posterior module can be configured to assume an undeflected, biased position from which the posterior module can be deflected when the goggle it is positioned on the face of the wearer. The undeflected, biased position can be selected to improve the fit and conformance of the posterior module for a given head shape.

Further, the posterior modules can also be selected based on the thickness, width, material, and configuration of padding of the posterior module. Moreover, some embodiments can allow wearers to incorporate electronics, such as audio and telecommunication equipment, such as an MP3 player or cell phone into the goggle. For example, the anterior module, the posterior module, the strap, and/or other components of the goggle can support one or more electronic devices for use by the wearer. Thus, embodiments provide for an interchangeable goggle having superior customization and capabilities.

In addition to the interchangeability of the anterior and posterior modules in order to provide customizable geometries and configurations of the goggle, the connector(s) 106, the posterior connection point(s), and/or the anterior connection point(s) can also be modified to allow adjustment the rake, component size, air volume, and/or other characteristics of the goggle. In some embodiments, the size, shape, and/or configuration of the connector(s) 106, the posterior connection point(s), and/or the anterior connection point(s) can be selected in order to modify characteristics of the goggle, such as those discussed above. In some embodiments, at least one of the connector(s) 106, the posterior connection point(s), and/or the anterior connection point(s) can be interchanged in order to modify the rake, component size, air volume, and/or other characteristics of the goggle.

FIGS. 11-12 illustrate another embodiment of a goggle 140. While the goggle 140 can comprise a lens support or anterior module 102 and a posterior module 104, similar to the goggle 100 discussed above, the goggle 140 shown in FIGS. 11-12 can comprise a different embodiment of the connector(s) discussed above. In particular, the goggle 140 can comprise an arcuate wishbone connector 142. Various embodiments of the wishbone connector 142 are discussed and illustrated herein, for example, in FIGS. 11-27.

In some embodiments, the wishbone connector 142 can be coupled to the anterior module 102 and to the posterior module 104 in a manner that allows the wishbone connector 142 to move, flex or rotate relative to at least one of the anterior module 102 and the posterior module 104. The goggle 140 can provide differential adjustability of the posterior module relative to the anterior module in order to dynamically conform to the wearer's face and tend to equalize pressure distribution exerted by the posterior module against the head of the wearer.

The wishbone connector 142 can be coupled to the anterior module 102 at at least one point and to the posterior module 104 at at least one point. For example, in embodiments such as that illustrated in FIGS. 11-12, the wishbone connector 142 is coupled to the anterior module 102 at a single point and to the posterior module at two points. Such a construction can tend to encourage flexion of the posterior module 104 while the anterior module 102 remains generally undeflected. In such embodiments, the lens supported by the anterior module 102 may therefore be generally undeflected, thus resulting in improved optical performance of the goggle.

The wishbone connector 142 can be movably or rotatably coupled to at least one of the anterior module 102 and the posterior module 104. In order to provide a movable or rotatable relationship between the wishbone connector 142 and at least one of the anterior module 102 and the posterior module 104, wishbone connector 142 can comprise a flexible or pivotable joint formed at one of the connection points of the wishbone connector 142 and the anterior module 102 and/or the posterior module 104.

For example, the wishbone connector 142 can comprise a pivotable connection point 144. In some embodiments, the pivotable connection point 144 can be configured as a hinge joint or rotatable coupling formed between the wishbone connector 142 and the anterior module 102.

Further, the wishbone connector 142 can also comprise a flexible material that is used to create a flexible or pivotable joint. Such an embodiment is illustrated and discussed below with reference to FIGS. 13-16.

In the embodiment illustrated in FIGS. 11-12, the wishbone connector 142 is coupled to the posterior module 104 at first and second posterior connection points 146, 148. In some embodiments, the first and second posterior connection points 146, 148 provide a fixed, rigid, or stationary coupling between the wishbone connector 142 and the posterior module 104. However, the first and second posterior connection points 146, 148 can provide a movable, rotatable, or pivotable coupling between the wishbone connector 142 and the posterior module 104.

The wishbone connector 142 can be configured to impart a desired relative movement between the anterior module 102 and the posterior module 104. As discussed and shown further below with respect to FIGS. 21A-27, the size, shape, and coupling mode of the wishbone connector can be varied in order to achieve a desirable articulation of the posterior module 104 relative to the anterior module 102. For example, the movement of the posterior module 104 can be performed substantially independently of movement of the anterior module 102. These considerations and alterations can be made in order to enhance the fit of the goggle, to provide a customized articulating for a specific range of head sizes or activities, and/or to modify the goggle design. In some embodiments, this mechanism can serve to enhance the comfort and fit of the posterior module 104 while preserving the optical qualities of a lens supported by the anterior module 102.

The interchangeable goggle embodiments discussed above with respect to FIGS. 7-12 can incorporate various mechanisms and features discussed in greater detail below, and optionally, in an interchangeable system. Some of these features will now be discussed in greater detail with reference to specific embodiments. While the features discussed herein can be incorporated into one or more of the interchangeable goggle embodiments, the features discussed herein can also be incorporated into one or more goggle embodiments that do not provide an interchangeability of components as discussed above with respect to FIG. 7-12.

Isostatic Faceplate Goggle Embodiments

Many prior art goggle designs share the deficiency of allowing preferential bending at a midpoint of the goggle frame as the goggle is tightened on a wearer's head that is narrower than the unstressed lateral edge to edge dimension of the goggle. Such preferential bending creates an inferior fit, reduced optical quality, and may even cause physical and optical discomfort for the wearer. Therefore, some embodiments reflect the realization that the preferential bending of prior art goggle frames can be reduced and/or eliminated in order to enhance the comfort and performance of a goggle, such as that disclosed in copending U.S. patent application Ser. No. 12/359,175, filed on Jan. 23, 2009, titled Controlled Deflection Goggle, the entirety of which is incorporated herein by reference. In addition, some embodiments disclosed herein reflect the realization that a customized fit can be achieved by allowing portions of the goggle to dynamically articulate with respect to each other and actively adjust to contours of the wearer's face without requiring corresponding bending of the lens.

FIGS. 13-20 illustrate an isostatic faceplate mechanism that can be provided in accordance with some embodiments. As used herein, the term "isostatic faceplate mechanism" or "isostatic faceplate" can refer generally to a mechanism having an anterior module or frame and a posterior module or frame, wherein the posterior module can be adjustable relative to and/or independently of the anterior module to allow the posterior module to have a customized fit against the wearer's head. For example, this relative movement can further allow a desired shape of the anterior module to be maintained during flexing of the posterior module in order to prevent optical distortion of a lens or lenses supported by the anterior module. For example, in some embodiments, connectors between the anterior and posterior modules can allow a posterior module to articulate with respect to the anterior module to permit movement of the posterior module independently of movement of the anterior module. The posterior module can self-adjust to the shape and contour of the wearer's face, while maintaining the optical alignment of the lens contained in the anterior module.

As shown in FIGS. 13-16B, a goggle 200 can comprise a lens support or anterior module 202, a posterior module 204, and at least one connector 206. The isostatic faceplate mechanism of the goggle 200 can be formed using the connector(s) 206 and the anterior and posterior modules 202, 204. The isostatic faceplate mechanism can provide differential adjustability of the posterior module relative to the anterior module in order to equalize pressure distribution exerted by the posterior module against the head of the wearer.

In the embodiment illustrated in FIGS. 13-16B, the connector(s) 206 can comprise a flexible coupling 210 that couples the connector(s) 206 to the anterior module 202. In this manner, the flexible coupling 210 can allow the connector(s) 206 to be coupled to the anterior faceplate 202 while permitting relative movement therebetween. For example, the movement of the posterior module 204 can be performed substantially independently of movement of the anterior module 202. Thus, similar to the pivotable embodiment illustrated in FIGS. 11-12, the connector(s) 206 can enable articulation of the posterior module 204 relative to the anterior module 202. In some embodiments, this mechanism can serve to enhance the comfort and fit of the posterior module 204 while preserving the optical qualities of a lens supported by the anterior module 202.

The flexible coupling 210 can comprise a resilient material. For example, the flexible coupling 210 can be fabricated using a polymer or metal that is compressible, elastic, and/or soft or semi-rigid. In such embodiments, the flexible coupling 210 can extend between the anterior module 202 and a body 212 of the connector(s) 206 and be rigidly attached thereto such that the flexibility of the flexible coupling 210 facilitates relative movement between the connector(s) 206 and the anterior module 202.

The connector(s) 206 can also comprise a pair of posterior ends 214 that can be coupled to the posterior module 204. The posterior ends 214 can be fixedly or movably attached to the posterior module 204 by means of thermal bonding, adhesive bonding, snap fit or other mechanical engagement, and/or other coupling methods known in the art. In some embodiments, the posterior ends 214 of the connector(s) 206 can be formed as widened attachment elements. As illustrated, the widened attachment elements can be configured to provide an increased contact area between the connector(s) 206 and the posterior module 204 to facilitate attachment of the connector(s) 206 to the posterior module 204. As discussed above with respect to the embodiment shown in FIGS. 7-10, the posterior module 204 can comprise connection points, recesses, ridges, and the like to which the posterior ends 214 can be bonded and/or mechanically engaged. The discussion of these features is incorporated here and will not be repeated for the sake of brevity.

Additionally, the embodiment illustrated in FIGS. 13-16B can be configured such that the anterior module 202 comprises a semi-rigid or rigid material and/or construction. The anterior module 202 can support the lens in such a manner as to prevent substantial bending of the lens during use, thus providing optimal optical quality.

Figure 15:
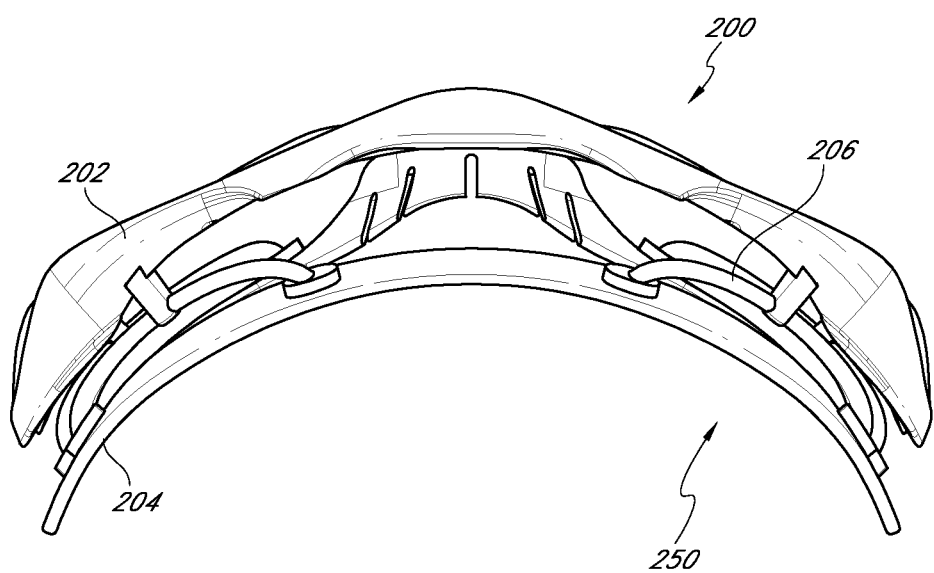
FIG. 15 is a top view of the goggle shown in FIG. 13, wherein the faceplate is in an undeflected position.
Figure 16A:
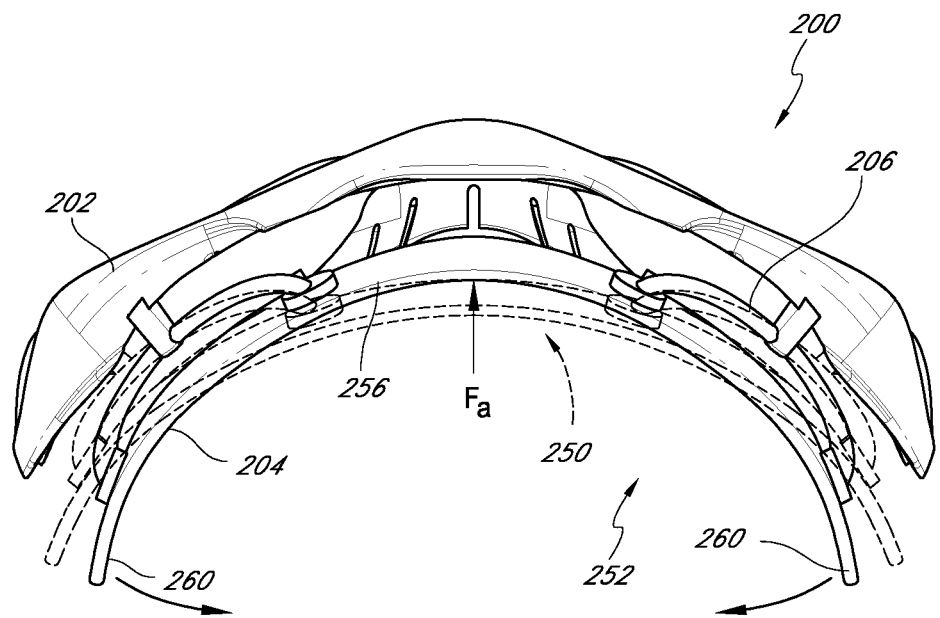
FIG. 16A is a top view of the goggle shown in FIG. 13, wherein the faceplate is in a narrowed deflected position.
Figure 16B:
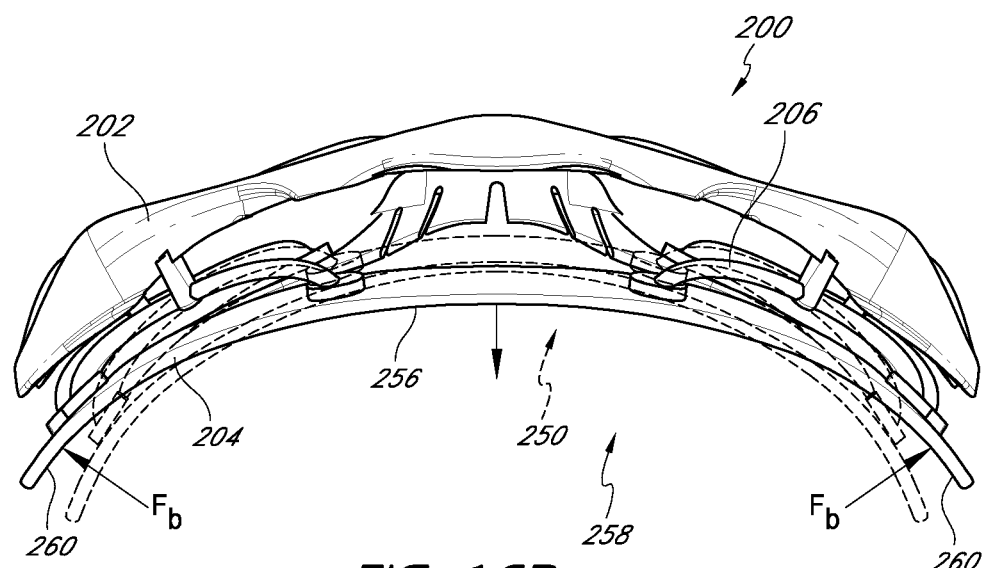
FIG. 16B is a top view of the goggle shown in FIG. 13, wherein the faceplate is in a widened deflected position.

FIGS. 15-16B illustrate top views of the goggle 200 in which the posterior module 204 is shown in an undeflected position 250 and deflected positions 252, 254, respectively. FIG. 16A illustrates the deflection of the posterior module 204 from the undeflected position 250 shown in FIG. 15 to the narrowed deflected position 252 in order to accommodate a narrow head size. FIG. 16B illustrates the deflection of the posterior module 204 from the undeflected position 250 shown in FIG. 15 to the widened deflected position 254 in order to accommodate a wide head size.

As shown in FIG. 16A, the posterior module 204 can deflect relative to the anterior module 202 when an anterior force Fa is exerted against a central portion 256 of the posterior module 204. Such an anterior force Fa is directed generally forwardly as a wearer with a narrow head places the goggle 200 on their head. Because the wearer has a narrow head, a gap would otherwise exist between the sides of the wearer's head and side portions of the goggle as the goggle is fitted against the wearer's head. This typical situation is shown and described above in FIG. 5.

However, in the embodiment illustrated in FIG. 16A, side portions 260 of the posterior module 214 can be drawn generally away or separated from the anterior module 202, thus converging onto the sides of the wearer's head which can improve fit and pressure distribution against the wearer's head. The central portion 256 of the posterior module 204 therefore moves in a direction generally toward the anterior module 202 while the side portions 260 of the posterior module 204 move in a direction generally away from the anterior module 202. Due to the articulation of the connectors 206 and the posterior module 204 relative to the anterior module 202, the posterior module 204 can be deflected towards a narrowed deflected position 252 in order to accommodate a narrow head size.

Similarly, FIG. 16B illustrates the goggle 200 wherein the posterior module 204 is deflected toward a widened deflected position 254. In FIG. 16B, the posterior module 204 can deflect relative to the anterior module 202 when lateral forces Fb are exerted against one or both of the side portions 260 of the posterior module 204. Such lateral forces Fb are directed generally outwardly against the posterior module 204 as a wearer with a wide head places the goggle 200 on their head. Because the wearer has a wide head, the side portions would otherwise be significantly compressed against the sides of the wearer's head, and the central portion of the goggle may make little contact or pressure against the central part of the wearer's head. This typical situation is shown and described above in FIG. 6.

However, in the embodiment illustrated in FIG. 16B, side portions 260 of the posterior module 214 can be deflected laterally and cause a central portion 256 of the posterior module 204 to converge toward the central part of the wearer's head in order to better distribute pressure against the wearer's head. The central portion of the posterior module 204 moves in a direction generally away from the anterior module 202 while the side portions 260 of the posterior module 204 move in a direction generally toward the anterior module 202. Due to the articulation of the connectors 206 and the posterior module 204 relative to the anterior module 202, the posterior module 204 can be deflected towards a widened deflected position 258 in order to accommodate a wide head size.

The movement of the posterior module 204 can be at least partially controlled by movement of the connectors 206. In some embodiments, the connectors 206 can be generally rigid bodies. In such embodiments, pivoting or rotation of the connectors 206 can cause one end of the connectors 206 to move generally toward the anterior module 202 while another end of the connectors 206 will move generally away from the anterior module 202. Thus, movement of a portion of the posterior module 204 can immediately cause corresponding movement of another portion of the posterior module 204. For example, a wishbone connector can provide this function. These features and functions can be implemented in any of the isostatic faceplate mechanism embodiments, which can be incorporated into any of the goggle embodiments.

Accordingly, the isostatic faceplate mechanism can provide differential adjustability of the posterior module relative to the anterior module in order to equalize pressure distribution across the wearer's head and to enhance the fit and comfort of the goggle over a wide range of head sizes. In some embodiments, the isostatic faceplate mechanism can cause displacement of portions of the posterior module in response to an applied force.

For example, a portion of the posterior module can adjust in a direction generally toward or away from the anterior module in response to an applied force while another portion of the posterior module adjusts in an opposite direction that is generally away from or towards the anterior module. In some embodiments, if a portion of a first posterior module is urged away from the anterior module due to an applied force (caused for example, while putting the goggles on), at least a second portion of the posterior module can be drawn towards the anterior module (which is reverse the direction of the first portion). In accordance with some embodiments, the deflection of the posterior module to provide conformance of the posterior module along the contours of the face of the wearer can aid in maintaining the orientation of the anterior module and lens of the goggle relative to the face of the wearer in a desired and generally constant orientation.

Further, independent articulation of the posterior module relative to the anterior module can allow the anterior module to support the lens in a generally undeflected orientation, thus enhancing optical performance of the lens. Moreover, in some embodiments that use a rigid anterior module, the flexibility and adjustability of the goggle are not compromised.

Figure 17:
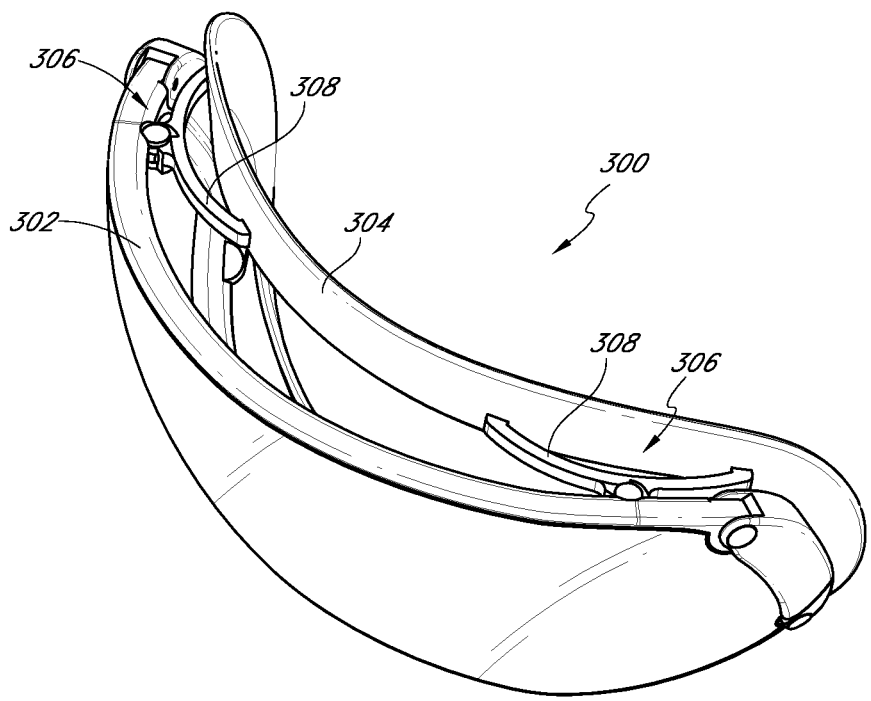
FIG. 17 is a top perspective view of another goggle having an isostatic faceplate with pivotable connectors, according to another embodiment.
Figure 18:
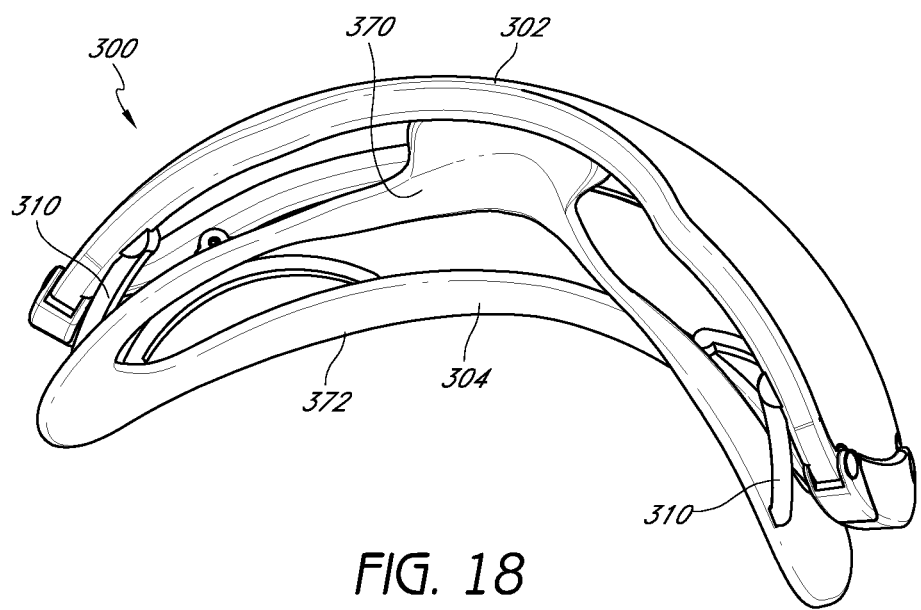
FIG. 18 is a bottom perspective view of the goggle shown in FIG. 17.

FIGS. 17-18 illustrate another embodiment of an isostatic faceplate mechanism incorporated into a goggle 300. The goggle 300 can comprise a lens support or anterior module 302 and a posterior module 304. The posterior module 304 can be coupled to the anterior module by at least one connector 306.

The connector(s) 306 can comprise either a movable or a fixed component that interconnects the anterior module 302 with the posterior module 304. The connector(s) 306 can comprise a compressible, an incompressible, a flexible, and/or inflexible material. The top perspective view of FIG. 17 illustrates that the connector(s) 306 can comprise a wishbone connector, similar to the embodiment illustrated and discussed above in FIGS. 11-12. The discussion of these features will not be repeated here, but is incorporated from the above discussion.

The bottom perspective view of FIG. 18 illustrates that the connector(s) 306 can also comprise an elongate link or arm 310. The arm 310 can be formed from a generally rigid material or a flexible material. Thus, the arm 310 can provide a generally fixed or a variable or dynamic spacing between the anterior module 302 and the posterior module 304. The use of the arm 310 can influence the articulation of the posterior module 304 relative to the anterior module 302. For example, in some embodiments, an upper pair of connectors may provide a dynamic articulation through the use of wishbone connectors while a lower pair of connectors may provide a simple articulation through the use of elongate arms.

Figure 19:
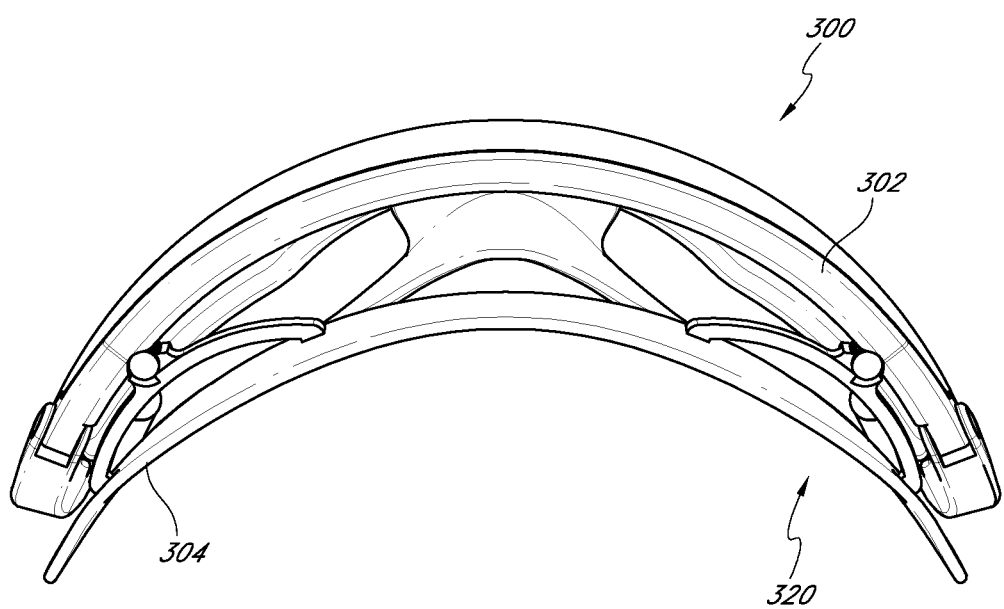
FIG. 19 is a top view of the goggle shown in FIG. 17, wherein the faceplate is in an undeflected position.

FIG. 19 illustrates a top view of the goggle 300 wherein the posterior module 304 is in an undeflected position 320. As such, the posterior module 304 can be biased towards the undeflected position 320. Although FIG. 19 illustrates the posterior module 304 in a widened position, the posterior module 304 can also be biased towards a narrow position.

Figure 20A:
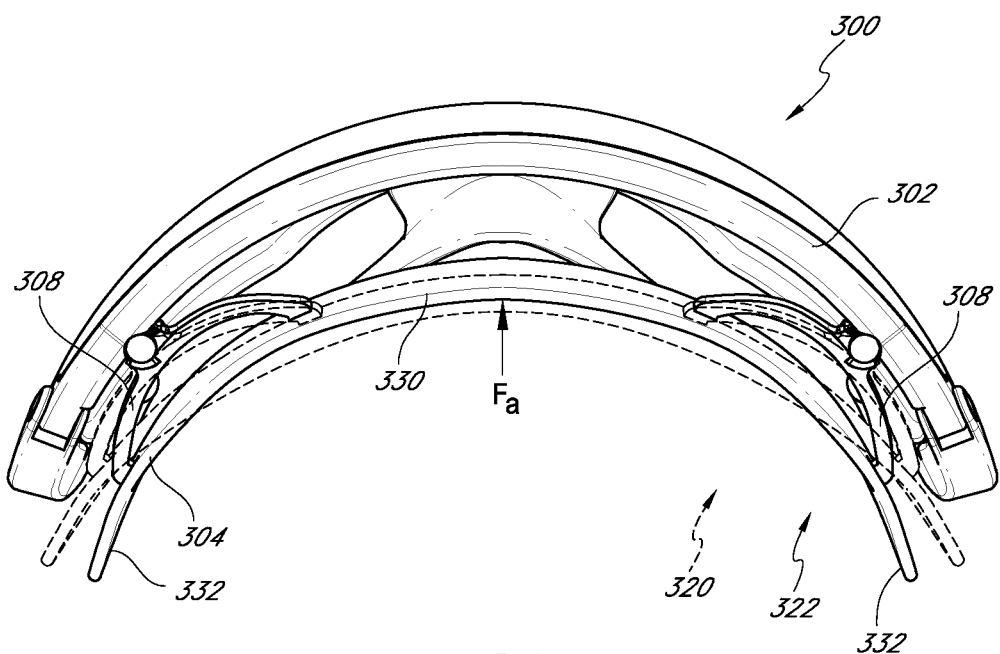
FIG. 20A is a top view of the goggle shown in FIG. 17, wherein the faceplate is in a narrowed deflected position.

FIG. 20A illustrates the posterior module 304 in a narrowed deflected position 322, with the undeflected position 320 being shown in dashed lines. Similarly to the embodiment shown and discussed in FIGS. 15-16B, an outwardly directed force Fa can be exerted against the posterior module 304 such that a central portion 330 is urged generally toward the anterior module 302. As the central portion 330 moves closer to the anterior module 302, side portions 332 of the posterior module 304 can be drawn generally away or separated from the anterior module 302. As discussed above with respect to FIGS. 15-16B, the connectors 306 can comprise a generally rigid material that enables opposing ends of the connectors 306 to move in generally opposite directions in response to rotation or pivoting of the connectors 306. In this manner, portions of the posterior module 304 can have interdependency of motion which can facilitate self-customization of the contour of the posterior module 304.

Figure 20B:
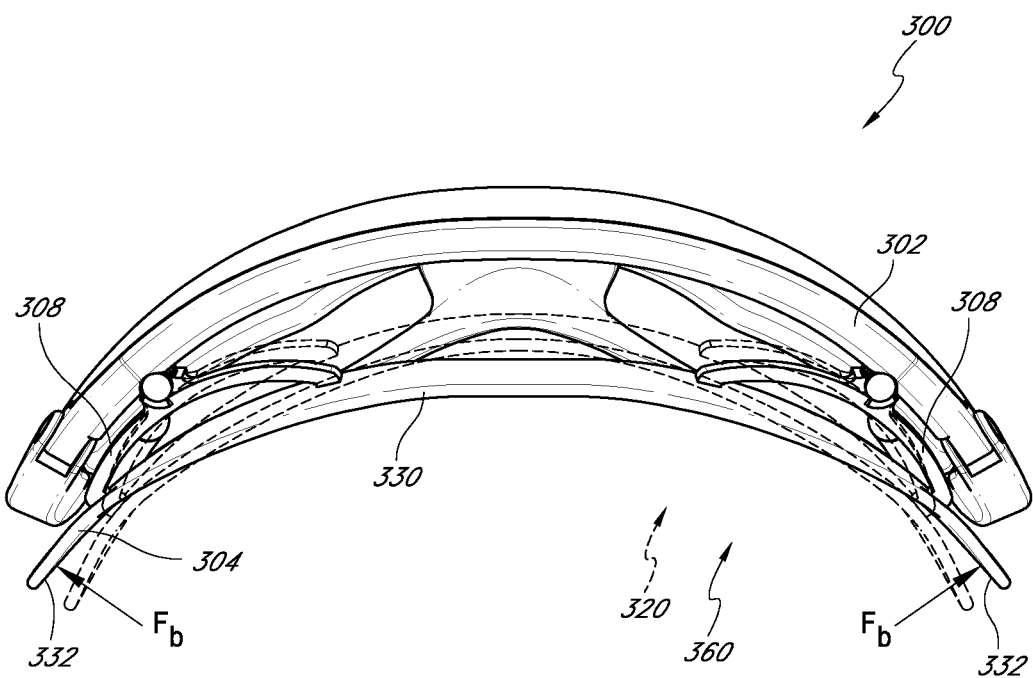
FIG. 20B is a top view of the goggle shown in FIG. 17, wherein the faceplate is in a widened deflected position.

FIG. 20B illustrates the goggle 300 wherein the posterior module 304 is in a widened deflected position 360. As shown, forces Fb exerted on the side portions 332 of the posterior module 304 can urge the side portions 332 generally towards the anterior module 302. Because of this motion, the central portion 330 of the posterior module 304 can be drawn generally away or separated from the anterior module 302. Accordingly, a wearer having a wide head can have a generally customized fit when wearing the goggle. In some embodiments, the posterior module 304 can self-adjust to the contour of the wearer's head.

In some embodiments, the isostatic faceplate mechanism can therefore allow self-adjusting of the posterior module of the goggle independent of movement of the anterior module. The movement of opposing ends or sides of the posterior module can be generally mirrored based on the location of an applied force. However, the connectors of the goggle can move independently of each other such that the articulation of one side of the posterior module is different from the articulation of the other side of the posterior module. Although such differences in articulation may be uncommon, this capability of some embodiments of the isostatic faceplate mechanism highlights the superior adjustability and self-customization that can be provided by the goggle.

Further, as shown in FIG. 18, some embodiments of the goggle can be provided with rigid or semi-rigid connectors. The rigid or semi-rigid connectors can support a portion of the posterior module at a given orientation relative to the anterior module and provide a pivot point for articulation in a lower portion of the posterior module.

The arms 310 shown in the embodiment of FIG. 18 are positioned adjacent to opposing sides of the anterior module 302. The arms 310 can be oriented such that longitudinal axes thereof converge at a point anterior to the face of the wearer and/or anterior to the goggle 300. In some embodiments, the arms 310 can support opposing sides of the posterior module 304 at a predetermined width or position relative to the anterior module 302. As such, when the goggle 300 is donned by a wearer, a lower portion 370 of the posterior module 304 can achieve moderate articulation using the pivot points created by the arms 310. Further, an upper portion 372 of the posterior module 304 can achieve a more aggressive articulation by virtue of the wishbone connectors 308. In such an embodiment, the articulation of the lower portion 370 and the upper portion 372 can provide dynamic adjustability of the posterior module 304.

Additionally, in some embodiments, the arms 310 can comprise a generally resilient or flexible material. The arms 310 can be pretensioned or biased towards a given position. For example, the arms 310 can be biased towards a narrow position such that the arms 310 can be widened when the goggle 300 is worn by a wearer. Biasing of the arms 310 can help in achieving an adequate seal between the posterior module 304 and the wearer's face.

As noted herein, some embodiments can provide for an interchangeable goggle by which a wearer can customize one or more components of the goggle. Some of the features and functions of the components, such as the shape, size, and biasing of the posterior module, the connectors, and the anterior module are a few of the parameters that can be customized through a modular goggle.

For example, a wearer could purchase connector arms were connectors that maintain a desired default orientation of the posterior module relative to the anterior module. Further, a wearer could purchase an anterior module having a desired size or coverage. As discussed further below, various types of connectors can be implemented in embodiments of the goggles.

Figure 21A:
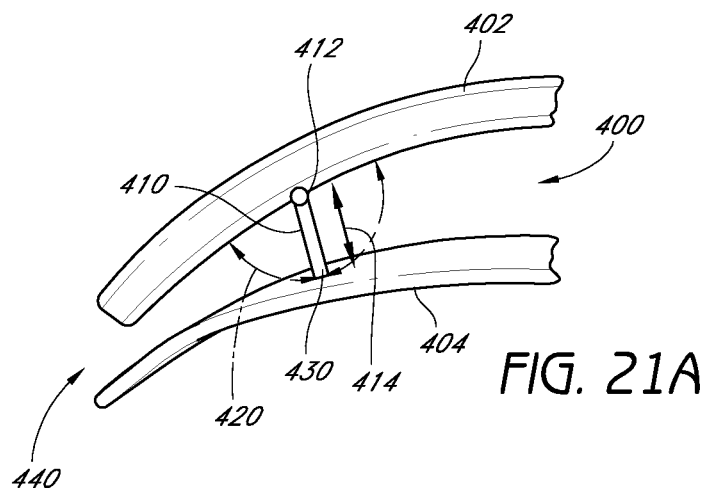
FIG. 21A is a partial top view schematic diagram of a partially pivotable straight connector for an isostatic faceplate wherein the connector is pivoted to a first position to accommodate a wide head, according to an embodiment.
Figure 21B:
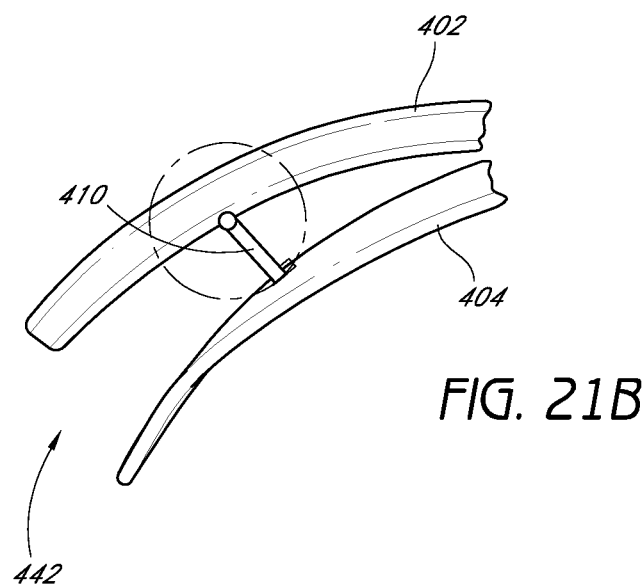
FIG. 21B is a partial top view schematic diagram of the connector shown in FIG. 21A wherein the connector is pivoted to a second position to accommodate a narrow head.

FIGS. 21A-B illustrates an embodiment of a movable connector 400 that is coupled with a lens support or anterior module 402 and a posterior module 404. The connector 400 comprises a rotatable segment 410 that is coupled to the anterior module 402 that at a rotatable joint 412. The rotatable segment 410 can define a length 414 can be rotated along an arcuate path 420 defined by the length 414. The connector 400 can be rigidly coupled to the posterior module 404 such that the orientation of the segment 410 is fixed relative to the posterior module 404. For example, the connector 400 can be oriented at a perpendicular angle with respect to the posterior module 404.

FIG. 21A illustrates the rotatable segment 410 positioning the posterior module 404 in a widened deflected position 440. FIG. 21B illustrates the rotatable segment 410 positioning the posterior module 404 in a narrowed deflected position 442. Due to the rigid coupling between the rotatable segment 410 and the posterior module 404, a rotatable segment 410 can connect with the posterior module 404 at a single point while providing an effect that is similar to the effect created by a wishbone connector. That is, movement of a central region of the posterior module 404 can trigger a corresponding opposing movement of a side region of the posterior module 404 relative to the anterior module 402.

Figure 22A:
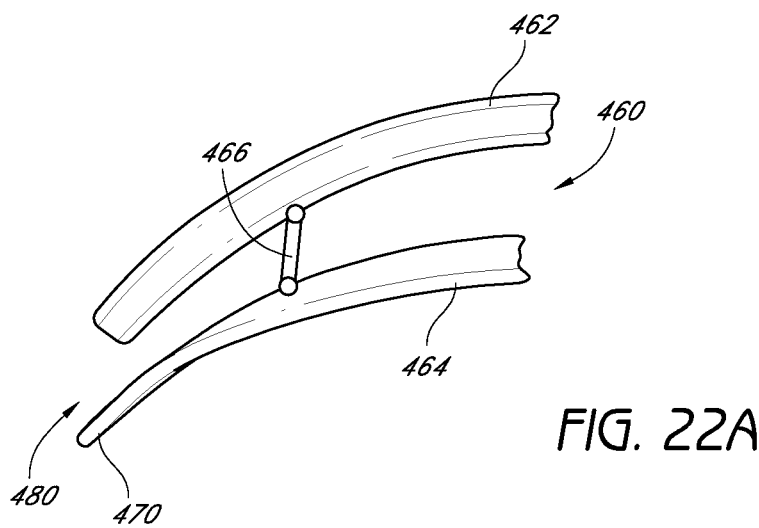
FIG. 22A is a partial top view schematic diagram of the connector shown in FIG. 22A wherein the connector is pivoted to a first position to accommodate a large head.
Figure 22B:
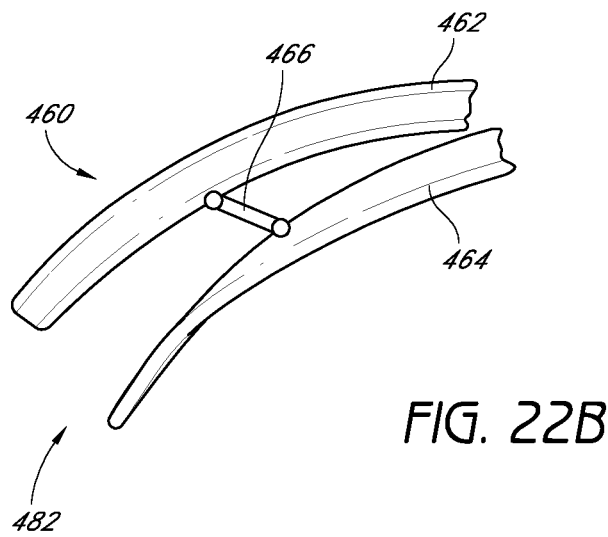
FIG. 22B is a partial top view schematic diagram of a dual pivotable straight connector for an isostatic faceplate wherein the connector is pivoted to a second position to accommodate a small head, according to another embodiment.

FIGS. 22A-B illustrate another embodiment of a moveable connector 460. The connector 460 can be coupled with a lens support or anterior module 462 and a posterior module 464. The connector 460 can comprise a rotatable segment 466 that is rotatably coupled to both the anterior module 462 and the posterior module 464.

In contrast to the embodiment illustrated in FIGS. 21A-B, the embodiment of the connector 460 shown in FIGS. 22A-B provides rotatable movement of the rotatable connector 466 relative to both the anterior module 462 and the posterior module 464. Accordingly, the articulation of the posterior module 464 relative to the anterior module 462 can be different than in the embodiment of FIGS. 21A-B. In particular, the embodiment of FIGS. 22A-B can provide a more subtle collapsing of a side region 470. The rotational movement of the rotatable segment 466 relative to the posterior module 462 can allow the posterior module 464 to maintain a generally parallel orientation relative to the anterior module 462 during articulation. Further, the rotatable segment 466 can also permit the posterior module 464 to be compressed more closely toward the anterior module 462 than in the embodiment shown in FIGS. 21A-B, due to the rotational coupling of the rotatable segment 466 and the posterior module 464.

Accordingly, while the posterior module 464 can achieve a widened deflected position 480, as shown in FIG. 22A, the posterior module 462 can all also achieve an intermediate narrowed position 482, as shown in FIG. 22B. The widened deflected position 480 may provide a larger or flatter contour and width for the wearer's head than the widened deflected position 440 illustrated in FIG. 21A. The widened deflected position 480 may be within a good range for a large, generally flat forehead. The intermediate narrowed position 482 can provide a larger width for the wearer's head than the narrowed deflected position 442 illustrated in FIG. 21B. The intermediate narrowed position 482 may be within a good range for a small-sized head.

In some embodiments, the size, configuration, and coupling mode of the connector can be selectively configured in order to achieve a desired articulation between the anterior module and the posterior module. As illustrated at discussed above with respect to FIGS. 21A-22B, some embodiments can be provided with a rotatable coupling at at least one connection point of the connector and one of the anterior module and the posterior module.

Further, one or both of the coupling joints between the connector and the anterior module and the posterior module can be configured to allow the connector to be disengaged therefrom. In this manner, the connector can be selectively replaced with a connector having a desired mechanical attribute. As such, the wearer can customize the goggle to their own specifications.

FIGS. 23A-E illustrate various positions of an embodiment of a connector 500 coupled with a lens support or anterior module 502 and a posterior module 504. As shown, the connector 500 can be rotatably coupled to the anterior module 502. The connector 500 can comprise a wishbone connector 510 that is coupled to a link 512. The link 512 can comprise a short segment that interconnects the wishbone connector 510 with the anterior module 502.

Figure 23A:
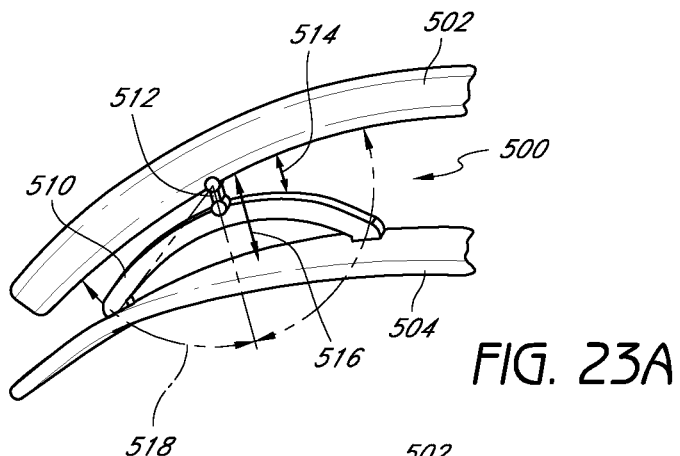
FIG. 23A is a partial top view schematic diagram of a wishbone connector for an isostatic faceplate wherein the connector is in an undeflected position, according to an embodiment.

In some embodiments, the link 512 can be rotatably coupled to both the wishbone connector 510 and the anterior module 502. Further, the link 512 can define a length 514. As shown in FIG. 23A, to wishbone connector 510 and the link 512 can separate the posterior module 504 from the anterior module 502 by a separation distance 516. Due to the rotational coupling of the link 512, the connector 500 and the posterior module 504 can rotate with respect to the anterior module 502 generally along a rotational path 518. However, in contrast to the rotatable wishbone connector shown in FIGS. 17-20B, the rotational path 518 represents a range of possible rotational positions that can vary due to the rotational coupling between the link 512 and both the anterior module 502 and the wishbone connector 510. In fact, the range of rotational positions provided by the rotational path 518 increases as the length 514 of the link 512 is increased. Indeed, by varying the length 514 of the link 512 and the separation distance 516, the articulation of the posterior module 504 can be modified to a desirable range.

Figure 23B:
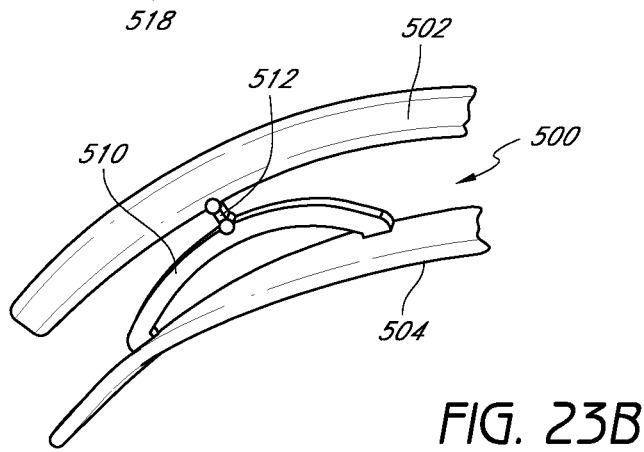
FIG. 23B is a partial top view schematic diagram of the connector shown in FIG. 23A wherein the connector is pivoted to a first position.
Figure 23C:
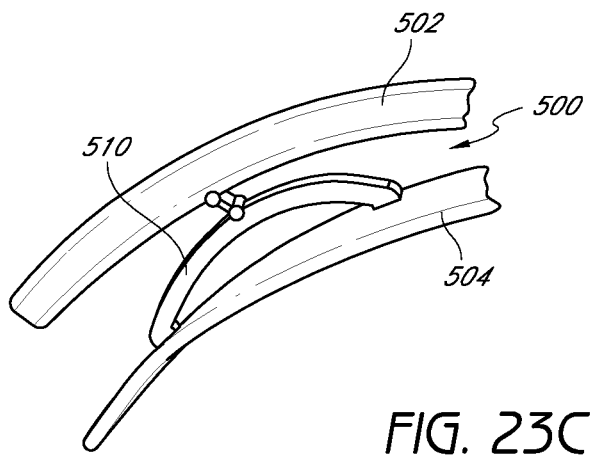
FIG. 23C is a partial top view schematic diagram of the connector shown in FIG. 23A wherein the connector is pivoted to a second position.
Figure 23D:
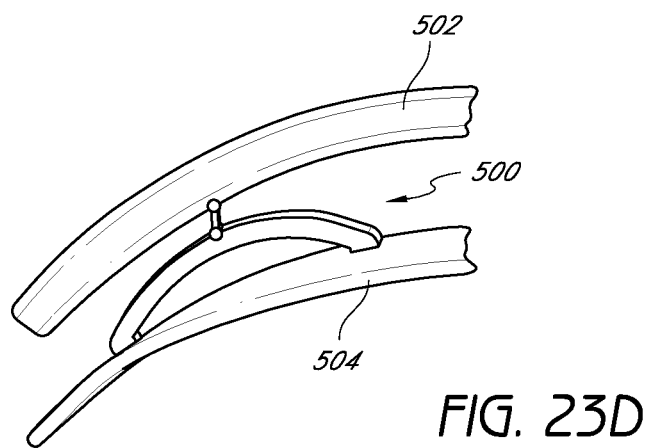
FIG. 23D is a partial top view schematic diagram of the connector shown in FIG. 23A wherein the connector is pivoted to a third position.
Figure 23E:
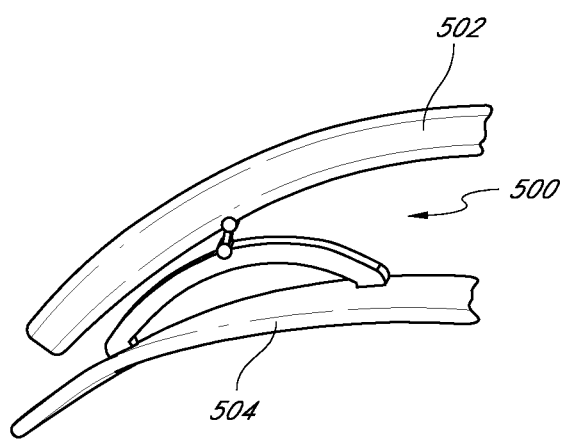
FIG. 23E is a partial top view schematic diagram of the connector shown in FIG. 23A wherein the connector is pivoted to a fourth position.

FIGS. 23A-E illustrate several possible rotational orientations of the connector 500 and the posterior module 504 relative to the anterior module 502. FIG. 23A represents a position of the posterior module 504 in which a medium or intermediate-sized head could be accommodated. FIGS. 23B-C illustrate progressively narrower positions of the posterior module 504 while FIGS. 23D-E illustrate progressively wider positions of the position posterior module 504.

The embodiment illustrated in FIGS. 23A-E provides an example of a connector that can incorporate more than one component in a movable assembly in order to provide a more dynamic articulation of the posterior module relative to the anterior module. In some embodiments, three or more components can be used in the assembly to enhance the articulation of the goggle.

Figure 24A:
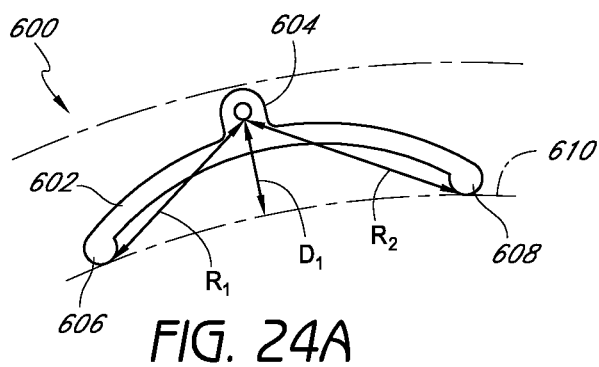
FIG. 24A is a top view of a wishbone connector according to an embodiment.

FIGS. 24A-25B illustrate additional embodiments of a connector that can be used in some embodiments of the goggle. FIGS. 24A-B illustrate embodiments of the connector in which geometric constraints have been modified to create a desired articulation of any posterior module relative to any anterior module of the goggle.

For example, FIG. 24A shows a connector 600 that comprises a wishbone-shaped body 602 and a pivotal coupling 604 extending from the body 602. The pivotal coupling 604 can be rotatably coupled to the anterior module of the goggle. Further, first and second ends 606, 608 of the body 602 can be coupled to the posterior module of the goggle. The ends 606, 608 can be rigidly or rotatably coupled to the posterior module. As illustrated, the pivotal coupling 604 can be spaced at a separation distance D1 from a dashed line 610 representing the location of the posterior module. Further, the first end 606 can be spaced from the pivotal coupling 604 at a first radius R1. The second end 608 can be spaced from the pivotal coupling 604 at a second radius R2.

In some embodiments, the first and second radii R1, R2 can be generally equal to each other. In such embodiments, rotational movement of the connector 600 about the pivotal coupling 604 can then create equal displacement of the first and second ends 606, 608, which can result in generally equal and opposite displacement of portions of the posterior module 610 coupled to the respective first and second ends 606, 608 of the connector 600.

Figure 24B:
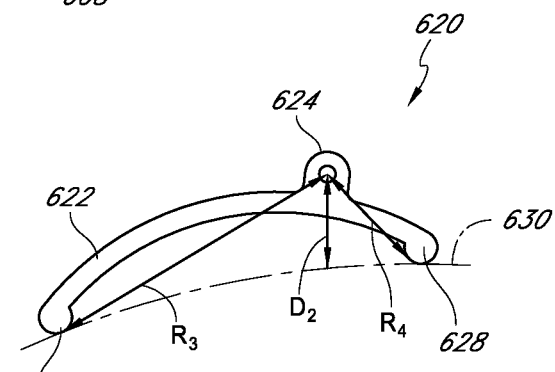
FIG. 24B is a top view of a wishbone connector according to another embodiment.

However, FIG. 24B illustrates a connector 620 that provides different articulation than the connector 600. The connector 620 comprises a wishbone-shaped body 622, a pivotal coupling 624 extending from the body 622, and first and second ends 626, 628. As illustrated, the pivotal coupling 624 can be spaced at a separation distance D2 from a dashed line 630 representing the location of the posterior module. Further, the first end 626 can be spaced from the pivotal coupling 624 at a third radius R3, and the second end 628 can be spaced from the pivotal coupling 624 at a fourth radius R4.

In some embodiments, the third and fourth radii R3, R4 can be different distances. As illustrated, the third radius R3 can be approximately doubled the fourth radius R4. However, the third and fourth radii R3, R4 can be selectively adjusted in order to achieve a desired articulation, as described below.

In contrast to the embodiment of the connector 600 shown in FIG. 24A, the connector 620 shown in FIG. 24B creates different amounts of displacement at the first and second ends at 626, 628 of the connector 620 in response to rotation about the pivotal coupling 624. Thus, a force for displacement in a given direction against a portion of the posterior module 630 can create a muted, albeit responsive displacement of another portion of the posterior module 630. Embodiments of the goggle can be provided in which the dimensions D1, D2, R1, R2, R3, R4 of the connectors 600, 620 are varied in order to provide a desired articulation of the connectors 600, 620 and the posterior module attached thereto.

Figure 25A:
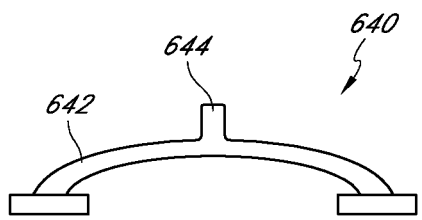
FIG. 25A is a top view of a wishbone connector according to yet another embodiment.
Figure 25B:
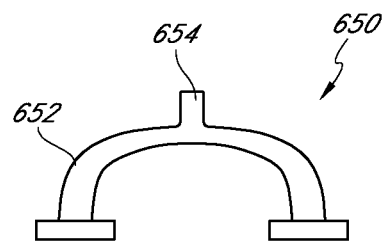
FIG. 25B is a top view of a wishbone connector according to yet another embodiment.

FIG. 25A-B illustrate additional embodiments of a connector. FIG. 25A illustrates a connector 640 having a generally wide, short body 642 while FIG. 25B illustrates a connector 650 having a generally narrow, tall body 652. The connectors 640, 650 can be used, for example, in embodiments of a goggle such as that shown above in FIGS. 13-16B, in which anterior portions 644, 654 of the connectors 640, 650 are flexibly or movably coupled to a lens support or anterior module. Similar to the embodiments illustrated in FIGS. 24A-B, the configuration of the connectors 640, 650 can be selectively modified in order to achieve a desired articulation.

Figure 26:
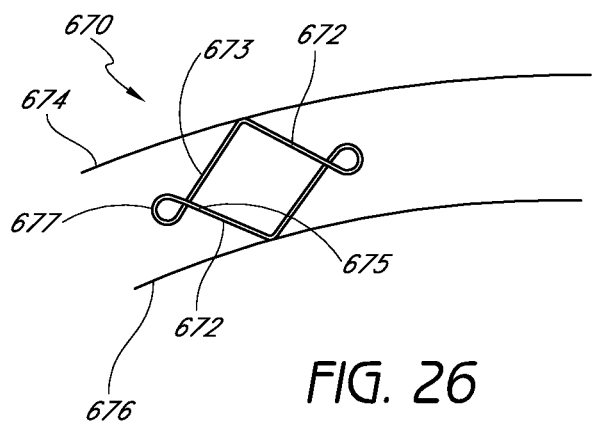
FIG. 26 is a top view of an expandable cell connector according to yet another embodiment.

In another embodiment of a connector, FIG. 26 illustrates an expandable cell connector 670. The expandable cell connector 670 can comprise at least one leaf spring component 672 having anterior and posterior ends that can be coupled to respective ones of a lens support or anterior module 674 and a posterior module 676. The expandable cell connector 670 can be formed in a diamond shape and be deformed in response to compression between the posterior module 676 and the anterior module 674.

In general, the expandable cell connector comprises at least a first strut 673 which is moveably or rigidly connected to the anterior module 674, and a second strut 675 which is rigidly or moveably connected to the posterior module 676. First strut 673 and second strut 675 may be anterior and posterior sections of a single, arcuate leaf spring. Alternatively, first strut 673 and second strut 675 are separated by a bend or hinge point 677. In the illustrated embodiment, the hinge point 677 comprises a loop of wire, which allows the angle between first strut 673 and second strut 675 to be varied through a wide angular range without exceeding the elastic limit of the material. Suitable materials include any of a wide variety of polymers, and also super elastic metals or spring metals, such as spring steel, Nitinol, Elgiloy and others known in the art.

The expandable cell connector illustrated in FIG. 26 includes a third strut and a fourth strut, separated by a second hinge point to define an enclosed cell. The cell functions as a spring or shock absorber between the two points of contact with the anterior and posterior modules. Two or three or four or five or six or more expandable cell connectors 670 may be provided along either the upper or lower portion of the frame. Spring cells in accordance with the present invention may be provided with four or five or six or more walls, and may comprise a honeycomb configuration in which the struts are replaced by a thin membrane.

In some embodiments, the leaf spring component 672 can be fabricated from a resilient material, such as a plastic or metal that can be elastically deflected. The leaf spring component 672 can comprise a generally elongate body. The leaf spring component 672 can be separately or monolithically formed with one or more additional leaf spring components 672. Thus, the shape and configuration of the expandable cell connector 670 can vary depending on the number and orientation of the individual components of the expandable cell connector 670.

For example, the body of the leaf spring component 672 can comprise one or more curved portions and one or more straight portions. The body of the leaf spring component 672 can have the shape of a bent pin or a spring. Further, the leaf spring component 672 can be fabricated in the shape of a loop in order to facilitate distribution of compressive forces within the body of the leaf spring component 672.

Figure 27:
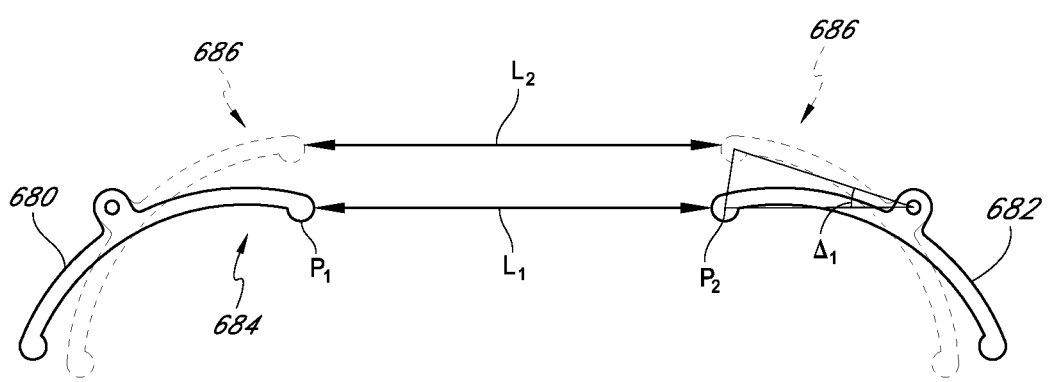
FIG. 27 is a top view schematic diagram of a pair of wishbone connectors illustrating movement of the connectors, according to an embodiment.

FIG. 27 is a schematic diagram illustrating movement of the connectors and the respective spacing of the connectors. FIG. 27 illustrates first and second connectors 680, 682 that can be pivotably coupled to an anterior module (not shown) and rigidly coupled to a posterior module (not shown). The first and second connectors 680, 682 are shown in solid lines in an undeflected position 684 and dashed lines in a deflected position 686. The first and second connectors 680, 682 can rotate through an angle Δ1, as indicated in FIG. 27.

As illustrated, interior connection points P1, P2 of the first and second connectors 680, 682 are spaced apart at a distance L1 when in the undeflected position 684 and at a distance L2 when in the deflected position 686. Although the actual length of the posterior module disposed between the interior connection points P1, P2 of the first and second connectors 680, 682 may be greater than either distance L1, L2, FIG. 27 indicates that the actual length of the posterior module disposed between the interior connection points P1, P2 must be at least equal to the distance L2 in order for the first and second connectors 680, 682 to be deflected towards the deflected position 686. In some embodiments, the actual length of the posterior module disposed between the interior connection points P1, P2 can also be greater than the distance L2 such that the posterior module is not placed in tension in the deflected position 686.

FIG. 27 also indicates that in some embodiments, the movement of a pair of connectors towards a deflected position may actually separate connection points of the connectors while causing other connection points of the connectors to converge. For example, the separation of inner connection points can generally tend to flatten out a central portion of the posterior module while the convergence of the inner connection points may tend to increase the curvature of the central portion of the posterior module.

In some embodiments, the first and second connectors 680, 682 can be configured and mounted relative to the anterior module such that rotation toward the deflected position 686 causes separation of the interior connection points P1, P2. However, the first and second connectors 680, 682 can be configured and mounted relative to the anterior module such that rotation toward the deflected position 686 causes convergence of the interior connection points P1, P2. In either of such embodiments, the articulation of the posterior module can be manipulated in order to target a desired range of head sizes for that embodiment.

Quick Release Lens Goggle Embodiments

Referring now to FIGS. 28-34C, embodiments of an interchangeable lens structure or quick release lens mechanism. As noted previously, any of the features disclosed herein can be individually incorporated into embodiments of the goggles and eyeglasses and incorporated into goggle and eyeglass embodiments in combination with other features. FIGS. 28-34C illustrate embodiments of a goggle wherein the anterior module of the goggle has been modified to comprise an interchangeable lens structure. Embodiments of the anterior module that comprise an interchangeable lens structure can be paired with embodiments of the connector(s) and/or posterior module.

Some embodiments of lens engagement systems are provided in Applicants' copending U.S. patent application Ser. No. 12/648,232, filed on Dec. 28, 2009, titled Eyeglass with Enhanced Ballistic Resistance and U.S. patent application Ser. No. 13/020,747, filed on Feb. 3, 2011, titled Eyewear with Enhanced Ballistic Resistance, the entireties of both of which are incorporated herein by reference. Further, these teachings are believed to apply for goggle and eyeglass technologies. These applications also include other features and aspects of eyewear features, including but not limited to goggle strap technology, the entireties of the related disclosures are also incorporated herein by reference.

Figure 28:
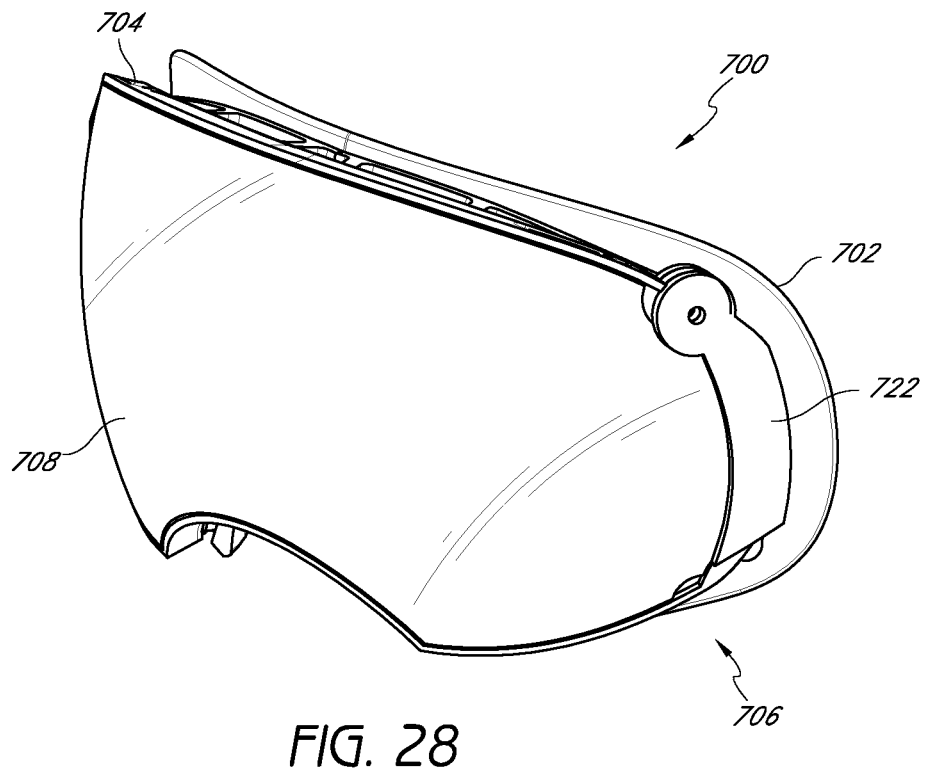
FIG. 28 is a perspective view of a goggle having an interchangeable lens mechanism, according to an embodiment.
Figure 29:
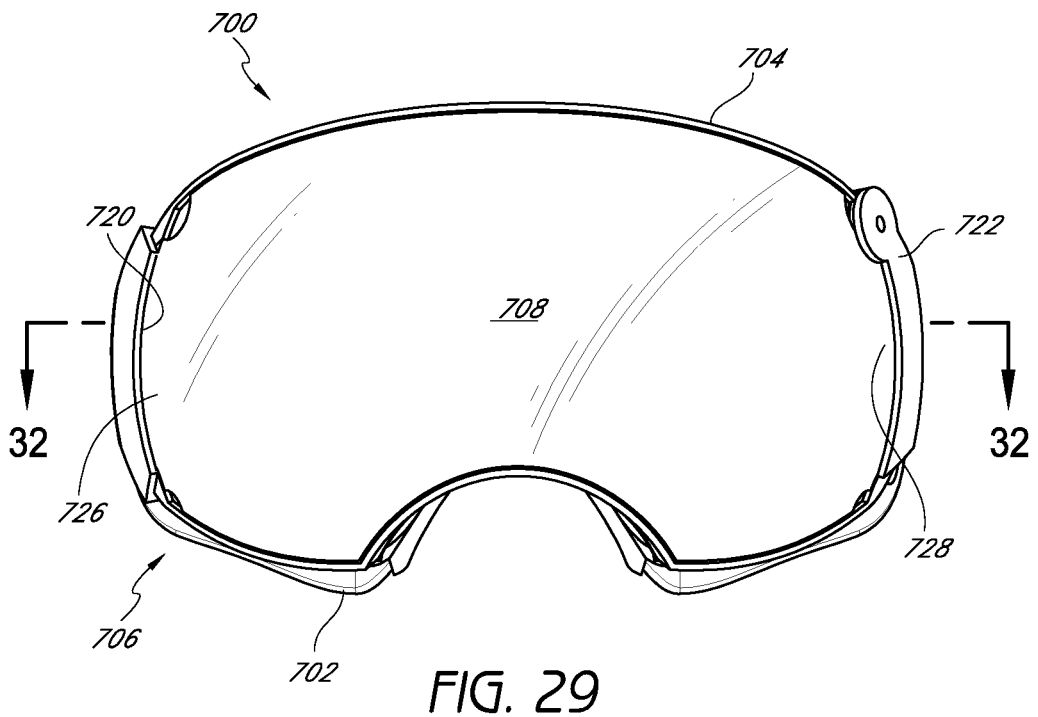
FIG. 29 is a front view of the goggle shown in FIG. 28.

In some embodiments, the eyewear can comprise a frame or lens support with at least one engagement section for supporting and engaging a lens. FIGS. 28-29 illustrate an embodiment of a goggle 700 comprising a posterior module 702 and a lens support or anterior module 704 that incorporates an engagement section or interchangeable lens structure 706. The goggle 700 can also comprise a lens 708 that can be releasably retained by the interchangeable lens structure 706.

In some embodiments, the interchangeable lens structure 706 can provide at least one interconnection point or engagement section 710 between the lens 708 and the anterior module 704 where the lens 708 is secured to the anterior module 704. The interchangeable lens structure 706 can comprise a structure that moves relative to the lens 708. The interchangeable lens structure 706 can also comprise one or more stationary structures, which can be used in combination with movable structures to engage the lens 708 to retain the lens 708 in a mounted position.

For example, the interchangeable lens structure 706 of the goggle 700 can comprise at least one engagement section 710. The engagement section(s) 710 can comprise at least one retention socket 720 and/or at least one retention clip 722. Further, the engagement section 710, the retention socket 720, and/or the retention clip 722 can comprise an engagement structure or member such as a depression, recess, receptacle, or socket and/or a protruding portion. In the illustrated embodiment, the retention socket 720 can receive and retain a least a portion of the lens 708 while the retention clip 722 can rotate relative to the lens 708 in order to secure the lens 708 in a mounted position on the goggle 700. As illustrated in FIG. 29, the retention socket 720 can receive a first side 726 of the lens 708, and the retention clip 722 can secure a second side 728 of the lens 708 when the lens 708 is in the mounted position.

Figure 30:
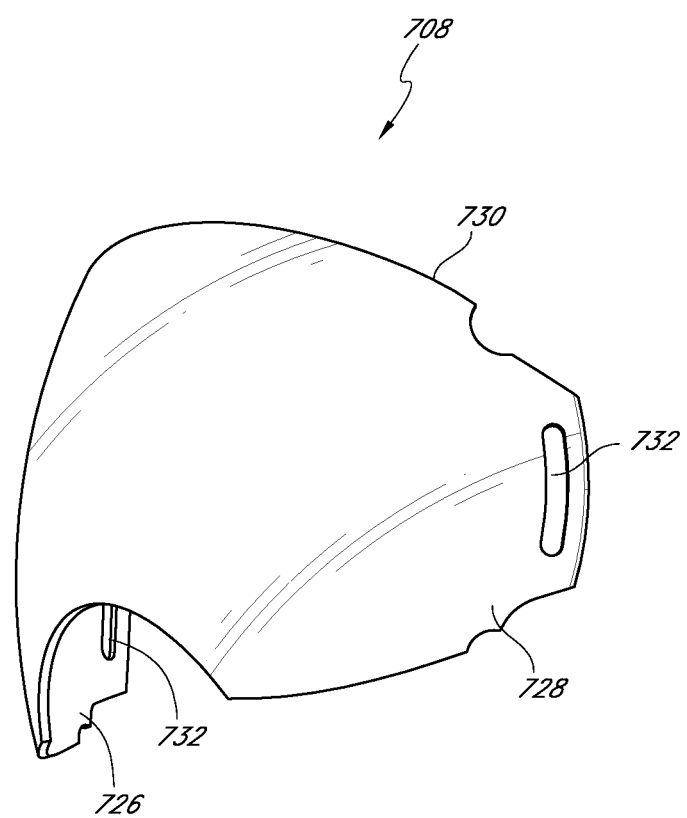
FIG. 30 is a perspective view of a lens for use with the goggle shown in FIG. 28, according to an embodiment.

FIG. 30 illustrates a perspective view of the lens 708 according to an embodiment. The lens 708 can comprise the first and second ends 726, 728 and a lens periphery 730. In some embodiments, one of the first and second ends 726, 728 of the lens 708 can comprise at least one retention structure 732. The retention structure 732 can comprise one or more apertures, recesses, ridges, and/or protrusions formed along a respective end 726, 728 of the lens 708. In the embodiment illustrated in FIGS. 28-32A, the retention structures 732 comprise oblong apertures formed in the respective ends 726, 728 of the lens 708.

Figure 31A:
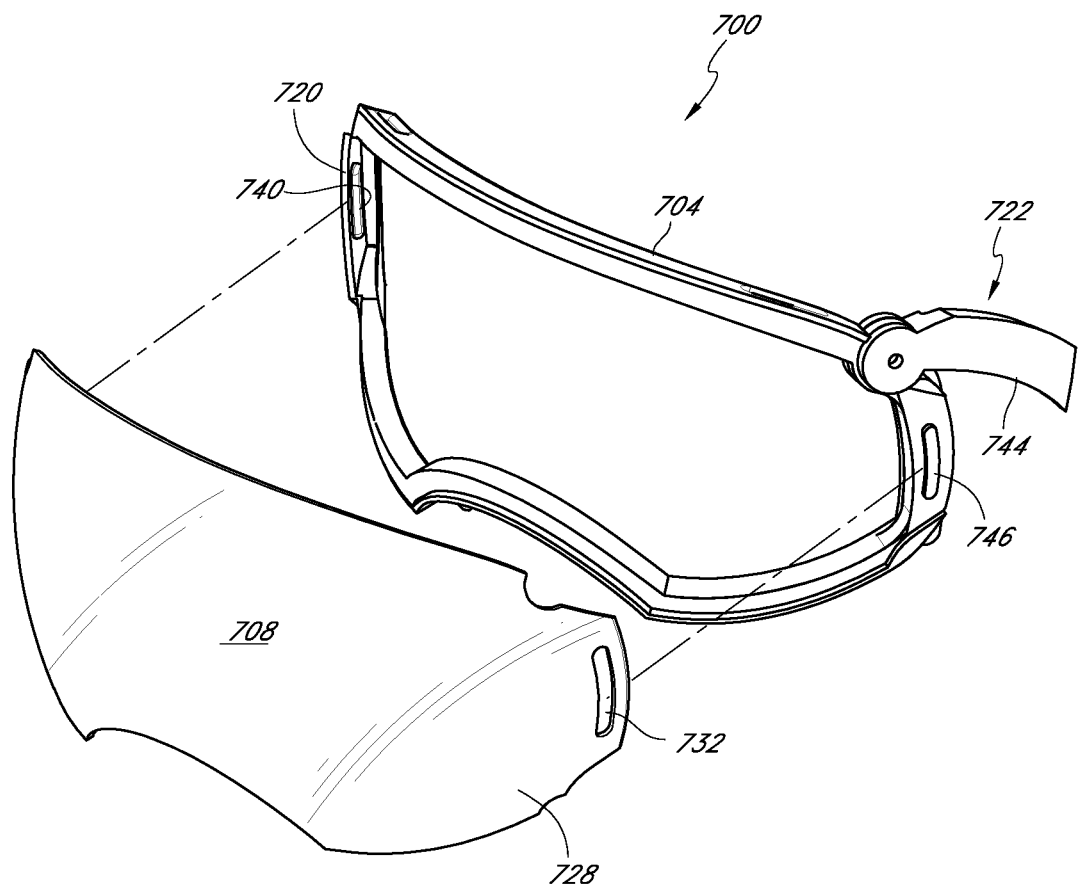
FIG. 31A is a perspective view of the goggle shown in FIG. 28 wherein the lens is being interchanged into the goggle, according to an embodiment.

Referring now to FIGS. 31A-32A, the structure of an embodiment of the interchangeable lens structure 706 and its engagement with the lens 708 will be described. FIG. 31A illustrates further features of the retention socket 720 and the retention clip 722. The retention socket 720 can be formed such that the first end 726 of the lens 708 can be inserted into the retention socket 720 and at least partially constrained against anterior motion. Thus, the retention socket 720 can comprise a cavity or space configured to receive at least a portion of the lens 708.

In some embodiments, the retention socket 720 can be formed to comprise at least one engagement member 740 that can be configured to engage with the retention structure 732 of the lens 708. For example, the engagement member 740 of the retention socket 720 can be positioned on an inner, anterior face of the retention socket 720 such that the engagement member 740 can engage the retention structure 732 of the lens 708 from a position anterior to the lens 708. However, the engagement member 740 can also be positioned on an inner posterior face of the retention socket 720 such that the engagement member 740 can engage the retention structure 732 from a position posterior to the lens 708. Moreover, the engagement member 740 can be disposed along an interior lateral side of the retention socket 720 such that a side edge of the first end 726 of the lens 708 can contact and/or engage with the engagement member 740.

Additionally, the retention clip 722 can be configured to engage with the second ends 728 of the lens 708 in order to at least partially constrain the lens 708 against anterior motion. For example, the retention clip 722 can comprise an actuating jaw 744 and an engagement member 746. In some embodiments, the jaw 744 can comprise a retention structure configured to engage with a portion of the lens 708. In the embodiment illustrated in FIG. 31A, the jaw 744 is movable or rotatable with respect to the engagement member 746. Further, the jaw 744 can be configured to translate with respect to the anterior module 704 and/or be removably attachable to the anterior module 704.

The engagement member 746 can be formed along a portion of the engagement section 710 of the anterior module 704. For example, the engagement member 746 can be formed along an anterior face of the anterior module 704, such as to extend from a recess formed in the engagement section 710. In some embodiments, the engagement member 746 can comprise at least one protrusion and/or recess configured to engage with the retention structure 732 of the second end 728 of the lens 708. As discussed further below, when the engagement member 746 of the retention clip 722 is engaged with the retention structure 732 of the lens 708, the jaw 744 can be rotated from a disengaged position to an engaged position to constrain movement of the lens 708 relative to the engagement member 746 of the retention clip 722.

Figure 31B:
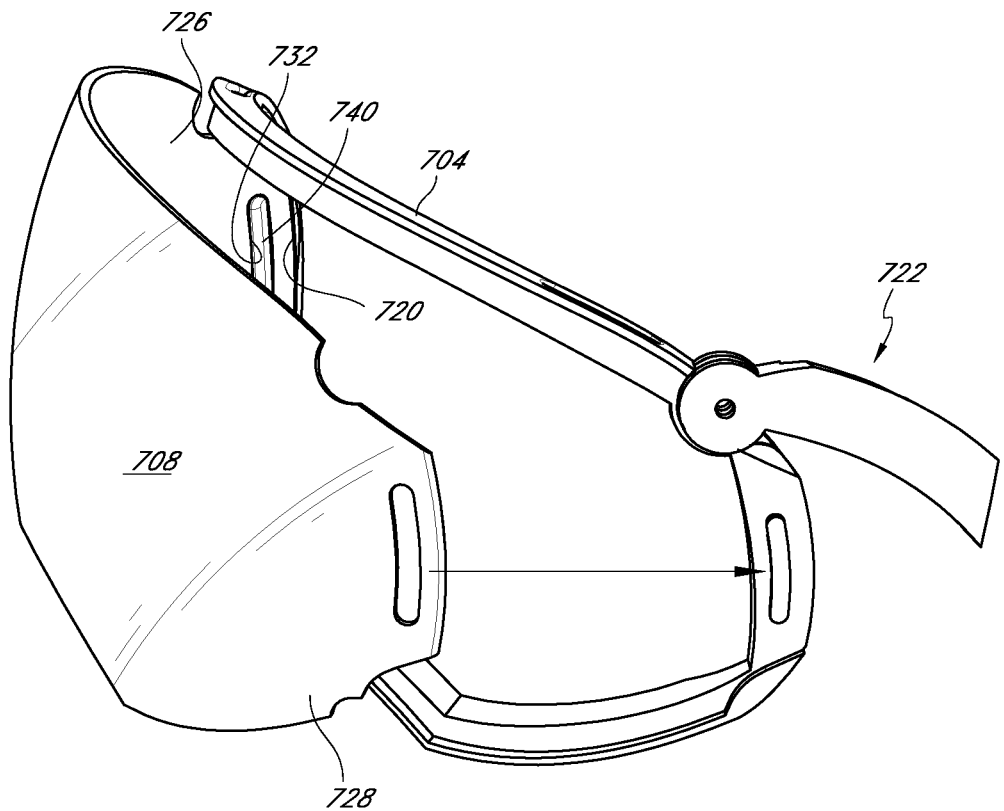
FIG. 31B is a side perspective view of the goggle shown in FIG. 28 wherein a first side of the lens is inserted into a receptacle of the interchangeable lens mechanism, according to an embodiment.

FIG. 31B illustrates a first stage of mounting and securing the lens 708 to the anterior module 704 using the interchangeable lens structure 706. As shown, the first end 726 of the lens 708 is inserted into the retention socket 720 such that the engagement member 740 of the retention socket 720 engages with the retention structure 732 of the first end 726 of the lens 708. When the first end 726 of the lens 708 is in place, the second end 728 of the lens 708 is moved towards the retention clip 722.

Figure 31C:
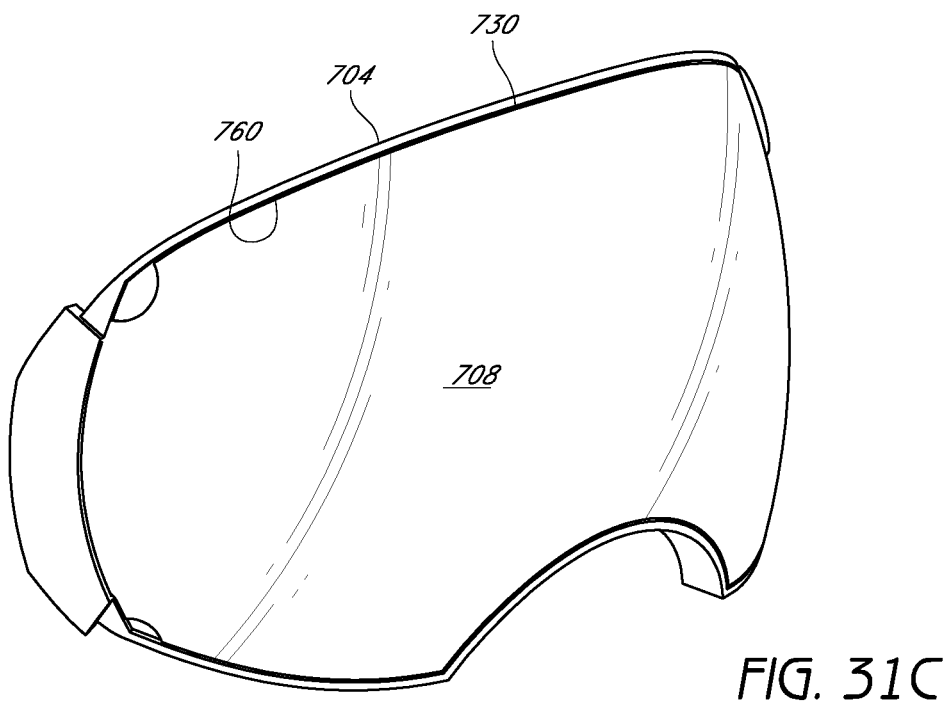
FIG. 31C is a side perspective view of the goggle shown in FIG. 28 wherein the first side of the lens is inserted into the receptacle of the interchangeable lens mechanism and a second side of the lens is fitted against the goggle.

FIG. 31C illustrates the lens 708 in a mounted position relative to the anterior module 704 of the goggle 300. In the mounted position, the lens periphery 730 can be generally flush or mate with a periphery 760 of the anterior module 704.

Figure 31D:
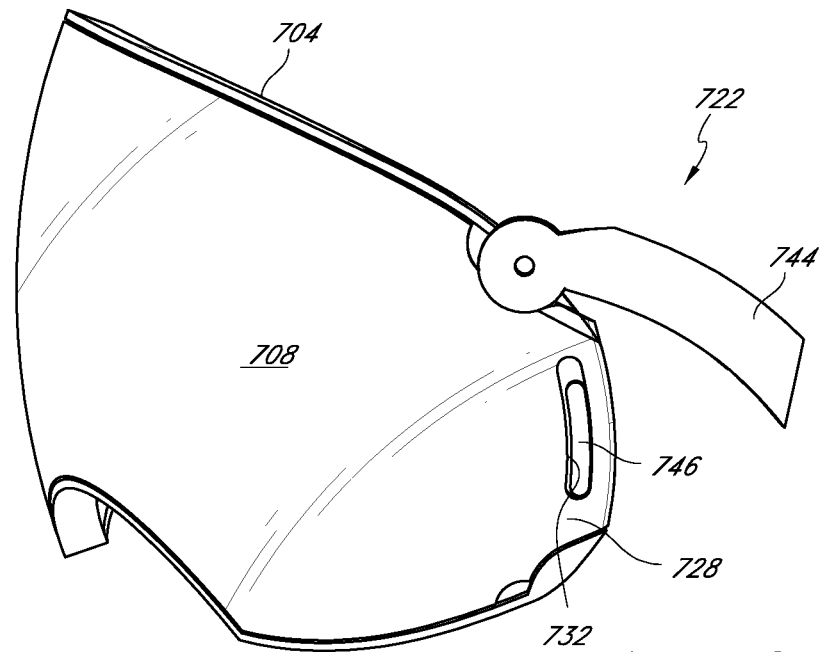
FIG. 31D is a perspective view of the goggle shown in FIG. 28 illustrating the second side of the lens being fitted against the goggle and a pivotable securing member in a disengaged position, according to an embodiment.

FIG. 31D also illustrates the lens 708 in the mounted position relative to the anterior module 704 prior to actuation of the retention clip 722. As shown, the retention structure 732 of the second end 728 of the lens 708 can be aligned with or initially engaged with the engagement member 746 of the retention clip 722. In the illustrated embodiment, a protrusion of the engagement member 746 has been inserted into an aperture formed in the second end 728 of the lens 708.

Figure 31E:
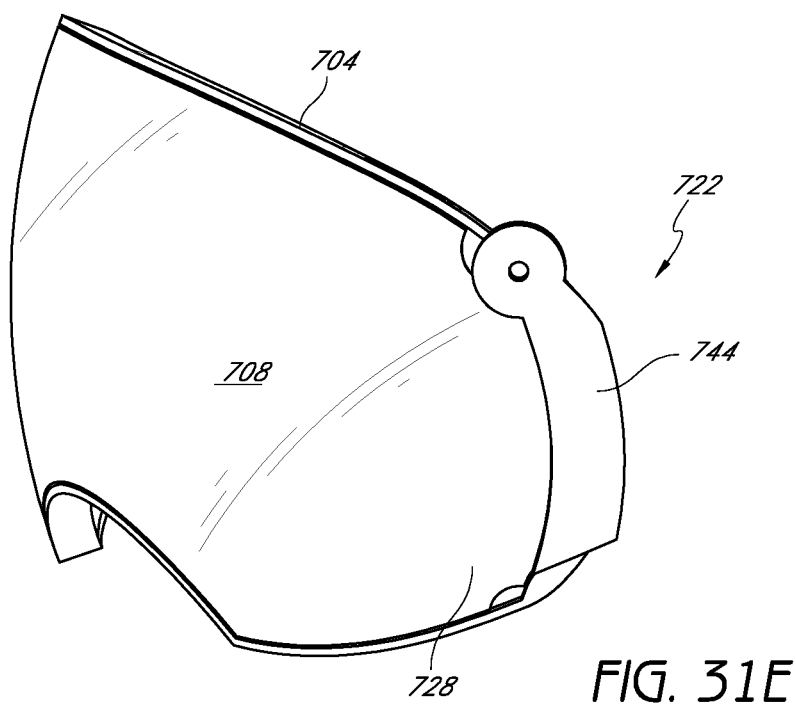
FIG. 31E is a perspective view of the goggle shown in FIG. 28 illustrating the second side of the lens being fitted against the goggle and the pivotable securing member in an engaged position, according to an embodiment.

Subsequent to alignment of the lens 708 with the retention socket 720 and the retention clip 722, the jaw 744 of the retention clip 722 can be moved from the disengaged position (shown in FIG. 31D) to an engaged position, as shown in FIG. 31E. In the illustrated embodiment, the jaw 744 is rotated to the engaged position, thus constraining the lens 708 from a degree of movement.

Figure 32:
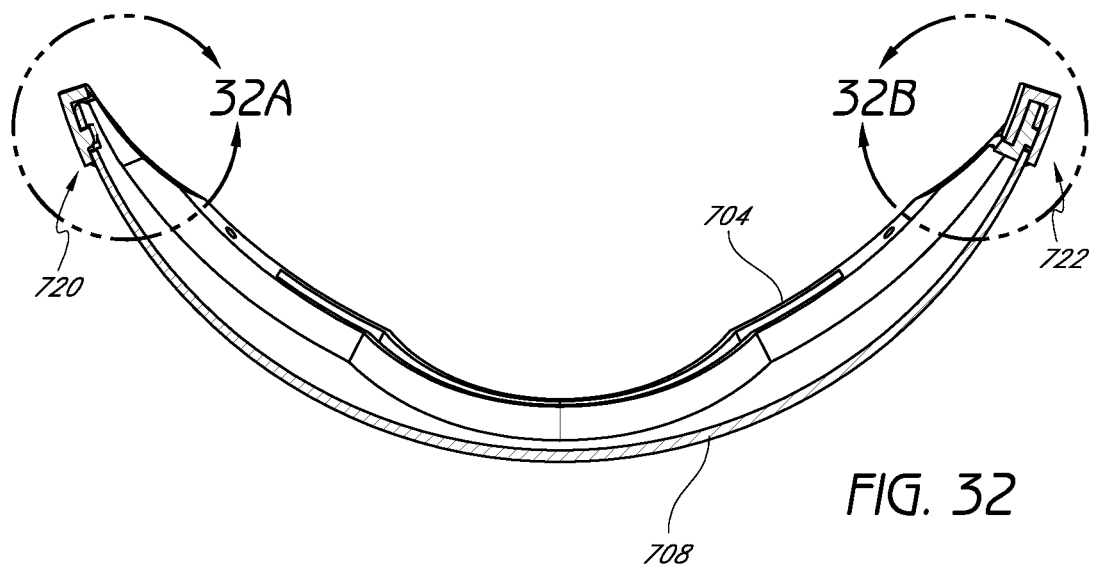
FIG. 32 is a top cross-sectional view of the goggle shown in FIG. 28 illustrating engagement of the first side of the lens in the receptacle of the interchangeable lens mechanism, according to an embodiment.
Figure 32A:
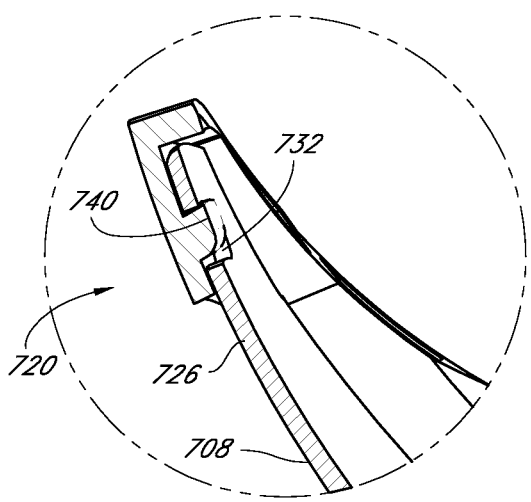
FIG. 32A is an enlarged cross-sectional view of a portion of the goggle shown in FIG. 32.
Figure 32B:
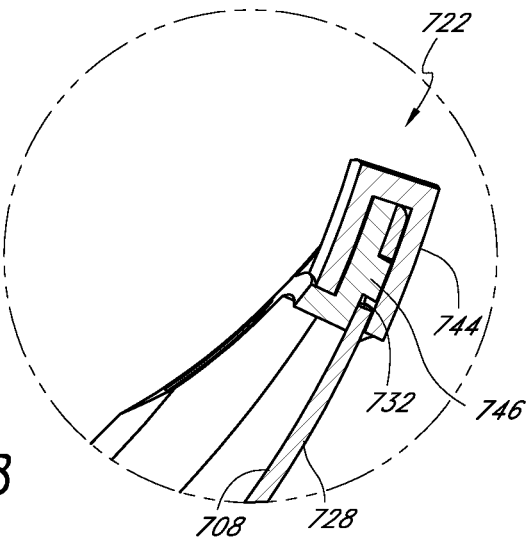
FIG. 32B is another enlarged cross-sectional view of another portion of the goggle shown in FIG. 32.

FIGS. 32-32B are cross-sectional top views of the anterior module 704 of the goggle 700 shown in FIGS. 28-29, taken along the lines 32-32 of FIG. 29. FIG. 32A illustrates the interconnection of the retention socket 720 with the first end 726 of the lens 708. The engagement member 740 of the retention socket 720 can be positioned into engagement with the retention structure 732 of the first end 726 of the lens 708. As shown, the aperture of the retention structure 732 can receive the protrusion of the engagement member 740 in such a manner that the first end 726 is hooked or engaged within the retention socket 720.

For example, the retention structure 732 can be configured to allow the lens 708 to engage with the retention socket 720 at a first rotational position and then to allow the lens 708 to be rotated about a generally horizontal axis until being positioned in a mounted position with respect to the anterior module 704. Once in the mounted position, the first end 726 of the lens 708 can be engaged with the retention socket 720 to prevent side-to-side or anterior-posterior motion of the lens 708. In this manner, the engagement member 740 can resist an anterior force exerted against the lens 708 and thereby prevent substantial movement of the lens 708 relative to the retention socket 720.

FIG. 32B illustrates the interconnection of the retention clip 722 with the second end 728 of the lens 708. The engagement member 746 of the retention clip 722 can be aligned or engaged with the retention structure 732 of the second end 728 of the lens 708. As shown, the aperture of the retention structure 732 can receive the protrusion of the engagement member 746.

The jaw 744 can be rotated, moved, slid, shifted, or translated in order to secure the second end 728 of the lens 708 to the anterior module 704. In some embodiments, the jaw 744 can pivot about a generally horizontal lateral axis and engage at least portion of the lens 708 and at least a portion of the anterior module 704. For example, the jaw 744 can be formed with a U-shaped body that can engage or enclose at least a portion of the second end 728 of the lens 708 and at least a portion of the anterior module 704. The retention structure 732 and the engagement member 746 can be enclosed between anterior and posterior portions of the jaw 744. Further, the jaw 744 can engage anterior and posterior portions of the anterior module 704 and at least a portion of the lens 708.

Thus, the jaw 744 can be rotated to the engaged position such that relative movement between the retention structure 732 and engagement member 746 is prevented. More specifically, with the jaw 744 in the engaged position, the protrusion of the engagement member 746 is unable to exit the aperture of the retention structure 732. Additionally, due to the engagement of the second end 728 of the lens 708 with the anterior module 704, movement or disengagement the first end 726 of the lens 708 with the anterior module 704 will also be prevented. In this manner, the first end 726 and the second end 728 of the lens 708 can be secured relative to the anterior module 704.

In some embodiments, the jaw 744 of the retention clip 722 can be secured in place when moved to the engaged position. For example, the rotatable coupling of the jaw 744 can comprise a recess and protrusion mechanism in which one of the recess and the protrusion rotate relative to the other until the jaw 744 reaches the engaged position, at which time the recess and the protrusion can engage with each other in the mechanism in order to limit or prevent rotational movement of the jaw 744 absent the presence of a significant rotational force. Accordingly, such a mechanism can prevent accidental and unintentional rotation and subsequent disengagement of the jaw 744. Other such mechanisms, including clips, pins, latches, etc., can be incorporated into the retention clip 722 in order to fix the jaw 744 once in the engaged position.

Figure 33:
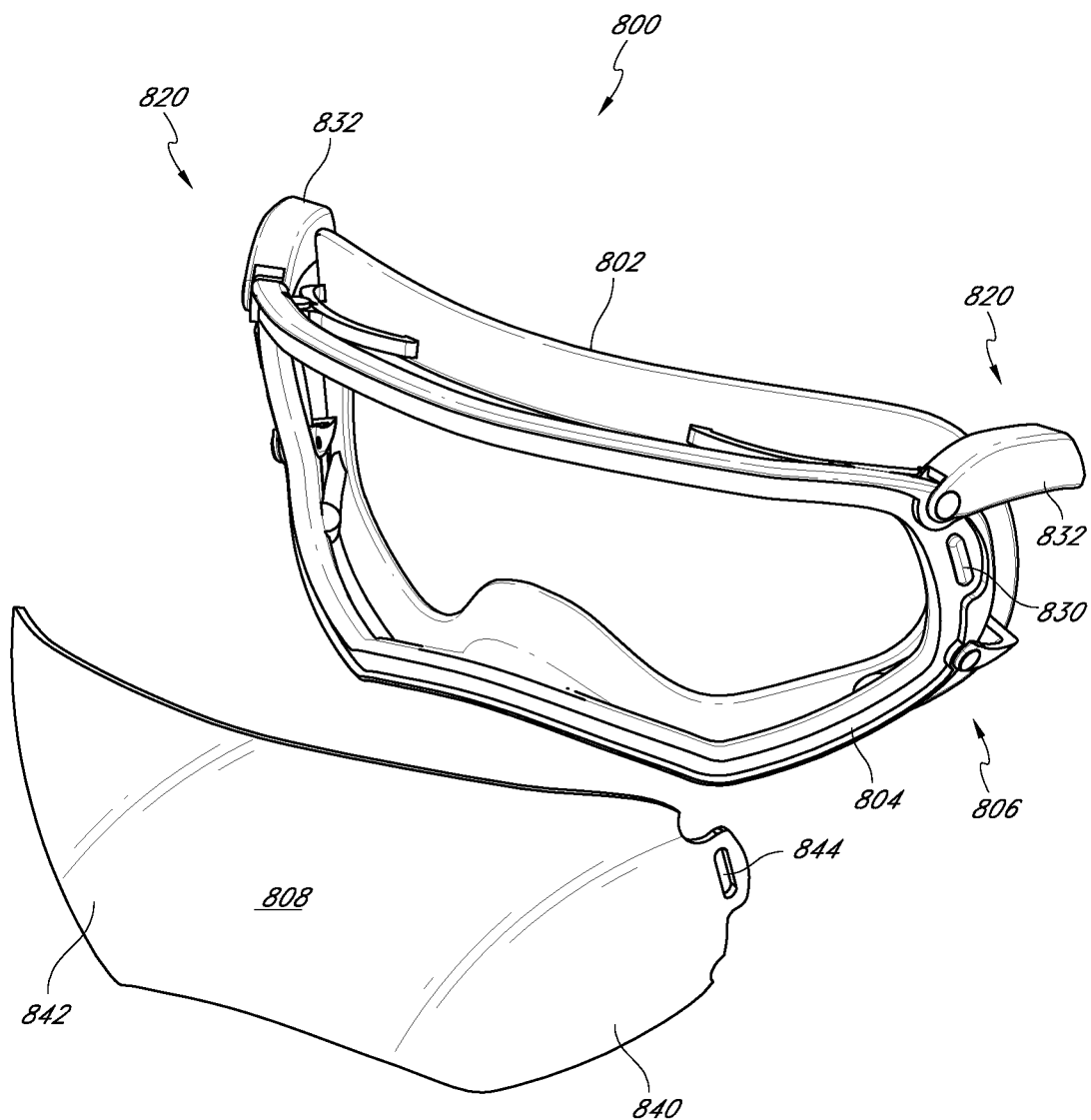
FIG. 33 is a perspective view of a goggle having an interchangeable lens mechanism and an isostatic faceplate wherein the lens is separated from the goggle, according to another embodiment.
Figure 34A:
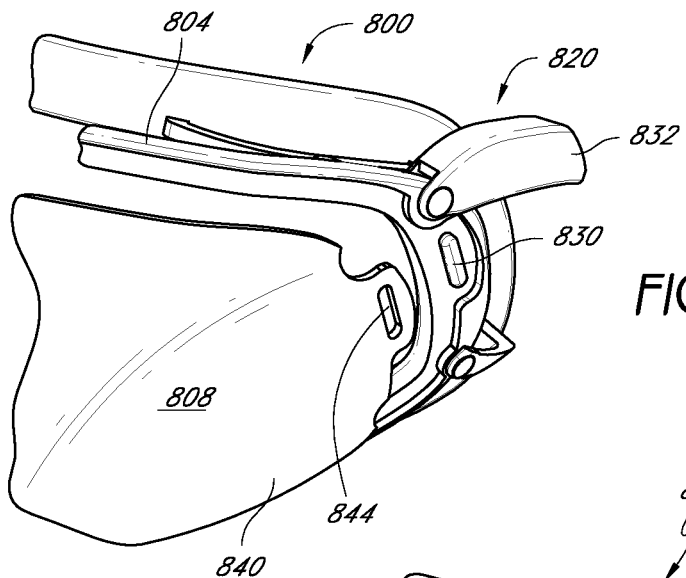
FIG. 34A is a partial perspective view of the goggle shown in FIG. 33 illustrating a second side of the lens is being fitted against the goggle, according to an embodiment.
Figure 34B:
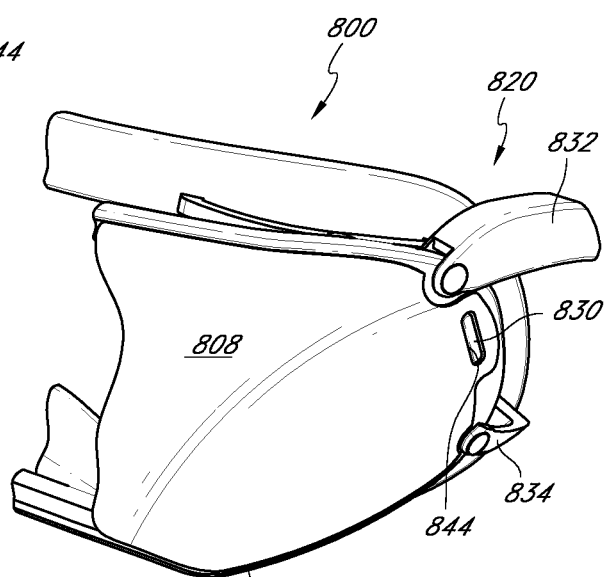
FIG. 34B is a partial perspective view of the goggle shown in FIG. 33 illustrating first and second securing members in disengaged positions, according to an embodiment.
Figure 34C:
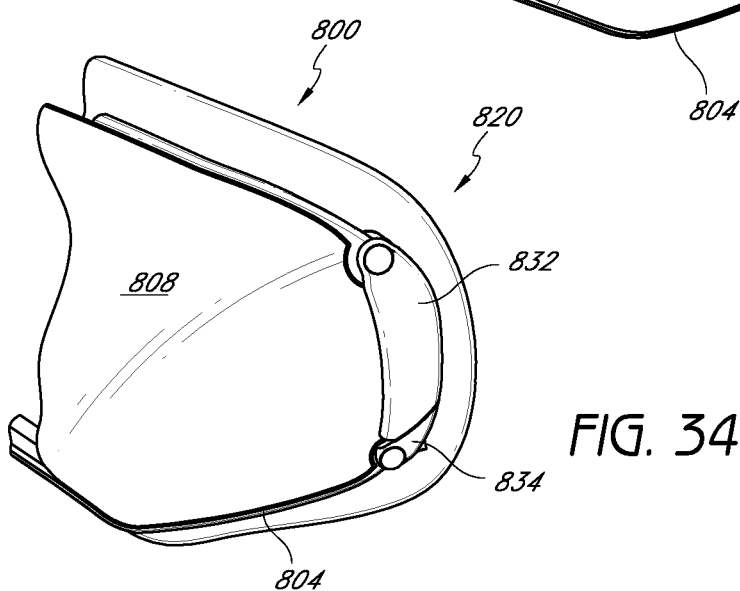
FIG. 34C is a partial perspective view of the goggle shown in FIG. 33 illustrating the first and second securing members in engaged positions, according to an embodiment.

In accordance with another embodiment, FIGS. 33-34C illustrates a goggle 800 having a posterior module 802, and anterior module 804, and an interchangeable lens structure 806 that can accommodate the removal and replacement of a lens 808. Similar to the embodiment of the goggle 700, the interchangeable lens structure 806 of the goggle 800 can comprise mechanisms that facilitate the interconnection of the anterior module 804 with the lens 808. However, in contrast with the goggle 700, the interchangeable lens structure 806 of the goggle 800 can comprise a pair of retention clips 820.

The retention clips 820 can each comprise an engagement member 830, a jaw 832 and a latch 834. The jaw 832 and a latch 834 can be rotatably mounted to the anterior module 804. However, in some embodiments, the jaw 832 and/or the latch 834 can be configured to translate with respect to the anterior module 804 and/or be subsequently attached to the anterior module 804 after the lens 808 is positioned at a mounted position with respect to the anterior module 804.

Similar to the embodiment of the goggle 700, the lens 808 can comprise the first and second ends 840, 842 that each comprise a respective engagement structure 844. The engagement structure 844 can engage or mate with the engagement member 830 of the retention clip 820. The engagement structure 844 can comprise an aperture, and the engagement member 830 can comprise a protrusion. The jaw 832, similar to the jaw 744, can resist relative motion between the engagement structure 844 and the engagement member 830.

The latch 834 can be configured to rotate from an unsecured position to a secured position in which the latch 834 can engage with the jaw 832 in order to prevent accidental or unintentional rotation of the jaw 832. These structures and features of the lens 808 and the retention clip 820 can be modified as discussed above with respect to the lens 708 and the retention clip 722 of the goggle 700; therefore, the discussion of such modifications and features is incorporated herein and will not be repeated for the sake of brevity.

Referring now to FIGS. 34A-C, the mounting an engagement of the lens 808 with the retention clip 820 of the goggle 800 will now be described. As shown in FIG. 34A, the lens 808 is initially moved toward the anterior module 804 of the goggle 800 with the retention clip 820 in a disengaged position. The first end 840 of the lens 808 is positioned such that the engagement structure 844 is mated with the engagement member 830 of the retention clip 820, as shown in FIG. 34B.

Once the lens 808 is in a mounted position as shown in FIG. 34B, the jaw 832 of the retention clip 820 can be moved toward an engaged position, as shown in FIG. 34C. Additionally, the latch 834 of the retention clip 820 can be moved towards the secured position in order to prevent accidental or unintentional rotation of the jaw 832 from the engaged position.

In some embodiments, the latch 834 can mechanically engage with the jaw 832 such that accidental or unintentional rotation of the jaw 832 is prevented. For example, the latch 834 can comprise one or more protrusions and/or recesses that can engage with one or more respective recesses and/or protrusions of the jaw 832. Further, the latch 834 can be biased toward the secured position by means of a spring or the like such that a substantial rotational force must be exerted up on the jaw 832 in order to move the jaw 832 from the engaged position towards a disengaged position. In such embodiments, the latch 834 can facilitate the secure engagement of the lens 808 with the anterior module 804.

As mentioned herein, the quick release lens mechanism can be used in combination with an eyeglass as well as a goggle. The structure of such embodiments comprises the quick release lens mechanism described above and used in combination with an eyeglass frame and at least one eyeglass lens. The eyeglass can comprise dual lenses or a unitary lens. Further, the eyeglass frame can comprise full or partial orbitals. Accordingly, the above discussion will not be repeated here for brevity, but is incorporated by reference hereto for use in eyeglass embodiments.

Rigid Frame Goggle Embodiments

Figure 35:
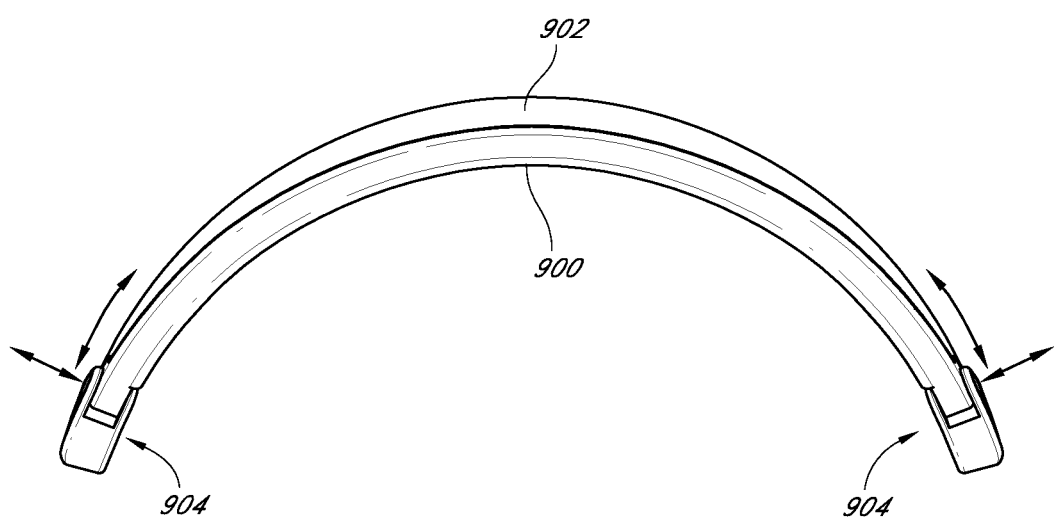
FIG. 35 is a top view schematic diagram of a rigid anterior frame of a goggle, according to an embodiment.
Figure 36:
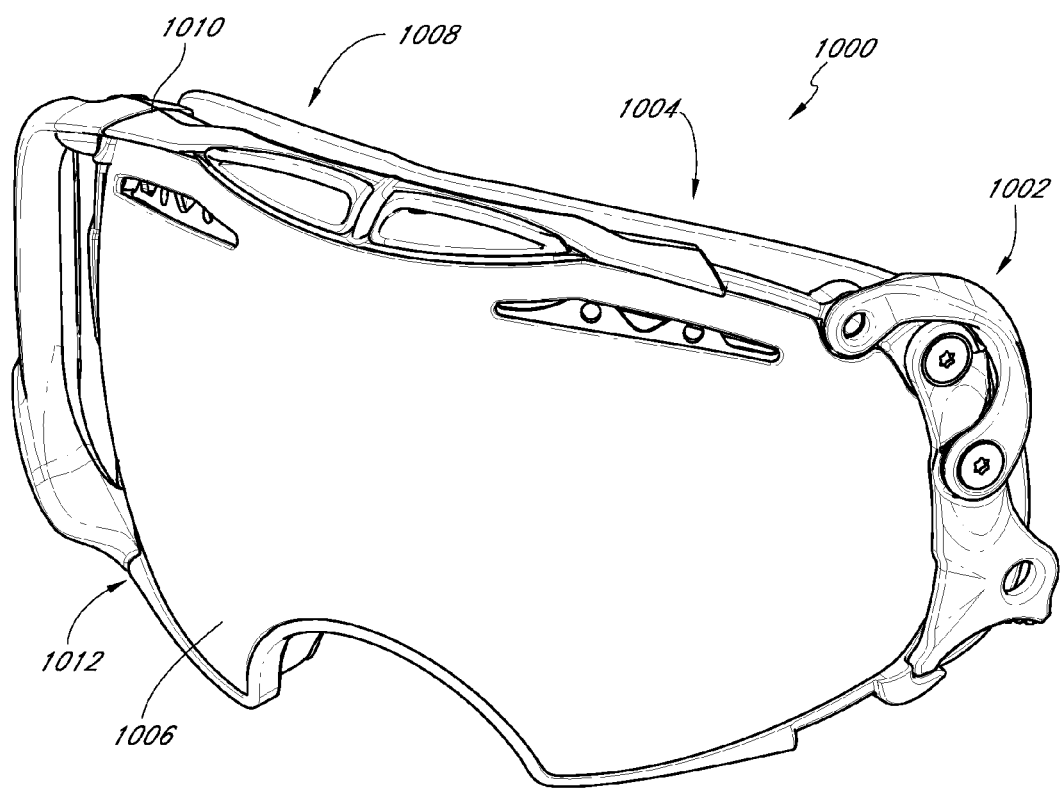
FIG. 36 is a perspective of a goggle, according to another embodiment.

FIG. 35 illustrates a top view of a lens support or anterior module 900 of a goggle. In some embodiments, the anterior module 900 can be formed as a substantially rigid structure. As a substantially rigid structure, the anterior module 900 can support a lens 902 in a manner that prevents the transfer of bending forces or stresses to the lens 902 to prevent any significant deflection of the lens 902.

The term "substantially rigid structure" can encompass embodiments in which the entire anterior module 900 has a constant flexural strength along the width thereof. The term "substantially rigid structure" can also encompass embodiments in which the anterior module 900 has a variable flexural strength along the length thereof, providing desired rigidity at specific portions thereof.

For example, "substantially rigid structure" can encompass an embodiment in which side sections of the anterior module provide a degree of flexibility while a central section of the anterior module is generally inflexible. In some embodiments, the central section of the anterior module can be generally inflexible along a width that can be greater than or equal to about ⅓ of the entire width of the anterior module and/or less than or equal to about ⅘ of the entire width of the anterior module. Further, the central section of the anterior module can be generally inflexible along a width that can be greater than or equal to about ½ of the entire width of the anterior module and/or less than or equal to about ⅔ of the entire width of the anterior module.

Additionally, the term "substantially rigid structure" can also encompass embodiments in which the anterior module is formed from a rigid material, such as a metal or hard plastic, which is generally inflexible under normal flexural stresses of use and handling. However, the term "substantially rigid structure" can also encompass embodiments in which the anterior module is formed from a resilient or elastic material that allows minimal bending, but returns to a default or original configuration when worn.

In some embodiments, the anterior module 900 can have a configuration or contour that matches the configuration or contour of the lens 902 in its as-molded configuration. Thus, the lens 902 can be rigidly supported by the anterior module 900 such that the lens 902 does not deflect from its as-molded configuration, thereby preserving the optical quality of the lens 902.

FIG. 35 illustrates that the anterior module 900 can comprise an interchangeable lens structure 904 disposed at opposing ends of the anterior module 900. In some embodiments, the interchangeable lens structure 904 can be disposed at top and/or bottom portions of the anterior module 900 or along other places thereof. Accordingly, the lens 902 can be replaced and securely retained by the anterior module 900 by virtue of the interchangeable lens structure 904.

Further Embodiments

FIGS. 36-51 illustrate an embodiment of eyewear that can incorporate various features and components discussed herein. The embodiment of the eyewear shown in these figures is illustrated as a goggle, but other forms of eyewear, such as eyeglasses, can also incorporate or omit the features discussed with respect to this embodiment, as well as incorporate or omit other features of other embodiments discussed herein.

Referring now to FIGS. 36-39, an embodiment of a goggle 1000 is provided that can comprise various features and advantages of the aforementioned embodiments, as well as other features discussed further below. For example, the goggle 1000 can comprise an engagement mechanism 1002, an isostatic posterior frame component 1004, a lens or lens assembly 1006, an anti-fog Venturi airflow system 1008, a rigid frame 1010, and a modular frame 1012. These features can be interchangeably incorporated into various embodiments, and the embodiment shown in FIGS. 36-51 is provided for illustrative purposes only.

Figure 37:
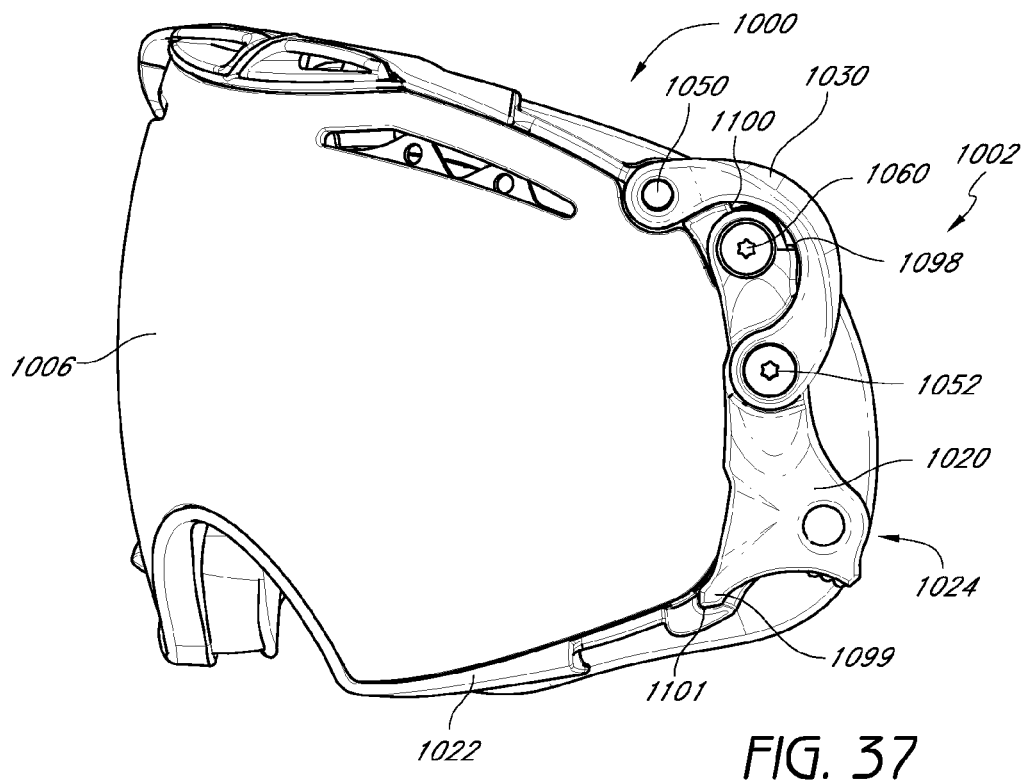
FIG. 37 is a side perspective view of the goggle shown in FIG. 36, wherein an engagement mechanism of the goggle is in a closed position.

FIG. 37 is a side view of the goggle 1000 illustrating the engagement mechanism 1002. The engagement mechanism 1002 can comprise a latch member or clip 1020. The latch member 1020 can be movably coupled to an anterior module or frame 1022 of the goggle 1000 in order to facilitate engagement between the goggle 1000 and the lens assembly 1006. The latch member 1020 can move between a closed position 1024 and an open position 1026 (shown in FIG. 38). In some embodiments, the latch member 1020 can be pivotably coupled to the frame 1022. However, the latch member 1020 can also be slidably coupled to the frame 1022.

In some embodiments, the engagement mechanism 1002 can also comprise a biasing component. The biasing component can be configured to urge the latch member 1020 toward the closed position 1024 to secure the lens assembly 1006 relative to the goggle 1000. Further, the biasing component can operate as a bistable mechanism to urge the latch member 1020 toward either the closed position 1024 or the open position 1026.

As shown in FIGS. 36-40C, the biasing component can comprise a deflectable component, such as a link 1030. For example, the biasing component can deflect from an undeflected or at-rest position to a deflected or stressed position. When moved, compressed, or deflected to the stressed or deflected position by a given force, the biasing component can store potential energy that can be exerted to move the engagement mechanism 1002 toward the closed position 1024 or the open position 1026. In the embodiment illustrated in FIGS. 36-40C, the biasing component is shown as the link 1030, which is in the form of an arcuate elongate body. The biasing component can comprise various structures, such as a spring, a band, link, or other structure that can store potential energy during movement, compression, or deflection thereof.

Figures 40A, 40B:
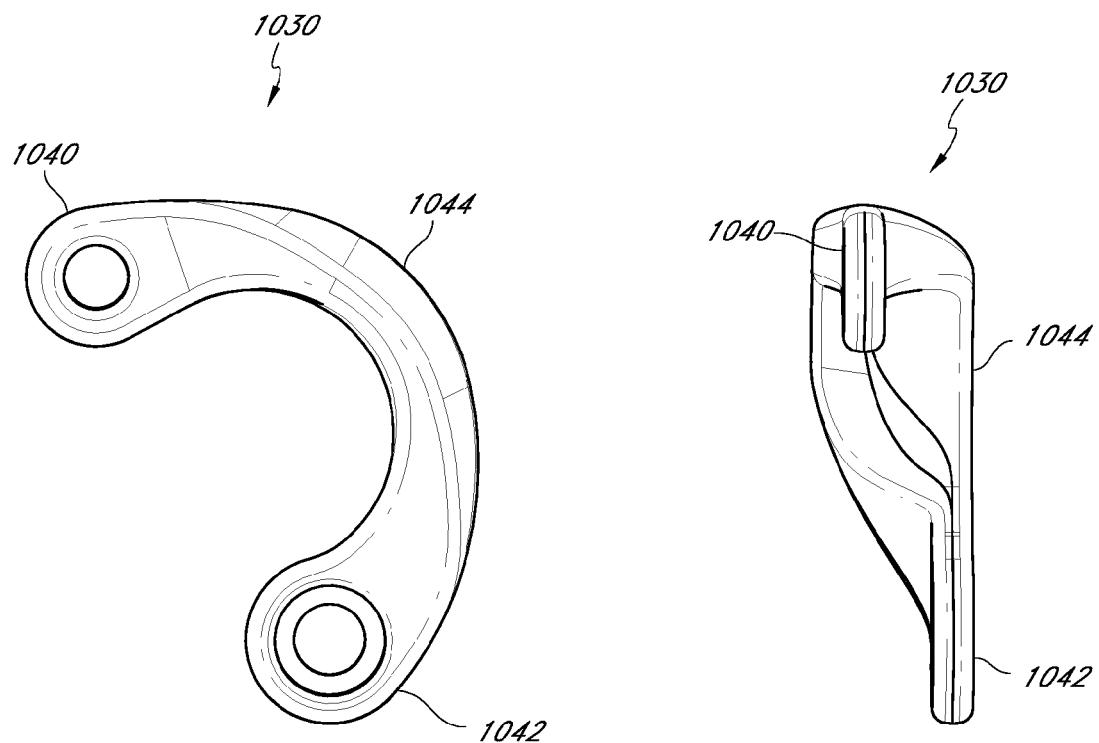
FIG. 40A is a side view of a biasing mechanism of the goggle shown in FIG. 36, according to an embodiment.
FIG. 40B is an end view of the biasing mechanism shown in FIG. 40A.
Figure 40C:
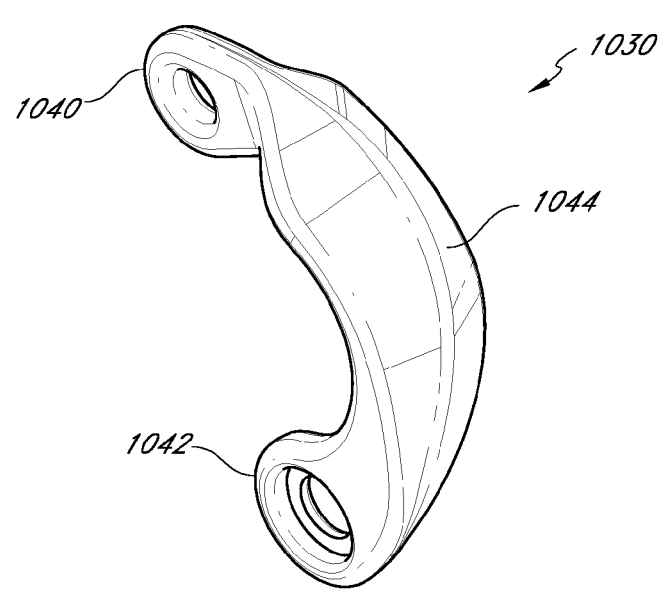
FIG. 40C is a perspective view of the biasing mechanism shown in FIG. 40A.

FIGS. 40A-40C illustrate that an embodiment of the link 1030 can comprise the first and second ends 1040, 1042 that can be interconnected with a portion of the goggles 1000 and a portion of the latch member 1020, respectively. The link 1030 can comprise apertures disposed at the first and second ends 1040, 1042 thereof that enable the link 1030 to be interconnected in use.

In the illustrated embodiment, the link 1030 is configured as a monolithic structure. The link 1030 can comprise a deflectable core or body 1044 to enable the link 1030 to provide a biasing force to the latch member 1020. For example, the link 1030 can provide a virtual pivot or living hinge for the latch member 1020. The body 1044 can define a variable profile in order to provide a desired degree of resistance to deflection. For example, the body 1044 can define flattened central section to facilitate bending of the link 1030 and provide a desired degree of resistance to deflection. In some embodiments, central section of the body 1044 can be flattened in a direction generally parallel to a bending axis. Further, the end portions of the body 1044 can be flattened in a direction generally transverse or oblique relative to the bending axis in order to reduce and/or prevent bending at the end portions. The variable profile or tapered dimensions of the link 1030 can allow the body 1044 of the link 1030 to be manufactured from a single material while providing desired strength characteristics. However, in some embodiments, the link 1030 can be configured as a monolithic unit or structure having a generally constant cross-sectional profile along the body 1044 or thereof. In such embodiments, the material forming the link 1030 can be selected to provide desired strength characteristics.

However, in some embodiments, the link 1030 can also be formed from a plurality of materials or separate parts. For example, the first and second ends 1040, 1042 of the link 1030 can be formed from a generally rigid material while the body 1044 of the link 1030 comprises a different material that is generally deflectable in order to allow the link 1030 to provide a desired biasing function.

The link 1030 can be formed from a variety of materials, including plastics, metals, composites, and the like. In some embodiments, the link 1030 can be formed using an injection molding process. Other processes such as overmolding, casting, and the like can be used to form the link 1030, whether as a monolithic structure or an assembly and whether formed from a single material or multiple materials.

Referring again to FIGS. 37-39, the link 1030 can be coupled to the frame 1022 and the latch member 1020 at first and second connection points 1050, 1052. The first connection point 1050 can be located along the frame 1022. For example, the first connection point 1050 can be configured as an aperture extending through the frame 1022. The second connection point 1052 can be located along the latch member 1020. For example, the second connection point 1052 can comprise an aperture extending through an intermediate portion of the latch member 1020. The goggle 1000 can be configured such that the spacing of the first connection point 1050 from the second connection point 1052 varies when the latch member 1020 is pivoted between the closed position 1024, an intermediate open position (not shown), and the open position 1026.

Figure 38:
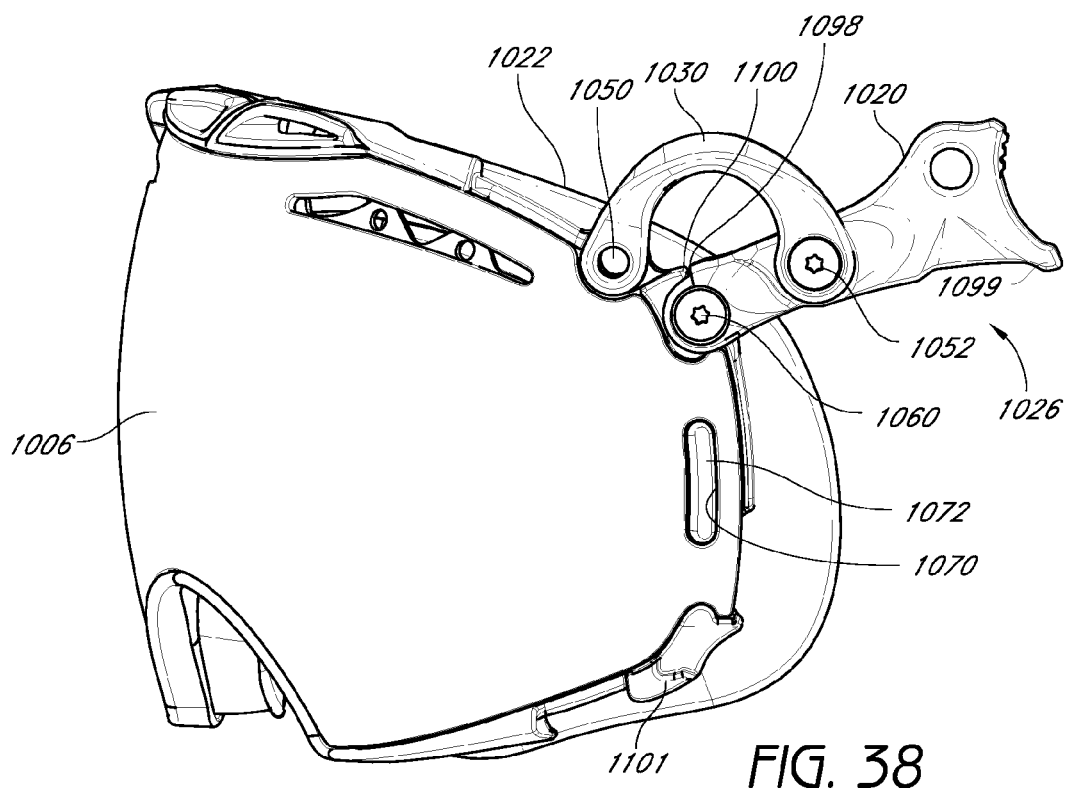
FIG. 38 is a side perspective view of the goggle shown in FIG. 36, wherein the engagement mechanism of the goggle is in an open position.
Figure 39:
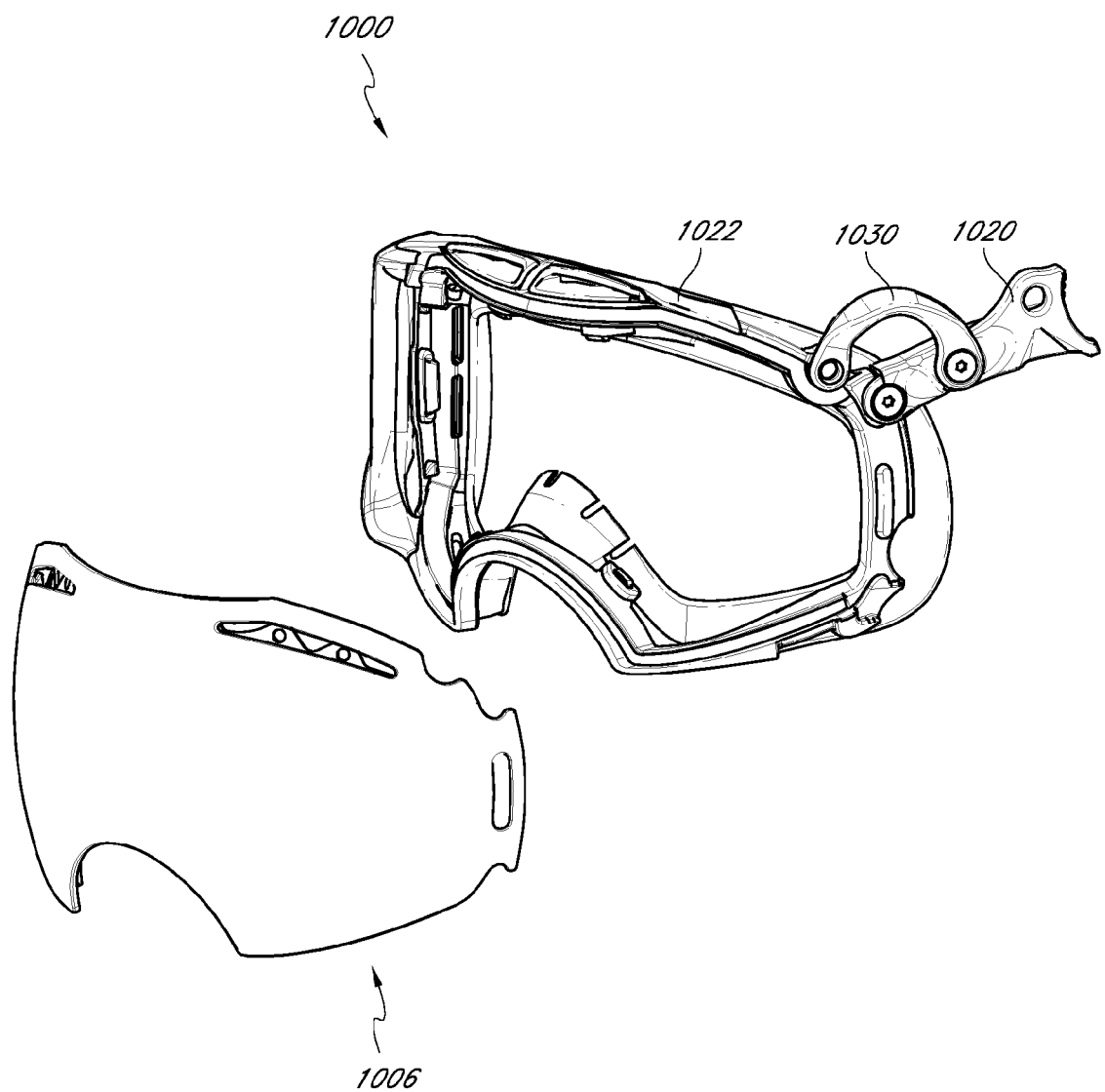
FIG. 39 is a perspective view of the goggle shown in FIG. 36, wherein the engagement mechanism is in the open position and a lens assembly of the goggle is separated from the goggle.

For example, a pivot connection point 1060 between the latch member 1020 and the frame 1022 can be positioned relative to the first and second connection points 1050, 1052 so as to cause separation of the first and second connection points 1050, 1052 as the latch member 1020 pivots relative to the frame 1022. For example, the first and second connection points 1050, 1052 can define a linear path and a first direct, linear distance therebetween when the latch member 1020 is in the closed position 1024. As shown in FIGS. 37-38, the pivot connection point 1060 can be offset or spaced apart from the linear path of the first and second connection points 1050, 1052 when the latch member 1020 is in the closed position 1024. The motion of the second connection point 1052 occurs along an arcuate path defined by the distance (or radius) between the pivot connection point 1060 and the second connection point 1052. Further, during movement of the latch member 1020, although the distance between the first connection point 1050 and the pivot connection point 1060 does not change, the direct, linear distance between the first and second connection points 1050, 1052 will increase as the second connection point 1052 moves along the arcuate path as the latch member 1020 pivots.

In some embodiments, the increase in the direct, linear distance between the first and second connection points 1050, 1052 can result in a stretching or deflection of the link 1030 as the first and second connection points 1050, 1052 move apart. The link 1030 can be configured to resist the stretching or deflection and tend to urge the latch member to the closed and/or open position 1024, 1026 as the link 1030 seeks to return to a non-stressed position. Accordingly, the link 1030 can tend to exert a biasing force that urges the latch member 1020 toward the closed and/or open position 1024, 1026.

FIGS. 37 and 38 illustrate the offset positioning of the pivot connection point 1060 from the linear path defined by the first and second connection points 1050, 1052. An intermediate position (not shown) between the open and closed positions 1024, 1026 could be reached when the pivot connection point 1060 is linearly aligned with the first and second connection points 1050, 1052. In such an intermediate position, the distance between the first and second connection points 1050, 1052 would be maximized, also resulting in a maximum potential energy in the link 1030.

In some embodiments, the spacing or linear distance of the first and second connection points 1050, 1052 can be generally equal to the linear distance between the apertures of the first and second ends 1040, 1042 of the link 1030 when the link 1030 is in the undeflected or at-rest position (i.e., when the latch member 1020 is in the closed position 1024). However, in some embodiments, the spacing or linear distance of the first and second connection points 1050, 1052 can be generally greater than the linear distance between the apertures of the first and second ends 1040, 1042 of the link 1030 when the link 1030 is in the undeflected or at-rest position (i.e., when the latch member 1020 is in the closed position 1024). Thus, the link 1030 can be in a generally stressed or deflected state when the latch member 1020 is in the closed or open positions 1024, 1026. In such embodiments, a closing or opening force can be continually applied by the link 1030 in order to maintain the latch member 1020 securely in the open or closed position 1024, 1026.

As noted above with respect to FIGS. 28-34C, the goggle 1000 can also comprise an interchangeable lens structure in which the lens or lens assembly 1006 comprises at least one retention structure 1070 and the frame 1022 comprises at least one corresponding engagement member 1072. Further, the opposite ends of the lens or lens assembly 1006 and the frame 1022 can be configured to include a retention structure and/or an engagement member to facilitate interconnection of the opposite end of the lens assembly 1006 with the opposite end of the frame 1022.

As similarly discussed above, FIGS. 37-39 illustrate that when the opposite end of the lens assembly 1006 is properly seated against the frame 1022, the retention structure 1070 can be fitted over the engagement member 1072, and the latch member 1020 can be moved down into the closed position 1024 to engage and secure the lens assembly 1006 relative to the frame 1022. The above discussion regarding these features is incorporated herein by reference and the discussion will not be repeated here.

Figure 41A:
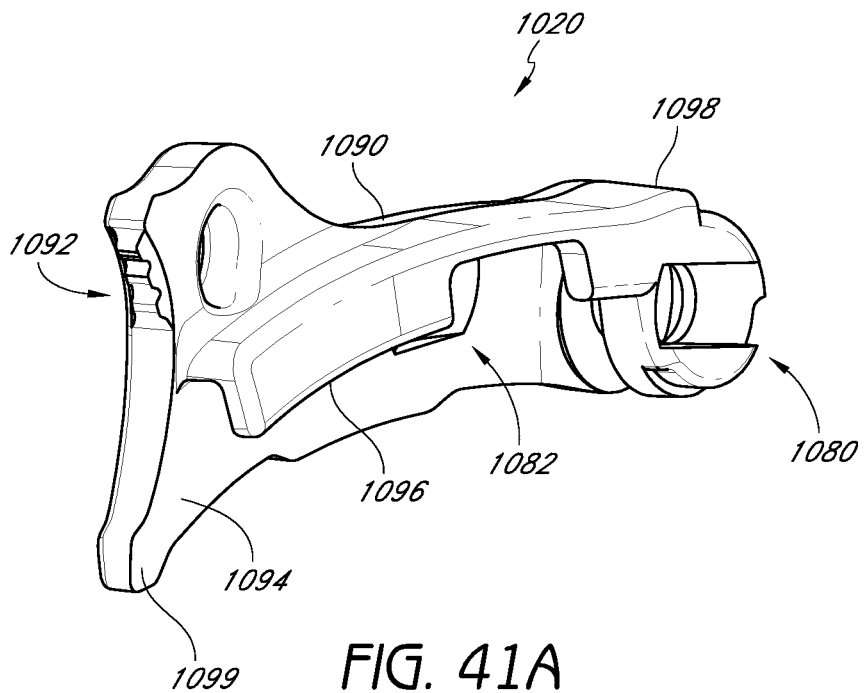
FIG. 41A is a rear perspective view of a latch mechanism of the goggle shown in FIG. 36, according to an embodiment.
Figure 41B:
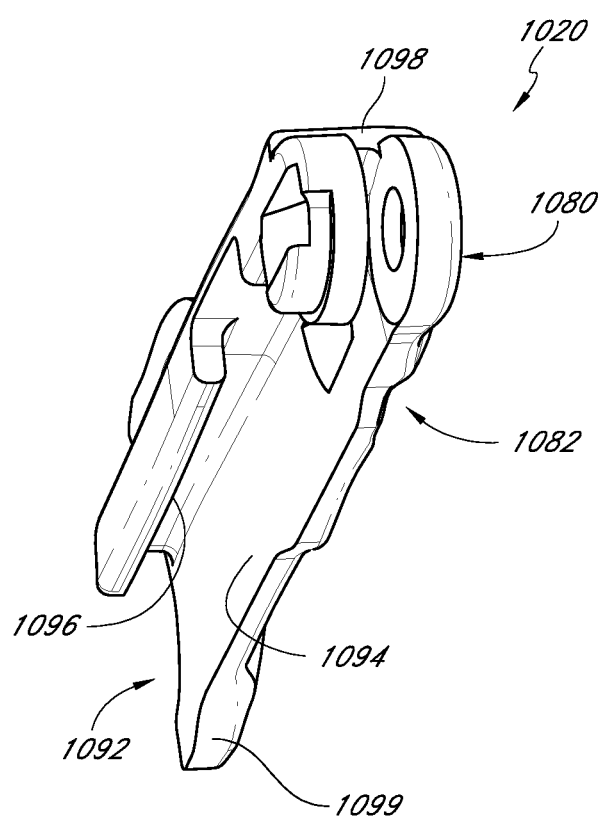
FIG. 41B is a front perspective view of the latch mechanism shown in FIG. 41A.

Referring now to FIGS. 41A-B, an embodiment of the latch member 1020 is illustrated. The latch member 1020 can comprise first and second coupling points 1080, 1082. The latch member 1020 can be coupled to the frame 1022 at the first coupling point 1080. Additionally, the latch member 1020 can be coupled with the biasing component or link 1030 at the second coupling point 1082. The latch member 1020 can also comprise a body 1090 having an actuating portion 1092 that can be configured to allow the wearer to grip and adjust the position of the latch member 1020 relative to the frame 1022.

In some embodiments, the body 1090 of the latch member 1020 can also comprise a first flange 1094. The first flange 1094 can overlap the lens assembly 1006 and the engagement member 1072 of the frame 1022 when the latch member 1020 is positioned in the closed position 1024. The body 1090 of the latch member 1020 can also comprise a second flange 1096. The second flange 1096 can be configured to engage a portion of the frame 1022 when the latch member 1020 is in the closed position 1024. Accordingly, the first and second flanges 1094, 1096 can be used to receive at least a portion of the lens assembly 1006 and at least a portion of the frame 1022 by capturing or sandwiching the lens assembly 1006 and the frame 1022 to secure the relative positioning of the lens assembly 1006 and the frame 1022.

Additionally, the body 1090 of the latch member 1020 can comprise a stop mechanism 1098. As shown in FIGS. 37-38, the stop mechanism 1098 can interact with a ledge 1100 formed on the frame 1022 to restrict rotational movement of the latch member 1020. For example, as the latch member 1020 rotates upwardly to the open position 1026, the stop mechanism 1098 can contact the ledge 1100 to limit further rotation of the latch member 1020 relative to the frame 1022. Advantageously, in some embodiments of the latch member 1020, the position of the stop mechanism 1098 can be varied in order to adjust the rotational orientation of the open position 1026.

In order to achieve a desired articulation and closing or opening force of the latch member 1020, the spacing and configuration of the components of the engagement mechanism 1002 can be varied. Further, the latch member 1020 and/or the frame 1022 can comprise a locking structure or component 1099. The locking structure 1099 can interact with the frame 1022 to provide an additional securing force between the latch member 1020 and the frame 1022 when the latch member 1020 is in the closed position 1024. For example, the locking structure 1099 can be formed as a protrusion along an edge or surface of the latch member 1020. Further, an engaging portion 1101 of the frame 1022, such as a ledge, protrusion, or recess, can engage with the locking structure 1099 when the latch member 1020 is in the closed position 1024 to secure the latch member 1020 in the closed position 1024.

Figure 42:
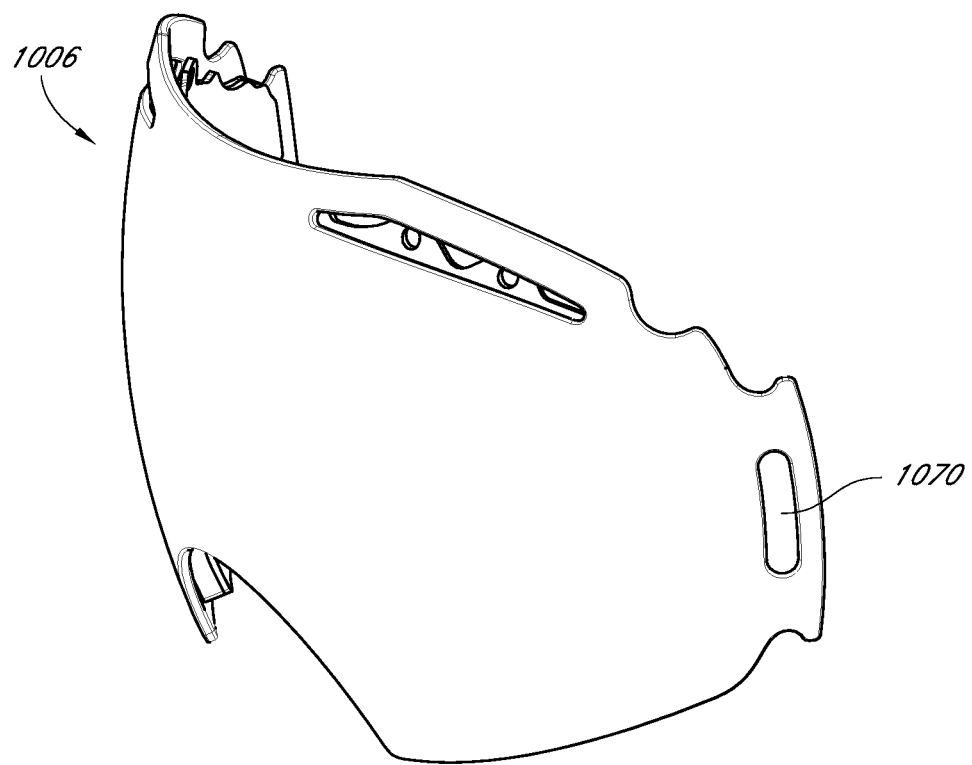
FIG. 42 is a perspective view of the lens assembly of the goggle shown in FIG. 36, according to an embodiment.
Figure 43:
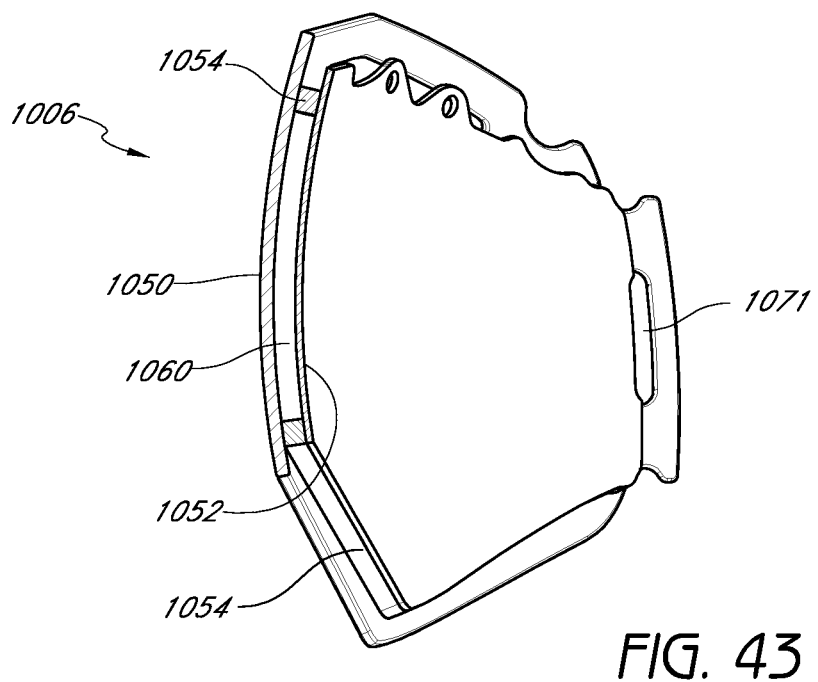
FIG. 43 is a cross-sectional side view of the lens assembly shown in FIG. 42.

Although some embodiments can use a single lens, some embodiments can use a lens assembly comprising two or more components and/or lenses. For example, FIGS. 42-43 illustrate an embodiment of a lens assembly 1006 that can be used in some embodiments. The lens assembly 1006 can comprise an outer lens 1050 and an inner lens 1052. In some embodiments, the outer and inner lenses 1050, 1052 can be spaced apart by a gasket component 1054 to create a gap 1060 between the lenses 1050, 1052. The gasket 1054 can extend about a periphery of the lenses 1050, 1052. Further, the outer lens 1050 can be configured to comprise retention structures 1070, 1071 by which the lens assembly 1006 can be coupled to the goggle. The retention structures 1070, 1071 can be disposed on opposing lateral ends of the lens assembly 1006.

The gasket 1054 can comprise one or more discontinuities to permit airflow into the gap 1060. However, the gasket 1054 can also extend continuously or unbroken about the periphery of the lenses 1050, 1052 such that the gap 1060 forms a sealed or enclosed pocket of air. The gasket 1054 can comprise a breathable or open cell material that allows air passage through the gasket 1054. Further, the gasket 1054 can comprise a non-breathable or closed cell material that tends to prevent air passage therethrough. In some embodiments, the gasket 1054 can comprise breathable and non-breathable portions.

The gap 1060 created between the lenses can facilitate ventilation, anti-fogging, and/or create an insulative effect by trapping a pocket of air between the outer and inner lenses 1050, 1052. For example, an enclosed pocket of air can maintain an intermediate temperature which, in some conditions, can bridge a temperature differential between the air temperature adjacent the wearer's face and the air temperature outside the goggle.

During use, the inner lens 1052 can be compressed against the goggle frame when the lens assembly 1006 is coupled to the goggle. In some embodiments, the inner lens 1052 can form a seal against the goggle frame to maintain a desired air flow or ventilation through the frame, as discussed below.

Figure 44:
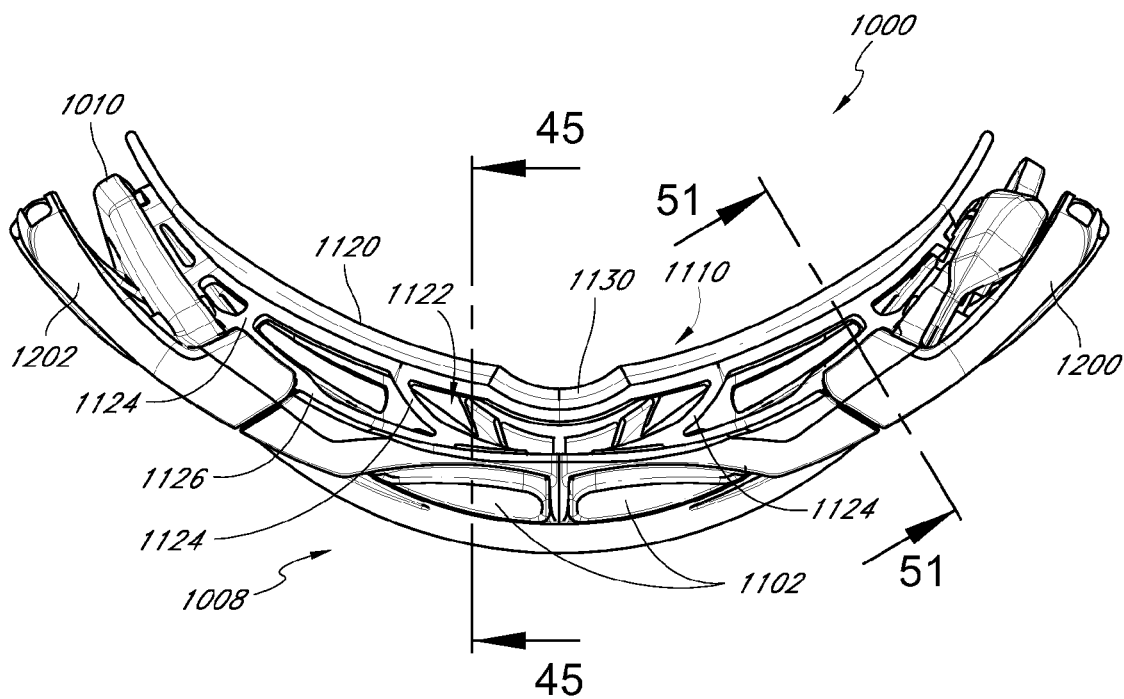
FIG. 44 is a top view of the goggle shown in FIG. 36, according to an embodiment.
Figure 45:
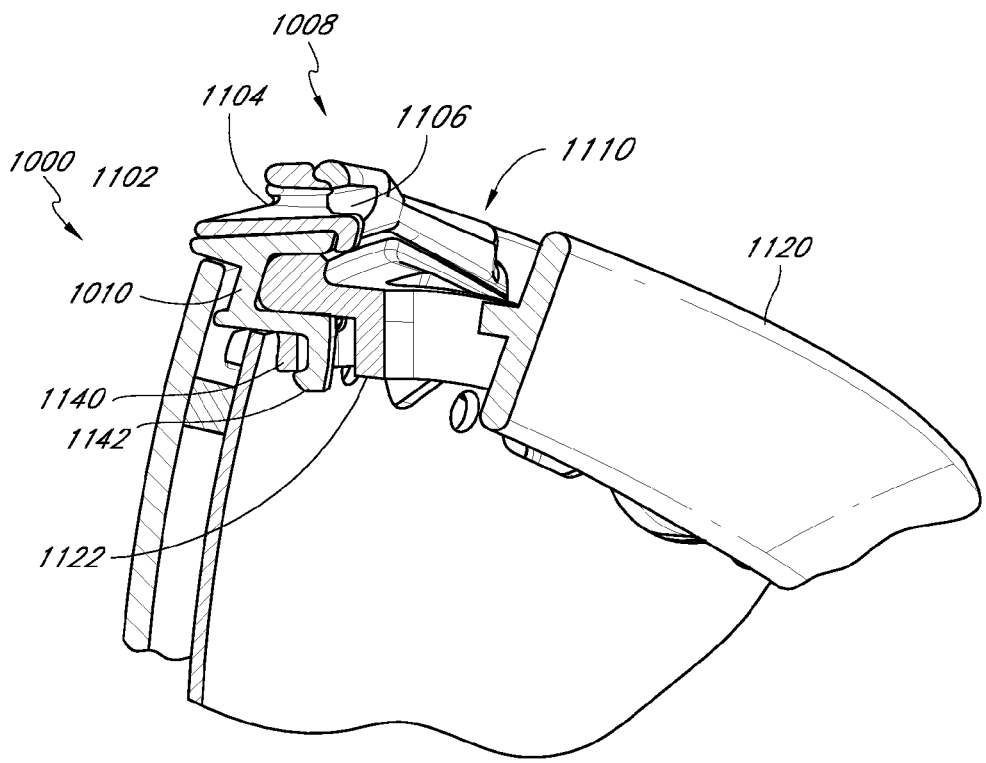
FIG. 45 is a cross-sectional side view of the goggle taken along section lines 45-45 of FIG. 44.

Referring now to FIGS. 44-45, the goggle 1000 can comprise an anti-fog Venturi airflow system 1008. The airflow system 1008 can comprise one or more ports 1102 disposed along a periphery of the goggle 1000. The port(s) 1102 can be disposed along a central section of the goggle 1000 along an upper portion thereof. The port(s) 1102 can comprise an anterior end 1104 that is open toward the anterior direction of the goggle 1000 and a posterior end 1106 that is open toward a posterior section of the goggle 1000.

In use, air can flow into the anterior end 1104 of the port 1102 and out through the posterior end 1106. The air flow can exhibit the velocity and pressure qualities produced as a result of the Venturi effect. A pressure differential can exist between the outer portions of the goggle and the port(s) 1102. Air can be drawn into the port(s) 1102 and pass over a suspension or interconnection portion 1110 of the goggle 1000. In some embodiments, the interconnection portion 1110 can comprise a foam or air permeable membrane (not shown) that covers the suspension or interconnection portion 1110 to prevent ingress of particulate into the interior of the goggle 1000. The air passing through the port(s) 1102 can pass over the membrane and provide enhanced ventilation and defogging for the goggle 1000. In some embodiments, the Venturi effect can contribute to a negative pressure being created in the interior of the goggle to induce airflow therethrough and reduce fogging. Such embodiments can thus provide improved ventilation and defogging compared to prior art goggles that do not comprise an airflow system.

In embodiments of the goggle having an isostatic posterior frame component 1004, the goggle 1000 can further comprise means for allowing further adjustability of the faceplate to conform to larger or smaller head sizes. For example, FIG. 44 illustrates that the posterior frame component 1004 can comprise a posterior faceplate 1120 and an isostatic mechanism 1122. The posterior faceplate 1120 can comprise a generally flat surface that extends about the periphery of the faceplate 1120 and can further comprise at least one flexible portion 1130. The flexible portion 1130 can give the posterior faceplate 1120 additional width adaptability to adjust to a given size and shape of a wearer's face. Thus, the generally flat surfaces of the posterior faceplate 1120 position on either side of the flexible portion 1130 can be spread or displaced from each other in order to accommodate a given head shape. For example, the flexible portion 1130 can allow opposing sides of the faceplate 1120 to be stretched apart from each other in an additional amount that allows the faceplate 1120 to accommodate larger head sizes. The additional amount of stretching or displacement is determined by the geometry and length of the flexible portion 1130.

For example, the flexible portion 1130 can be formed as a recessed or curved portion along the faceplate 1120. The flexible portion 1130 can deviate from the curvature on either side of the faceplate 1120. As the faceplate 1120 is flattened to accommodate a wide head size, the flexible portion 1130 can also flatten to allow increased coverage and adjustability of the faceplate 1120. Further, for smaller head sizes, the flexible portion 1130 can collapse into itself to allow the faceplate 1120 to be adjusted to tighter dimensions. Accordingly, the shape of the flexible portion 1130 can allow the faceplate 1120 to adjust to a variety of head shapes and sizes more so than a faceplate without a flexible portion.

Further, in some embodiments, the shape of the flexible portion 1130 can also be used to achieve a desired air flow into the interior of the goggle 1000, as desired. One or more of the flexible portions 1130 can be used for facilitating air flow and/or adjustability of the faceplate 1120.

The isostatic mechanism 1122 can comprise a plurality of connectors 1124 that extend from an anterior portion 1126 of the posterior frame component 1004. The connectors 1124 can be formed from a compressible or flexible material. For example, the connectors 1124 can be deflected such that the faceplate 1120 can be deformed to accommodate a given head shape. The connectors 1124 can be positioned generally equidistant from a centerline of the goggle 1000. As illustrated, the connectors 1124 can be positioned at the upper rim or edge of the goggle 1000; however, the connectors can also be positioned along a lower rim or edge of the goggle 1000.

Additionally, the isostatic mechanism 1122 can be integrally or monolithically formed with the faceplate 1120 such that these components form a single-piece unit. For example, in some embodiments, a desirably flexible material can be used to fabricate both be isostatic mechanism 1122 and the faceplate 1120. This can advantageously reduce the manufacturing time and cost, as well as simplify the assembly process. Accordingly, the goggle 1000 can be easily modularly formed using an economy of individual components that are interchangeable according to wearer preferences, as discussed further herein.

Embodiments of the goggle can also be formed modularly with wearer-interchangeable components that can be interconnected and secured together by using a wearer-actuatable fastener or fastening mechanism. In some embodiments, the wearer-actuatable fastening mechanism can be defined as a fastener or fastening mechanism that can be manually actuated between engaged and disengaged states by the wearer. Wearer-actuatable fasteners or fastening mechanisms may be actuated without requiring the use of specialized tools; however, it is contemplated that basic tools, such as a screwdriver, may be used to facilitate actuation. In some embodiments, a wearer-actuatable fastener or fastening mechanism can be actuated by hand, without tools. Further, some embodiments of the goggle can be modularly interchangeable and secured together without permanent or single-use fasteners, such as adhesives and some mechanical fasteners, including screws, bolts, adhesives, and the like.

For example, the embodiment of FIGS. 44-51 illustrates that the goggle 1000 can comprise first and second outriggers 1200, 1202. The outriggers 1200, 1202 can be removably coupled to the goggle 1000 and facilitate interconnection of the components of the goggle 1000 with each other. In the illustrated embodiment, the anterior module or frame portion 1022 of the goggle can be fastened or coupled to a posterior module or frame portion 1212 using the outriggers 1200, 1202. As discussed further below, the coupling formed by the outriggers 1200, 1202 with the goggle 1000 can be achieved by the wearer by manipulating the components by hand. Thus, the components of the goggle 1000 can be interchanged by the wearer without requiring the use of specialized tools, single-use fasteners or permanent fasteners.

In some embodiments, the outriggers can function as the primary means of coupling or attaching the anterior and posterior modules, such as between a lens support, an isostatic mechanism, and/or a faceplate. However, in some embodiments, a secondary means of coupling or attaching can be employed. A secondary means of coupling or attaching can comprise a snap-fit member, hook and loop member, and/or other types of interference fit or frictional engagement members.

Figure 46:
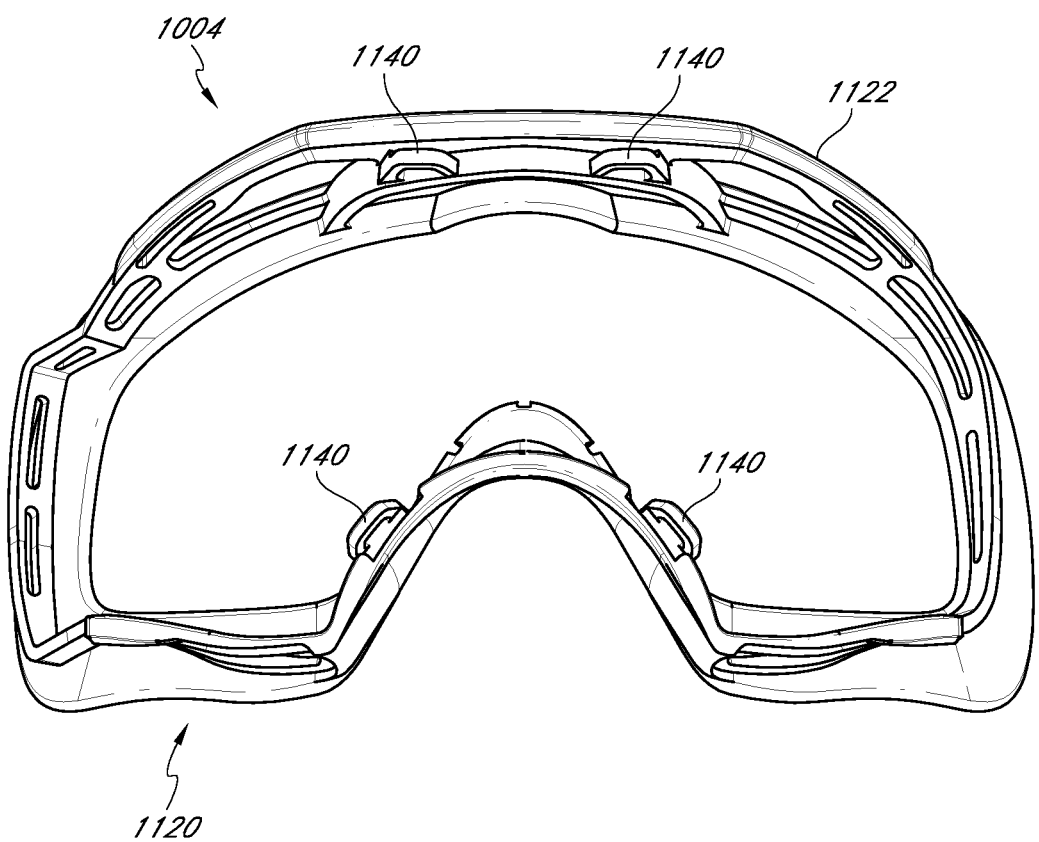
FIG. 46 is a front perspective view of an isostatic posterior frame component of the goggle shown in FIG. 36, according to an embodiment.
Figure 47:
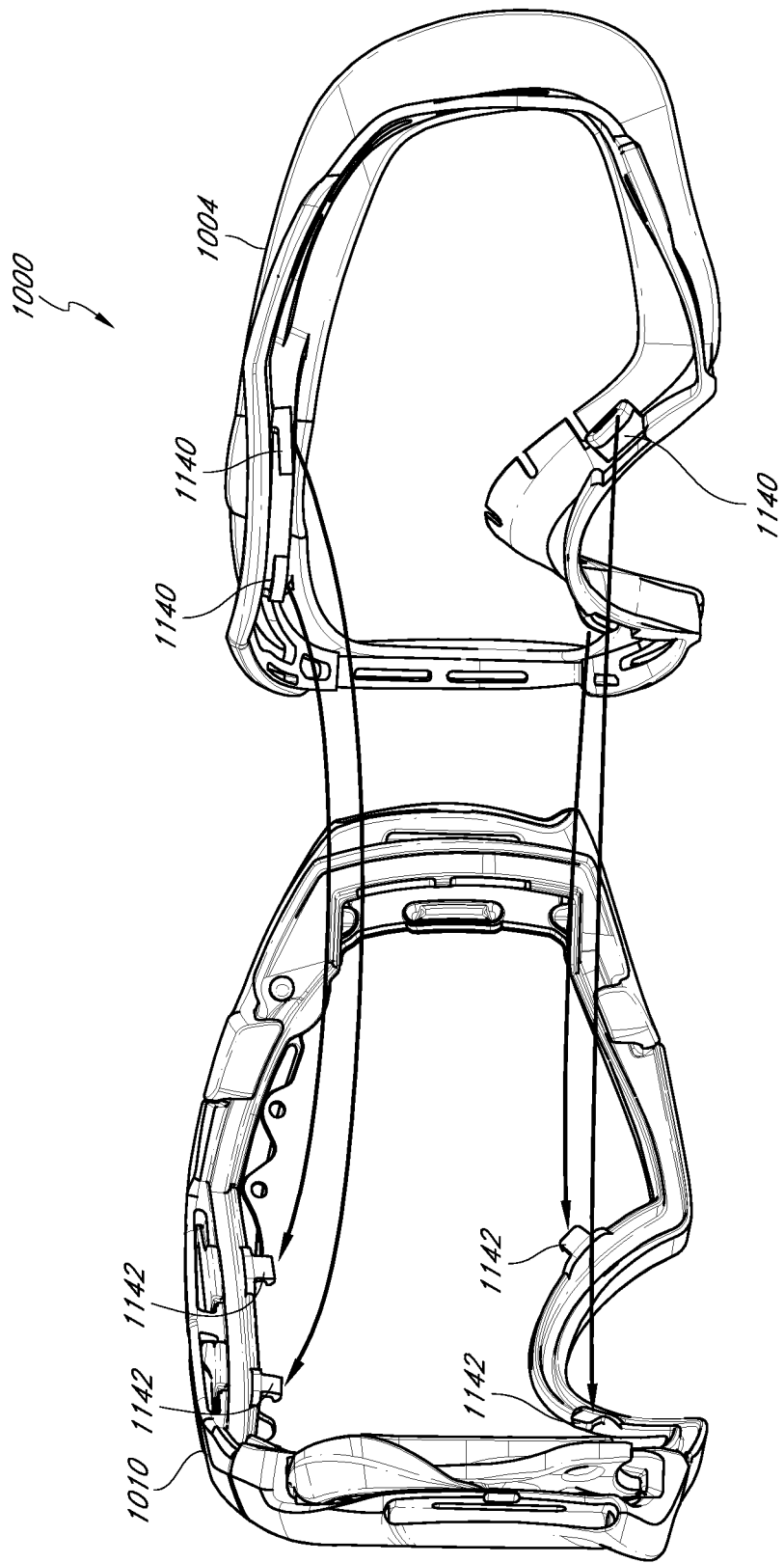
FIG. 47 is a side perspective view illustrating secondary or initial attachment of the isostatic posterior frame component of FIG. 46 with a frame of the goggle shown in FIG. 36, according to an embodiment.

For example, as shown in FIGS. 46-47, the posterior frame component 1004 can comprise on or more fastening members 1140 configured to engage with a corresponding fastening member 1142 of the frame 1010. The fastening members 1140, 1142 can comprise hooks and loops that are formed on the respective ones of the posterior frame component 1004 and the frame 1010. The arrows in FIG. 47 illustrate the general mating arrangement of the fastening members 1140, 1142. These components can be reversed in some embodiments, such that the posterior frame component 1004 comprises one or more protrusions or hooks that can mate with one or more apertures or loops formed on the frame 1010. Further, other structures can be used, including the snap-fit members, protrusions, slots, channels, apertures, plugs, loops, whether deformable, deflectable, compressible, incompressible, or rigid. Such structures can be formed monolithically with the respective part such that the structures and the part form a single, continuous part. However, the structures can also be separately attached to the respective part. As illustrated in FIG. 46, in some embodiments, the fastening members 1140 can be formed monolithically with the posterior frame component 1004. This can advantageously reduce costs and increase the facility of coupling the posterior frame component 1004 with the frame 1010.

These secondary connectors can be used in combination with the outriggers to couple the anterior and posterior modules together. Further, these secondary connectors can be disposed on portions of the anterior and posterior modules that are generally abutting when the anterior and posterior modules are positioned or coupled together as an assembly. In particular, these secondary connectors can be used as an initial coupling mechanism to hold the anterior and posterior modules together as an assembly while the outriggers are attached or detached from the assembly. Thus, the overall assembly, including the outriggers and other components discussed herein, can enable a wearer to quickly manipulate an interchange any given component of the assembly.

Figure 48A:
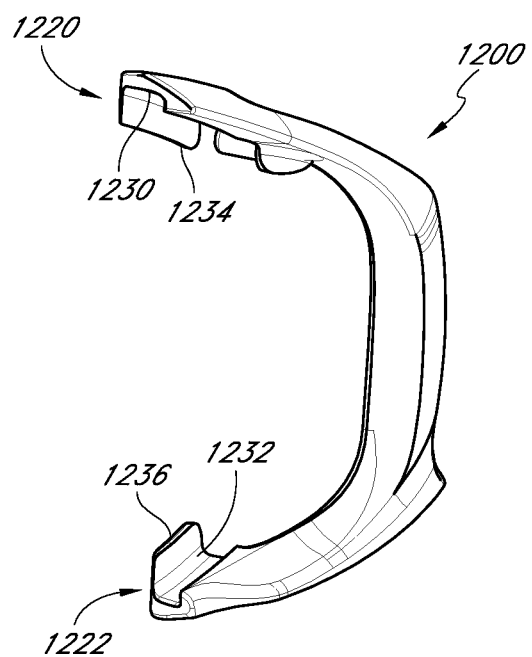
FIG. 48A is a front perspective view of the outrigger of the goggle shown in FIG. 44, according to an embodiment.
Figure 48B:
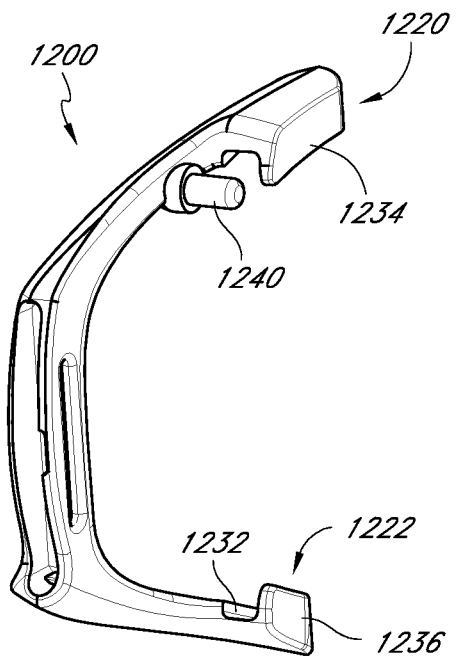
FIG. 48B is a rear perspective view of the outrigger shown in FIG. 48A.
Figure 49:
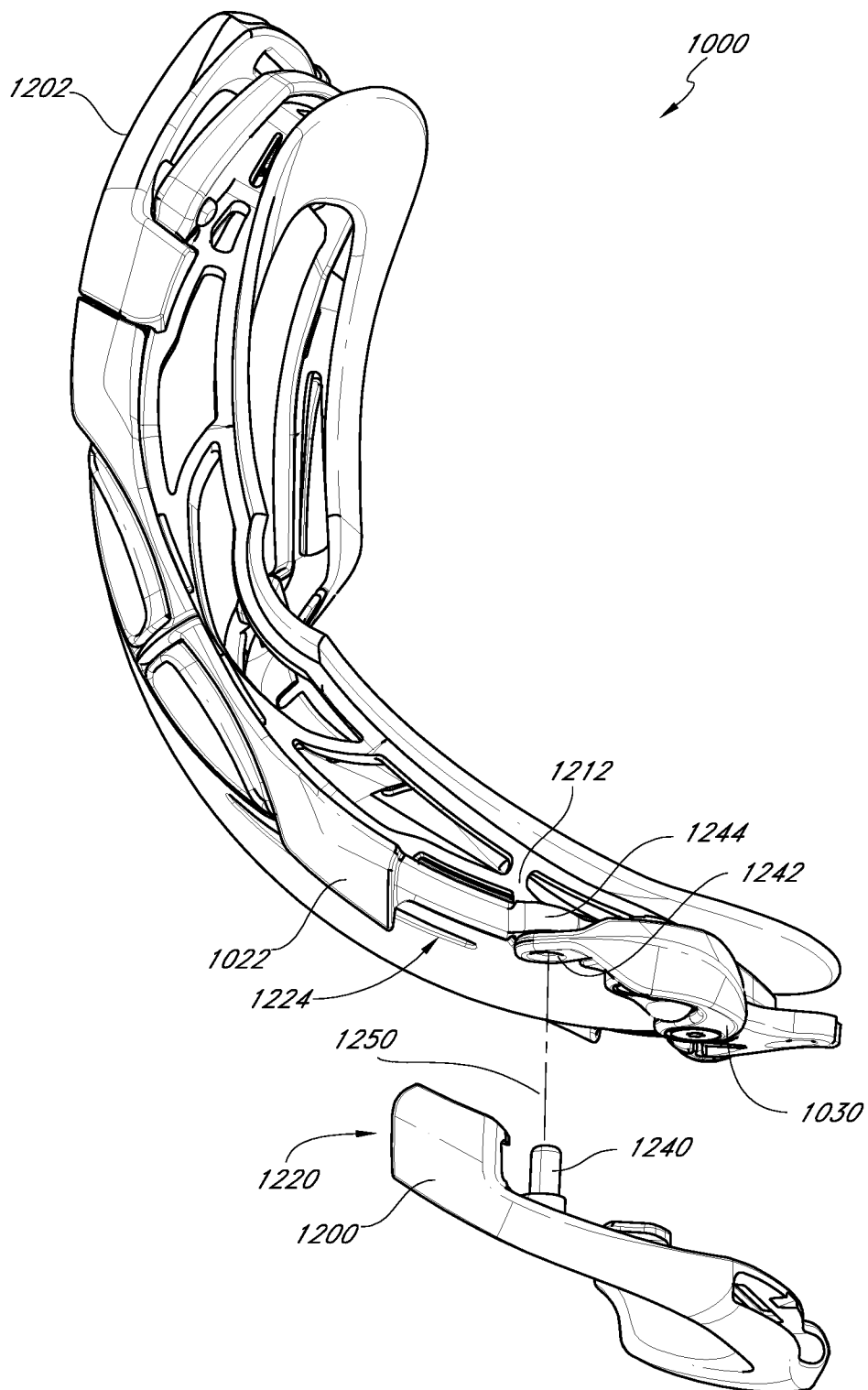
FIG. 49 is a top perspective view of the goggle shown in FIG. 44, wherein an outrigger is shown in a detached position.
Figure 50:
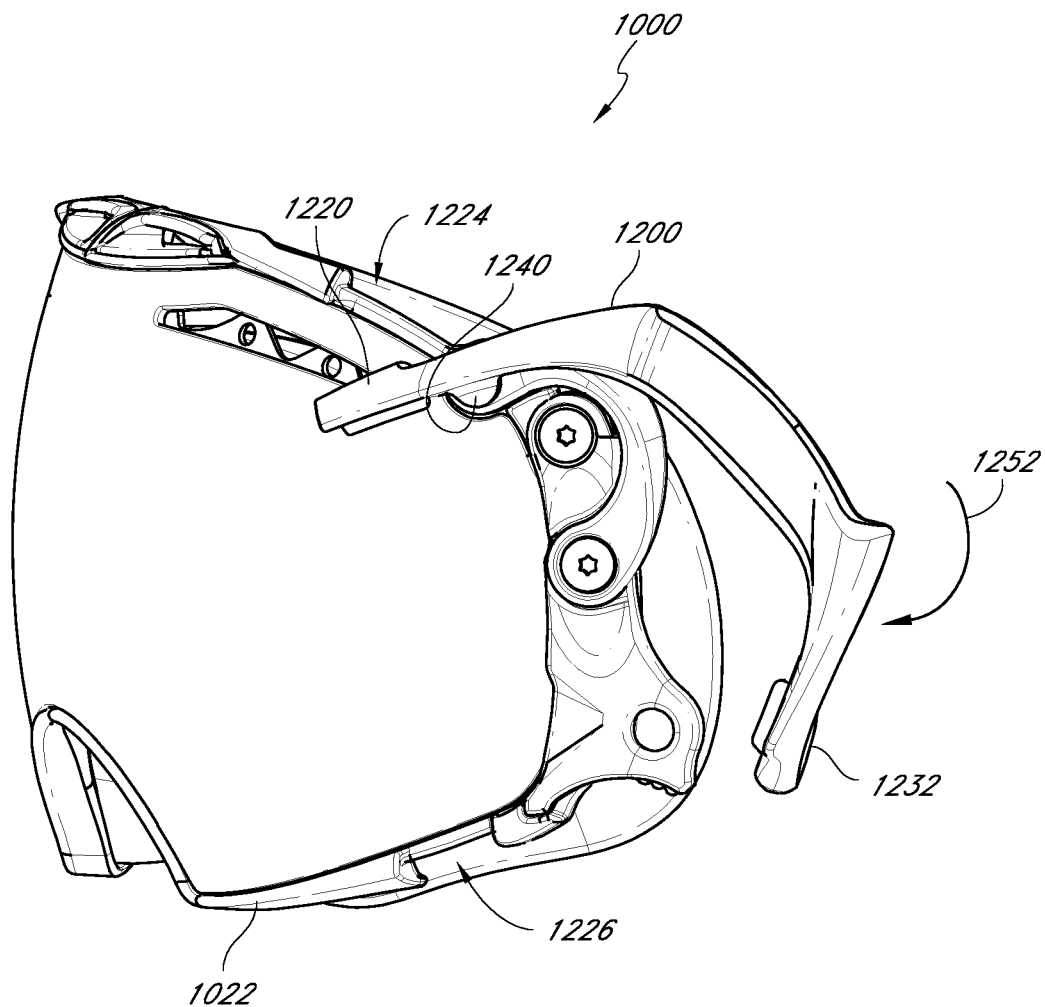
FIG. 50 is a side view of the goggle shown in FIG. 44, wherein the outrigger is being attached to the goggle, according to an embodiment.

Referring to FIGS. 48A-B, the outrigger 1200 can comprise fastening portions 1220, 1222. The fastening portions 1220, 1222 can be configured to engage with and secure the at least the anterior and posterior frame portions 1022, 1212 together. For example, at least one of the anterior and posterior frame portions 1022, 1212 can comprise one or more coupling regions where the fastening portions 1220, 1222 can engage with the anterior and posterior frame portions 1022, 1212. As shown in FIGS. 49-50, the goggle 1000 can comprise upper and lower coupling regions 1224, 1226 that can act as designated areas along the anterior and posterior frame portions 1022, 1212 whereat the fastening portions 1220, 1222 can be coupled. In some embodiments, the coupling regions 1224, 1226 can comprise at least one structure, such as a recess, protrusion, slot, groove, aperture, and/or passage that can be used to engage with the fastening portions 1220, 1222 of the outrigger 1200. In the illustrated embodiment, the coupling regions 1224, 1226 can comprise a recess formed in the anterior frame portion 1022. In addition, some embodiments can be configured such that other components such as the lens can be secured or engaged by the fastening portions 1220, 1222.

Figure 51:
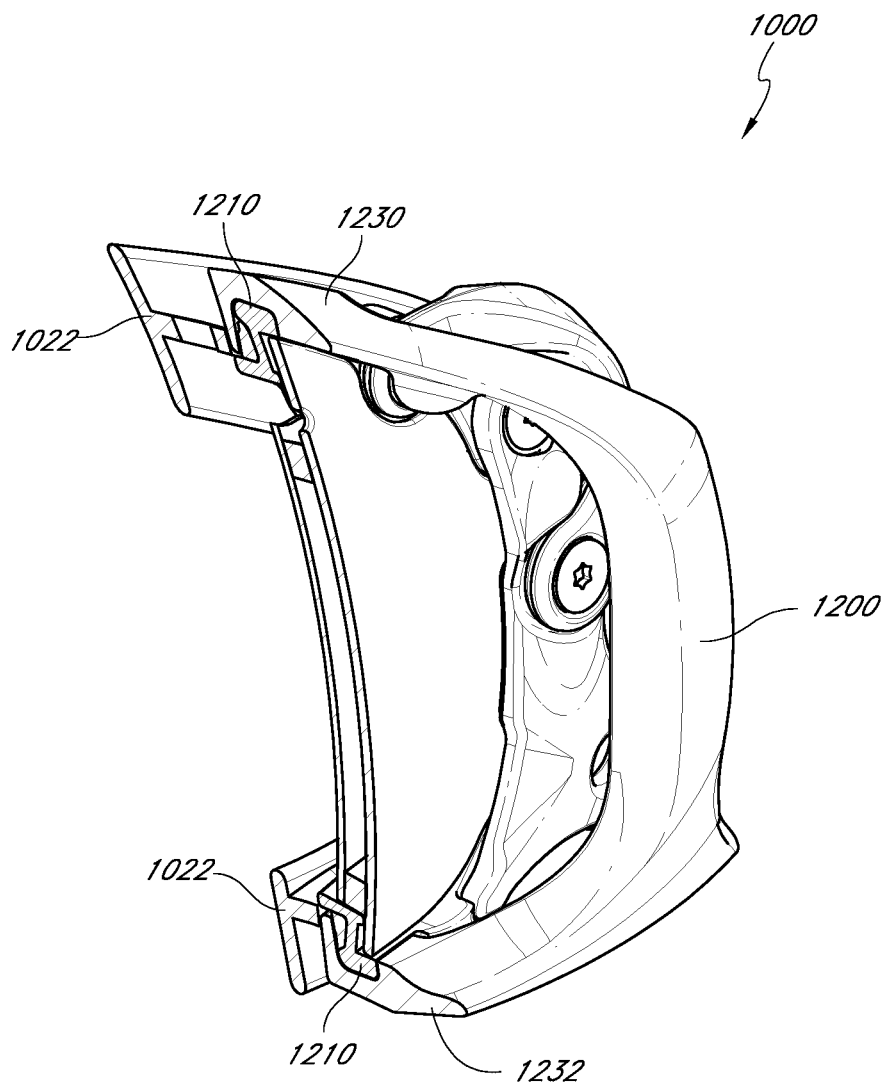
FIG. 51 is a perspective across-sectional view of the goggle taken along section lines 51-51 of FIG. 44.

Further, in some embodiments, the fastening portions 1220, 1222 of the outrigger 1200 can comprise recessed portions 1230, 1232 formed adjacent to sidewalls 1234, 1236. The recessed portions 1230, 1232 and the sidewalls 1234, 1236 can be configured to receive and secure portions of the anterior and posterior frame portions 1022, 1212 together. As shown in FIG. 51, the anterior and posterior frame portions 1022, 1212 can be coupled together with portions thereof being received into the recessed portions 1230, 1232 of the fastening portions 1220, 1222. The sidewalls 1234, 1236 of the fastening portions 1220, 1222 of the outrigger 1200 can be positioned against the posterior frame portions 1212 while a corresponding wall or body of the outrigger 1200 can be positioned against the anterior frame portion 1022.

The fastening portions 1220, 1222 can be clamped or snapped onto the anterior and posterior frame portions 1022, 1212 to secure the engagement between the outrigger 1200 and the frame. Thus, in some embodiments, the fastening portions 1220, 1222 can comprise protrusions or recesses that snap against corresponding recesses or protrusions of the anterior and posterior frame portions 1022, 1212. Further, the fastening portions 1220, 1222 can fit tightly over the anterior and posterior frame portions 1022, 1212 to secure them together.

FIGS. 49-51 illustrate positions of the outrigger 1200 as it is being moved into engagement with the goggle. The initial placement of the outrigger 1200 relative to the frame can be facilitated using a pin on the outrigger 1200. For example, as shown in FIGS. 48B-49, the outrigger 1200 can comprise an engagement pin 1240 that extends from a body of the outrigger 1200. The pin 1240 can be configured to engage with one or both of the anterior and posterior frame portions 1022, 1212 and provide a rotational engagement between the outrigger 1200 and the frame. The pin 1240 can also fix the position of the outrigger 1200 relative to the anterior and posterior frame portions 1022, 1212 when the outrigger 1200 is in a final assembled position, as discussed below.

During assembly, the pin 1240 of the outrigger 1200 can be inserted into an aperture 1242 of the link 1030 of the goggle 1000 and into an aperture 1244 of the anterior frame portion 1022. The top view of FIG. 49 illustrates an alignment axis 1250 along which the pin 1240 must pass to be aligned with the apertures 1242, 1244. After the pin 1240 has been passed through the apertures 1242, 1244, the outrigger 1200 can be rotated toward an assembled position (shown in FIG. 51) until the fastening portions 1220, 1222 snap into engagement with the coupling regions 1224, 1226 formed in the anterior and posterior frame portions 1022, 1212. The succession of the rotational motion 1252 is illustrated in FIGS. 50-51.

Once in the assembled position as shown in FIG. 51, the outrigger 1200 can engage and clamp both the anterior and posterior frame portions 1022, 1212 together in a secure arrangement. The outriggers can thus interconnect the components or modules of the goggle together without requiring the use of specialized tools, single-use fasteners or permanent fasteners. This superior interchangeability allows the wearer to customize and replace components or modules as desired. For example, the wearer can replace the posterior frame portion 1212 depending on a desired activity or comfort level. Similarly, the anterior frame portion 1022 can also be replaced as desired.

The features and structures of some embodiments, such as the substantially rigid anterior module 900, can be incorporated into any variety of goggle embodiments. For example, a substantially rigid anterior module can be used in combination with an isostatic faceplate mechanism. Further, a substantially rigid anterior module can be used in combination with an interchangeable lens structure.

FIGS. 52-58 illustrate yet another embodiment of eyewear that can incorporate features and aspects, in whole or part, of embodiments and structures discussed above. The embodiment illustrates another quick release lens mechanism that can be used with a goggle as well as an eyeglass. Although the illustrated embodiment shows an eyeglass, the quick release lens mechanism can also be used with a goggle.

Figure 52:
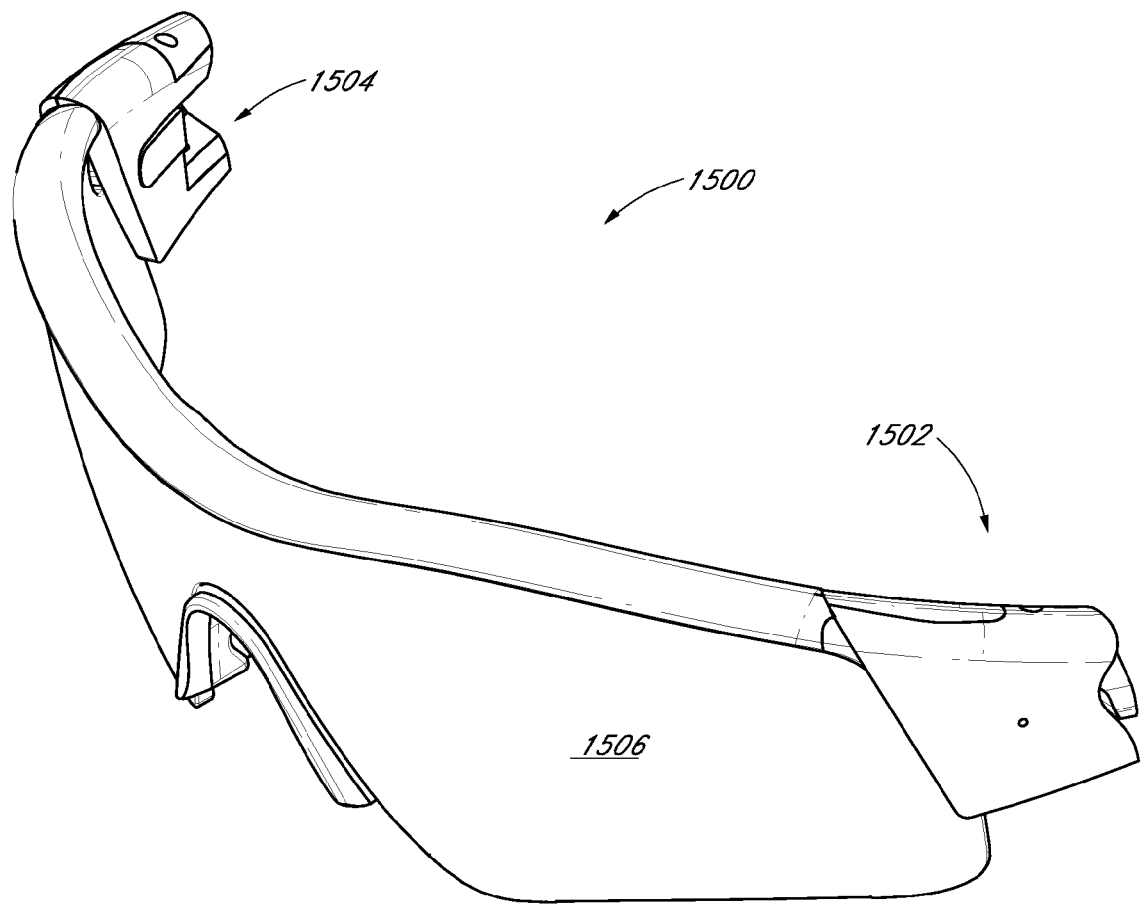
FIG. 52 is a perspective view of an eyeglass, according to another embodiment.

FIG. 52 is a perspective view of an eyeglass 1500, according to an embodiment. The eyeglass 1500 can comprise a unique quick release lens mechanism having an active restraint 1502 and a passive restraint 1504 that can serve to secure a lens 1506 relative to the eyeglass 1500. The eyeglass 1500 can also comprise a frame 1508 configured to support the lens 1506 in the field of view of the wearer, as discussed herein.

The lens engagement mechanism can operate much like the engagement mechanism described above with respect to FIGS. 31A-32B. The text and figures referenced above will not be repeated here, but are incorporated by reference and are considered to be alternative structures that can be used with other types of eyewear, such as the eyeglasses 1500 shown in FIGS. 52-58.

Figure 53:
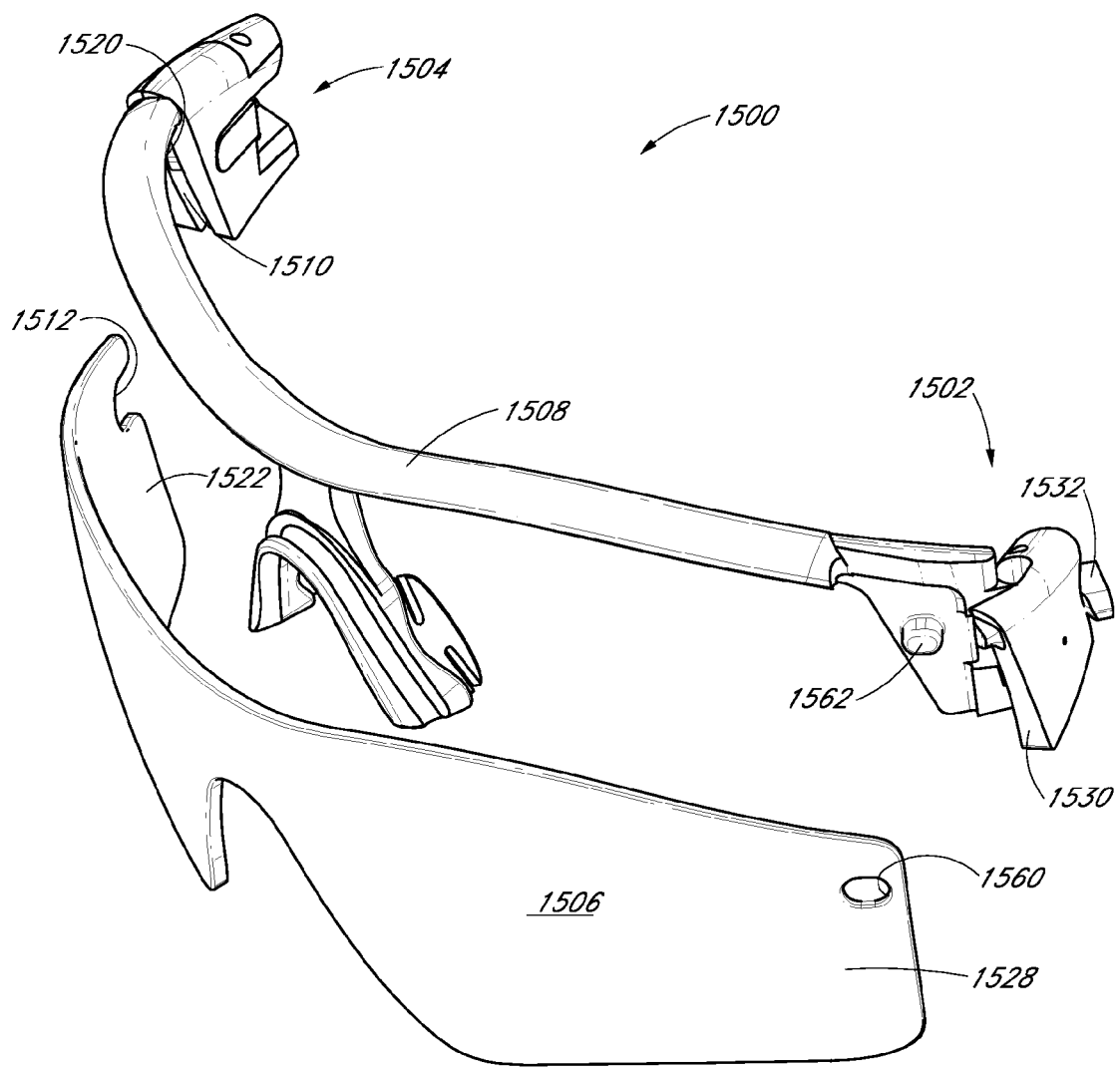
FIG. 53 is a perspective view of the eyeglass shown in FIG. 50, wherein an engagement mechanism is in the open position and a lens of the eyeglass is separated from the eyeglass.
Figure 54:
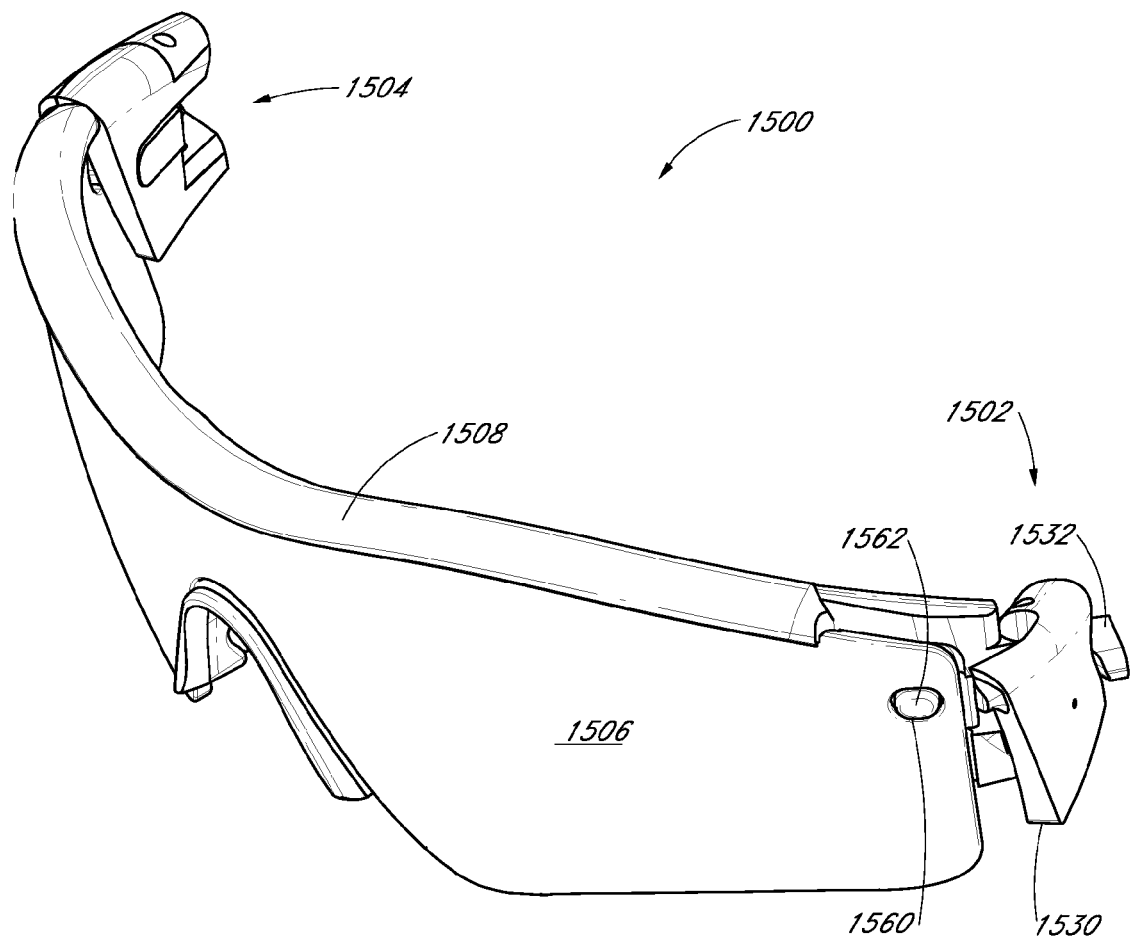
FIG. 54 is a side perspective view of the eyeglass shown in FIG. 50, wherein the engagement mechanism of the eyeglass is in an open position.

Referring to FIGS. 52-53, the passive restraint 1504 can comprise an engagement socket 1510 configured to engage with a corresponding retention structure 1512 of the lens 1506. The retention socket 1510 can be formed to comprise an engagement member 1520, such as a protrusion, slot, and/or recess that can engage with a corresponding recess, slot, and/or protrusion formed as the retention structure 1512 of the lens 1506. In the illustrated embodiment, the engagement member 1520 of the retention socket 1510 comprises a protrusion that is received into a slot (retention structure 1512) formed along a first lateral end 1522 of the lens 1506 when the first lateral end 1522 of the lens is inserted into the retention socket 1510.

In some embodiments, the engagement member 1520 of the retention socket 1510 can be positioned on an inner, anterior face of the retention socket 1510 such that the engagement member 1520 can engage a retention structure (such as an aperture) formed in the lens 1506 from a position anterior to the lens 1506. However, the engagement member 1520 can also be positioned on an inner posterior face of the retention socket 1510 such that the engagement member 1520 can engage a retention structure (such as an aperture) formed in the lens 1506 from a position posterior to the lens 1506.

Additionally, the active restraint 1502 can be configured to engage with a second lateral end 1528 of the lens 1506 in order to at least partially constrain the lens 1506 against anterior motion. For example, the active restraint 1502 can comprise a gate 1530. The gate 1530 can be moved between an engaged position and a disengaged position in order to allow the lens 1506 to be retained or released relative to the frame 1508 of the eyeglass 1500. In some embodiments, the gate 1530 can pivot relative to the frame 1508. In other embodiments, the gate 1530 can slide or translate relative to the frame 1508. The gate 1530 can be attached to the frame 1508 and maintained connected with the frame 1508 while in the engaged or disengaged positions. However, the gate 1530 can also be detachable from the frame 1508 and separable therefrom.

Figure 55:
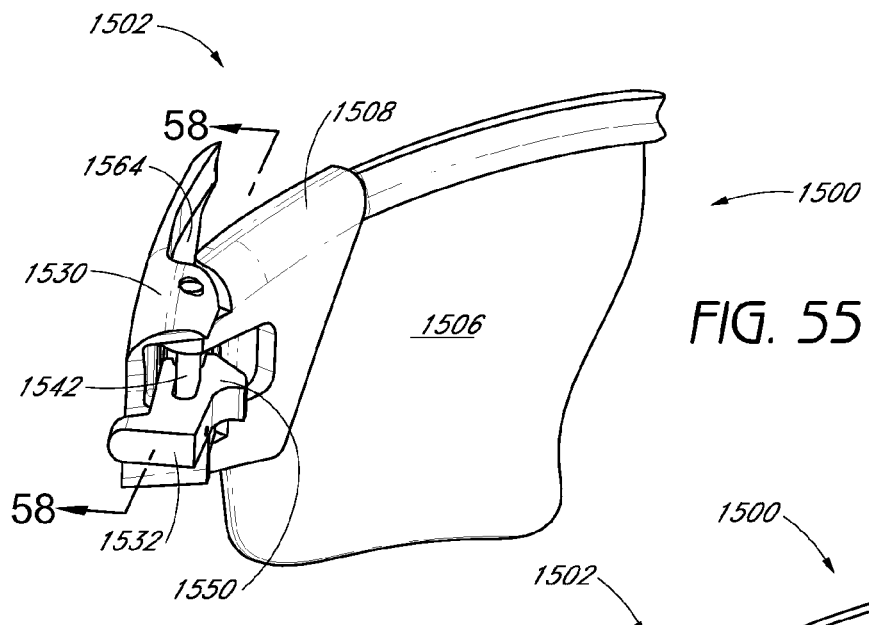
FIG. 55 is a rear perspective view of the eyeglass shown in FIG. 50, wherein the engagement mechanism of the eyeglass is in an open state and a latch member is in a disengaged position.
Figure 56:
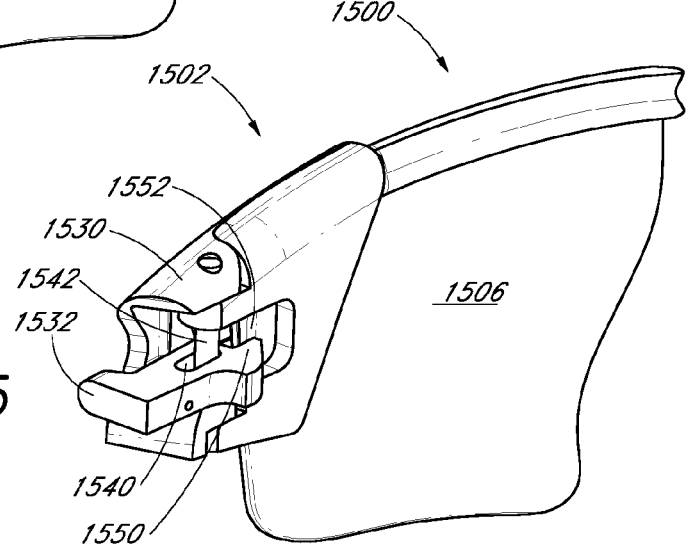
FIG. 56 is a rear perspective view of the eyeglass shown in FIG. 50, wherein the engagement mechanism of the eyeglass is in a closed state and the latch member is in the disengaged position.
Figure 57:
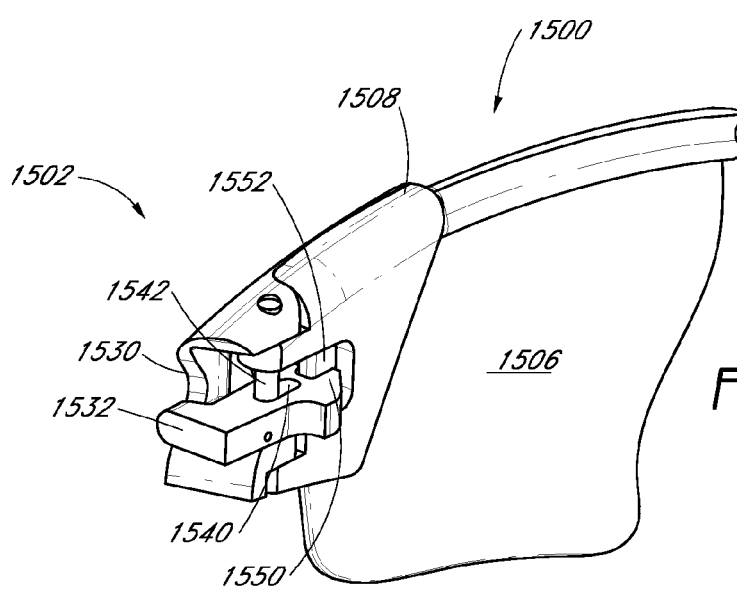
FIG. 57 is a rear perspective view of the eyeglass shown in FIG. 50, wherein the engagement mechanism of the eyeglass is in the closed state and the latch member is in an engaged position.

In some embodiments, the active restraint 1502 can further comprise a latch member 1532. As illustrated in FIGS. 55-57, the latch member 1532 can be moved between a locked position and an unlocked position. FIG. 55 illustrates the gate 1530 in a disengaged or open position and the latch member 1532 in the unlocked or open position. FIG. 56 illustrates the gate 1530 in an engaging or closed position and the latch member 1532 in the unlocked or open position. FIG. 57 illustrates the gate 1530 in an engaged or closed position and the latch member 1532 in the locked position. In some embodiments, when the latch member 1532 is in the unlocked position (as shown in FIGS. 55-56), the gate 1530 can rotate freely. However, when the latch member 1532 is in the locked position (as shown in FIG. 57), the gate 1530 can be constrained against rotation.

For example, the latch member 1532 can comprise an elongate body having a slot 1540 formed therein. The slot 1540 can be configured to receive a hinge pin 1542 that forms a pivot joint with the frame 1508, the gate 1530, and an earstem (not shown). The slot 1540 can be an elongate slot such that when the pin 1542 is received therein, the pin 1542 can travel between first and second ends of the slot, which can provide relative sliding movement between the pin 1542/frame 1508 and the latch member 1532. For example, the slot 1540 can define a travel distance of between at least about 0.1 inches and/or less than or equal to about 0.5 inches. In some embodiments, the travel distance can be about 0.3 inches. In such an embodiment, the latch member 1532 can slide between at least two positions, such as the locked and unlocked positions mentioned above. In the locked position, the pin 1542 is disposed in a first end of the slot 1540, and in the unlocked position, the pin 1542 is disposed in a second end of the slot 1540. In order to facilitate movement of the latch member 1532, the latch member 1532 can comprise a tab or gripping end that enables a wearer to grip and pull or push the latch member 1532 between the locked and unlocked positions.

The latch member 1532 can also be configured to engage a portion of the frame 1508 for preventing movement of the gate 1530 relative to the frame 1508. The latch member 1532 can comprise an engaging end 1550 having a tooth or projection formed thereon. When in the locked position, as shown in FIG. 57, the engaging end 1550 of the latch member 1532 can contact against a portion 1552 of the frame 1508 to prevent rotation of the latch member 1532.

Figure 58:
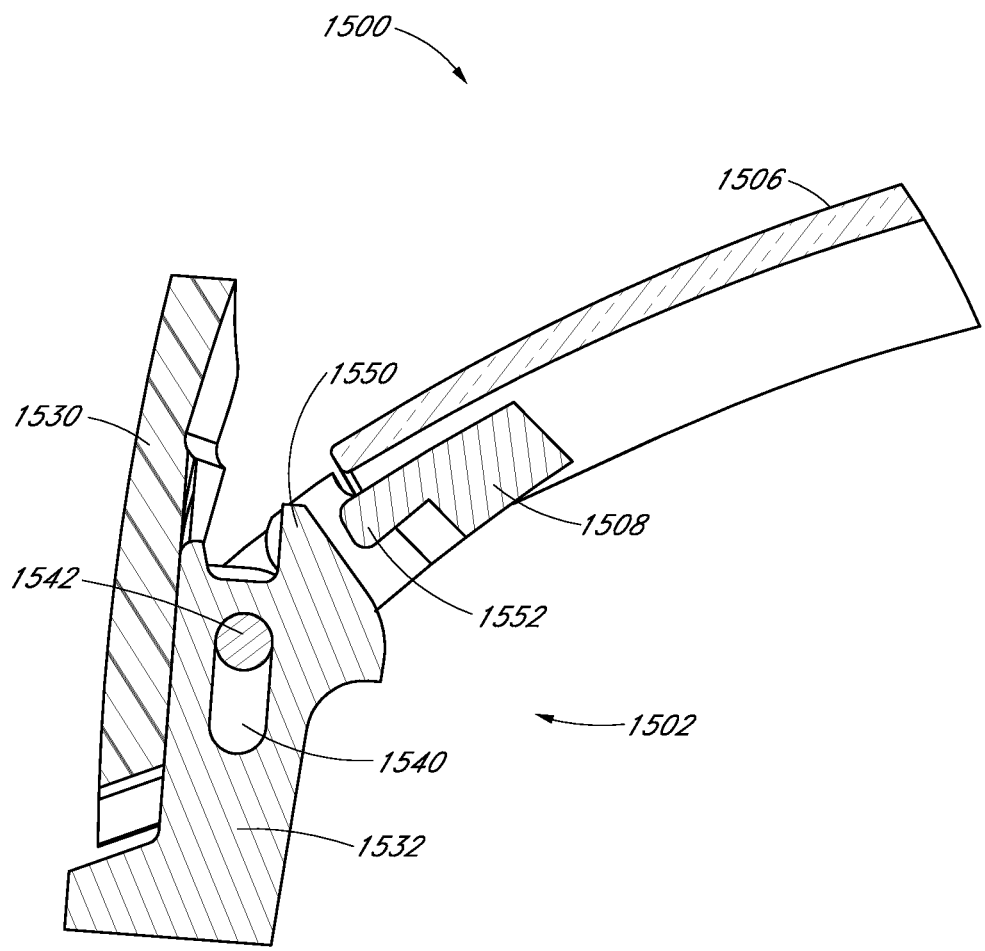
FIG. 58 is a top cross sectional view taken along lines 58-58 of FIG. 55, illustrating pivoting clearance of the engagement mechanism and the latch member in the disengaged position.

In some embodiments, the engaging end 1550 can define a slot for receiving the portion 1552 of the frame 1508. The illustrated embodiment of FIG. 58 shows a pair of opposing teeth with a slot disposed therebetween. The slot of the engaging end 1550 can thereby receive the portion 1552 of the frame 1508 and resist rotational movement in either direction relative to the frame 1508. Further, the engaging end 1550 can further comprise an engagement mechanism for engaging with a corresponding structure of the portion 1552 of the frame 1508 for maintaining the latch member 1532 in the locked position. The engagement mechanism can comprise a protrusion and/or recess for engaging (i.e., by frictional or snap engagement) with a corresponding recess and/or protrusion of the frame 1508.

Further, as illustrated in FIG. 58, in some embodiments, the latch member 1532 and the gate 1530 can be rotationally coupled relative to each other and in contact such that the gate 1530 cannot rotate without the latch member 1532 and visa versa. Thus, the sliding movement of the latch member 1532 between locked and unlocked positions to prevent or permit rotational movement of the latch member 1532 also prevents or permits movement of the gate 1530 relative to the frame 1508. Accordingly, in some embodiments, rotational movement of the gate 1530 can be restrained relative to the frame 1508 by sliding the latch member 1532 between locked and unlocked positions. The latch member 1532 can pivot along with the gate 1530 when the latch member 1532 is in the unlocked position, as shown in FIG. 58, because the engaging end 1550 of the latch member 1532 has been pulled back to provide rotational clearance from the portion 1552 of the frame 1508 that would otherwise prevent rotation of the latch member 1532 if the latch member 1532 were in the locked position.

Referring again to FIGS. 53 and 54, in some embodiments, the lens 1506 and the frame 1508 can comprise corresponding engagement structures disposed adjacent to the second end 1528 of the frame 1508 for enhancing the engagement of the lens 1506 relative to the frame 1508. The engagement structures can comprise corresponding slots, protrusions, and/or recesses that engage with each other to provide further stability and engagement. In the illustrated embodiment, the lens 1506 can further comprise an aperture 1560 and the frame can further comprise a protrusion 1562. The protrusion 1562 can be received into the aperture 1560 of the lens 1506. This engagement can provide initial stability and fixation when installing the lens 1506 into the frame 1508. Thereafter, the gate 1530 can be closed to cover a portion of the second lateral end 1528 of the lens 1506 to provide additional constraint of the lens 1506 relative to the frame 1508.

Further, in some embodiments, the gate 1530 can comprise a corresponding retention structure 1564 configured to engage with a portion of the lens 1506 and/or a portion of the frame 1508. The retention structure 1564 can comprise a protrusion, slot, and/or recess that that can provide a further engagement of the gate 1530 relative to the frame 1508. For example, a protrusion of the gate 1530 could be snap fitted into an aperture or edge of the frame 1508 to reduce accidental dislodgement of the gate 1530 from the engaged position.

Additionally, although FIGS. 52-58 illustrate an embodiment of an eyeglass having a partial orbital, it is contemplated that these features can also be implemented with a full orbital frame. Additionally, the alternative lens retention mechanisms disclosed further above can also be incorporated into eyewear, such as an eyeglass having partial or full orbitals.

In addition, in accordance with some of the embodiments of the goggle discussed above, the present inventions also provide for methods of interchanging/modifying anterior and/or posterior modules of the goggle, an isostatic faceplate of the goggle, a lens and/or retention mechanism of the goggle, and/or a rigid faceplate of the goggle. Thus, various methods are provided for using and interchanging/modifying the goggle using a modular system to incorporate desired characteristics and properties utilizing one or more of the features of the goggle embodiments discussed above. These methods can be performed at a point-of-sale by a seller or periodically as needed by an owner/wearer. The methods can be performed in a single instance or repeatedly over the life of the goggle. Kits can also be provided that can include one or more of the components discussed above and/or other components for use with an embodiment of the goggles.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. Eyewear comprising:
   a frame;
   a lens configured to be fitted against the frame;
   an engagement mechanism comprising a gate, a hinge pin, and a latch member, the gate being coupled to the frame and being operative to move along a first path between an open position and a closed position, the latch member being functionally connected to the gate and being constrained to move along the first path together with the gate upon movement of the gate, the latch member further being movable relative to the gate along a second path between a disengaged position and an engaged position to disengage or engage with at least one of the lens and a portion of the frame to prevent movement of the gate relative to the frame when the latch member is in the engaged position to maintain the lens fitted against the frame, wherein the first path is different from the second path, the first path being a rotational path, wherein the hinge pin defines a generally vertical axis about which the gate and the latch member rotate when moving between the open position and the closed position.

2. The eyewear of claim 1, wherein the latch member is slidable relative to the gate.

3. The eyewear of claim 2, wherein the second path is a generally linear path.

4. The eyewear of claim 3, wherein the linear path is generally horizontal.

5. The eyewear of claim 1, further comprising a biasing member disposed intermediate the latch member and the gate, the biasing member being configured to urge the latch member to the engaged position.

6. The eyewear of claim 1, wherein the lens is a unitary lens.

7. The eyewear of claim 1, wherein the engagement mechanism is located in a first lateral region of the eyewear.

8. The eyewear of claim 7, further comprising a second engagement mechanism located in a second lateral region of the eyewear.

9. The eyewear of claim 8, wherein the second engagement mechanism comprises a protrusion for receiving a recess on the lens.

10. The eyewear of claim 1, wherein the engagement mechanism comprises a protrusion that is received in a recess or slot on the lens.

11. Eyewear comprising:
    a frame;
    a lens configured to be fitted against the frame;
    an engagement mechanism comprising a gate, a hinge pin, and a latch member, the gate being coupled to the frame and being operative to move along a first path between an open position and a closed position, the latch member being functionally connected to the gate and being constrained to move along the first path together with the gate upon movement of the gate, the latch member further being movable relative to the gate along a second path between a disengaged position and an engaged position to disengage or engage with at least one of the lens and a portion of the frame to prevent movement of the gate relative to the frame when the latch member is in the engaged position to maintain the lens fitted against the frame, wherein the first path is different from the second path, the first path being a rotational path, wherein the hinge pin defines a first rotational axis about which the gate and the latch member rotate when moving between the open position and the closed position, wherein the latch member comprises an elongate slot and wherein the hinge pin passes through the elongate slot when the latch member and the gate are in an assembled state.

12. The eyewear of claim 11 wherein the latch member is slideable relative to the gate such that the hinge pin moves between first and second ends of the elongate slot when the latch member is moved between the disengaged and engaged positions.

13. Eyewear comprising:
    a frame;
    a lens configured to be fitted against the frame;
    an engagement mechanism comprising a gate and a latch member, the gate being coupled to the frame and being operative to move along a first path between an open position and a closed position, the latch member being functionally connected to the gate and being constrained to move along the first path together with the gate upon movement of the gate, the latch member further being movable relative to the gate along a second path between a disengaged position and an engaged position to disengage or engage with at least one of the lens and a portion of the frame to prevent movement of the gate relative to the frame when the latch member is in the engaged position to maintain the lens fitted against the frame, wherein the first path is different from the second path, wherein the latch member comprises an engaging end configured to mate against at least one of the frame and the lens, the engaging end of the latch member comprising a toothed portion having a ramped surface, the ramped surface being configured to contact the frame as the latch member is moved from the disengaged position to the engaged position.

* * * * *